United States Patent
Bardy et al.

(10) Patent No.: US 11,690,535 B2
(45) Date of Patent: Jul. 4, 2023

(54) MOBILE SYSTEM ALLOWING ADAPTATION OF THE RUNNER'S CADENCE

(71) Applicants: Universiteit Gent, Ghent (BE); CENTRE HOSPITALIER ET UNIVERSITAIRE DE MONTPELLIER, Montpellier (FR); Université de Montpellier, Montpellier (FR); Clinique BEAU-SOLEIL, Montpellier (FR); Maynooth University, Maynooth (IE)

(72) Inventors: Benoît Bardy, Montpellier (FR); Simone Dalla Bella, Clapiers (FR); Loic Damm, Montpellier (FR); Dobri Dotov, CDMX (MX); Déborah Varoqui, Chaville (FR); Jeska Buhmann, Ghent (BE); Marc Leman, Ghent (BE); Bart Moens, Ghent (BE); Edith Van Dyck, Ghent (BE); Sean O'Leary, Maynooth (IE); Joseph Timoney, Maynooth (IE); Rudi Villing, Maynooth (IE); Tomas Ward, Maynooth (IE); Valérie Cochen de Cock, Montpellier (FR)

(73) Assignees: UNIVERSITEIT GENT, Ghent (BE); CENTRE HOSPITALIER ET UNIVERSITAIRE DE MONTPELLIER, Montpellier (FR); UNIVERSITÉ DE MONTPELLIER, Montpellier (FR); CLINIQUE BEAU-SOLEIL, Montpellier (FR); MAYNOOTH UNIVERSITY, County Kildare (IE)

(*) Notice: Subject to any disclaimer, the term of this patent is extended or adjusted under 35 U.S.C. 154(b) by 582 days.

(21) Appl. No.: 16/633,726

(22) PCT Filed: Jul. 26, 2018

(86) PCT No.: PCT/EP2018/070318
§ 371 (c)(1),
(2) Date: Jan. 24, 2020

(87) PCT Pub. No.: WO2019/020755
PCT Pub. Date: Jan. 31, 2019

(65) Prior Publication Data
US 2020/0289026 A1 Sep. 17, 2020

Related U.S. Application Data

(60) Provisional application No. 62/537,558, filed on Jul. 27, 2017.

(51) Int. Cl.
*A61B 5/11* (2006.01)
*A61B 5/00* (2006.01)
(Continued)

(52) U.S. Cl.
CPC ............ *A61B 5/112* (2013.01); *A61B 5/002* (2013.01); *A61B 5/02438* (2013.01);
(Continued)

(58) Field of Classification Search
CPC ........ A63B 71/0686; A63B 2071/0625; A63B 69/0028; A63B 2220/836; A63B 24/007;
(Continued)

(56) References Cited

U.S. PATENT DOCUMENTS

| | | | |
|---|---|---|---|
| 9,269,341 B1* | 2/2016 | Lemnitsky | ............... G10H 1/40 |
| 2010/0089224 A1 | 4/2010 | Fratti et al. | |
| 2015/0182149 A1 | 7/2015 | Rapoport et al. | |

OTHER PUBLICATIONS

Palven, P. "A Sound Art Installation based on the theory of coupled nonlinear oscillators", [dated 2004], [online], [retrieved May 20, 2022], Retrieved from the Internet <URL:http://www.electrohype.org/socialfield/PeterPalven_MasterThesis.pdfl>. 47 pages.*

(Continued)

*Primary Examiner* — Lawrence S Galka
(74) *Attorney, Agent, or Firm* — Cantor Colburn LLP

(57) ABSTRACT

A mobile music listening device synchronizing in a personalized way music and movement, and dedicated to improving the kinematics of the runner. Thanks to inertial units connected to a smartphone, the runner's steps are detected in (Continued)

Figure 1:
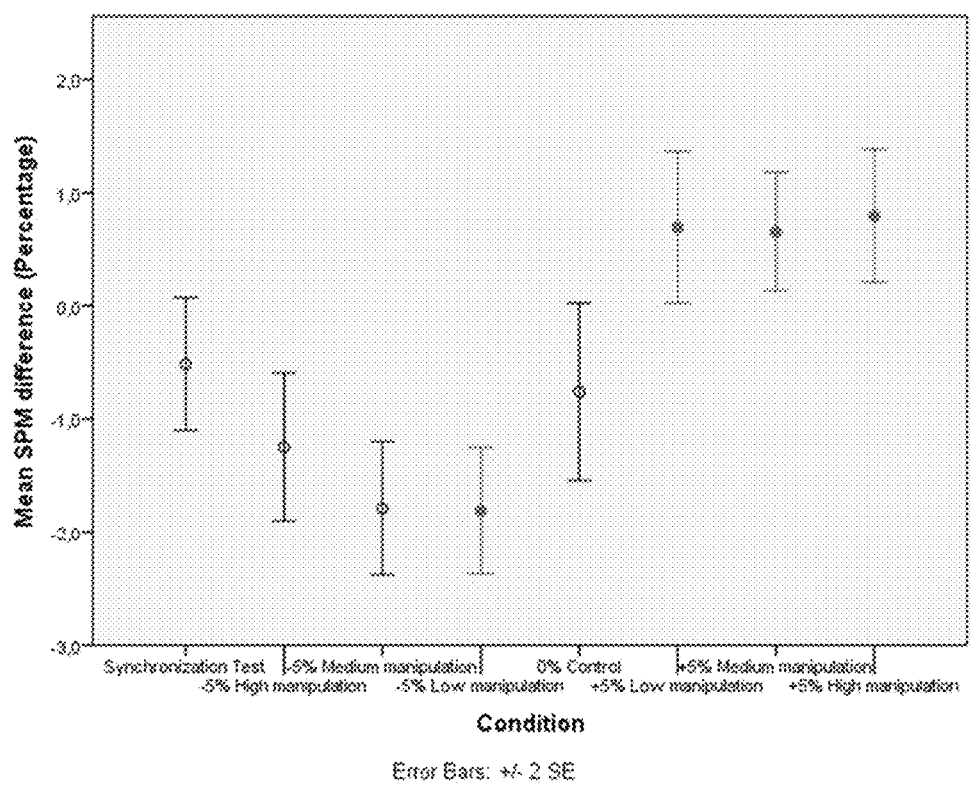

real time by the mobile application. A dedicated algorithm adapts the pulsation of the musical excerpts in such a way as to bring the runner to a suitable cadence, capable of preventing injuries.

A method for the synchronization of the rhythmic stimulation with the biological variability using a Kuramoto model characterized in that phase oscillator with a coupling term from the movement dynamics with parameters of, coupling strength, maximum and minimum frequencies for a fraction of the unmodified song frequency, maximum difference between the tempo and target frequency, Target the target frequency.

10 Claims, 35 Drawing Sheets
(32 of 35 Drawing Sheet(s) Filed in Color)

(51) Int. Cl.
  *A61B 5/024* (2006.01)
  *A61B 5/08* (2006.01)
  *H03L 7/099* (2006.01)
  *H04W 4/80* (2018.01)

(52) U.S. Cl.
  CPC .......... *A61B 5/0816* (2013.01); *A61B 5/1112* (2013.01); *A61B 5/681* (2013.01); *A61B 5/6823* (2013.01); *A61B 5/7292* (2013.01); *H03L 7/099* (2013.01); *H04W 4/80* (2018.02); *A61B 2503/10* (2013.01); *A61B 2505/09* (2013.01); *A61B 2562/0219* (2013.01)

(58) Field of Classification Search
  CPC ......... G10H 2220/37; G10H 2210/076; G10H 2210/375; G10H 2210/385; G10H 2210/391; G10H 2240/085
  See application file for complete search history.

(56) References Cited

OTHER PUBLICATIONS

"Arch structure and injury patterns in runners" Williams et al.; vol. 16,Nr:4,pp. 341-347.
"Quantifying rearfoot-forefoot coordination in human walking" Chang et al.; vol. 41,Nr:14,pp. 3101-3105.
"Lower extremity stiffness: implications for performance and injury" Authors: Butler et al.; vol. 18,Nr:6,pp. 511-517.
Chopra N. et al.: "On Synchronization of Kuramoto Oscillators", Decision and Control, 2005 and 2005 European Control Conference. CDC-E CC '05. 44th IEEE Conference on Seville, Spain Dec. 12-15, 2005; pp. 3916-3922.
International Search Report for Application No. PCT/EP2018/070318.
Juan A. Acebron et al.: "The Kuramoto model: A simple paradigm for syncronization phenomena", Reviews of Modern Physics, vol. 77, No. 1. Apr. 1, 2005; pp. 137-185.
Written Opinion for Application No. PCT/EP2018/070318.
"Changes in muscle activation patterns when running step rate is increased" Chumanov et al.;vol. 36,Nr:2,pp. 231-235.
"Effects of altered stride frequency and contact time on leg-spring behavior in human running" Morin et al.; vol. 40, Nr:15,pp. 3341-3348.
"Estimation of IMU and MARG orientation using a gradient descent algorithm" Madgwick et al.; pp. 1-7.
"Inertial Sensor-Based Stride Parameter Calculation From Gait Sequences in Geriatric Patients"; Rampp et al.; vol. 62, Nr:4,pp. 1089-1097.
"Nonlinear Complementary Filters on the Special Orthogonal Group" Mahony et al.; vol. 53,Nr:5,pp. 1203-1218.
"Preferred and optimal stride frequency, stiffness and economy: changes with fatigue during a 1-h high-intensity run" Hunter et al.; vol. 100,Nr:6,pp. 653-661.
"The effect of stride length on the dynamics of barefoot and shod running" Thompson et al.; vol. 47,Nr:11,pp. 2745-2750.
"The influence of running velocity and midsole hardness on external impact forces in heel-toe running" Nigg et al.; vol. 20,Nr:10,pp. 951-959.
"RRACE: Robust realtime algorithm for cadence estimation"; Karuei et al.; vol. 13,pp. 52-66.

* cited by examiner

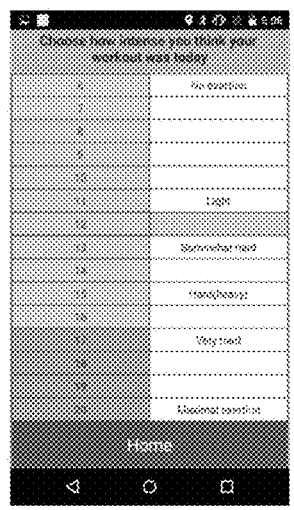
*Figure 67*
Hoe zou je je laatste training sessie beschrijven? Het was erg.
|  | Ik ben het helemaal eens | Ik ben het helemaal oneens |
|---|---|---|
| plezierig ? | | |
| verfrissend ? | | |
| stimulerend ? | | |
| opmonterend ? | | |
| bevredigend ? | | |
| verkwikkend ? | | |
| aangenaam ? | | |
| leuk ? | | |
*Figure 68*
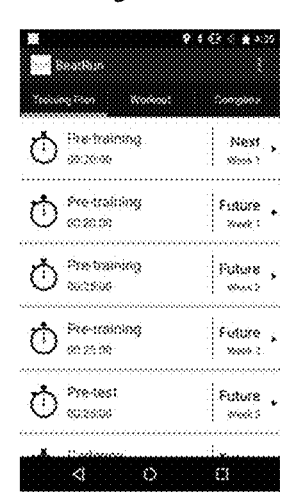
*Figure 69*

MOBILE SYSTEM ALLOWING ADAPTATION OF THE RUNNER'S CADENCE

CROSS REFERENCE TO RELATED APPLICATIONS

This application is a National Stage of PCT Application No. PCT/EP2018/070318 filed on Jul. 26, 2018, which claims priority to U.S. Provisional Application No. 62/537,558 filed on Jul. 27, 2017, the contents each of which are incorporated herein by reference thereto.

SUMMARY OF THE INVENTION

The BeatHealth system aims to develop a mobile music listening device synchronizing in a personalized way music and movement, and dedicated to improving the kinematics of the runner. Thanks to inertial units connected to a smartphone, the runner's steps are detected in real time by the mobile application. A dedicated algorithm adapts the pulsation of the musical excerpts in such a way as to bring the runner to a suitable cadence, capable of preventing injuries. A clinical version of this application is developed to improve walking parameters in patients with Parkinson's disease.

DETAILED TECHNICAL DESCRIPTION OF THE INVENTION AND THE INVENTIVENESS

The general aim of the BeatHealth project is to use the training capacities of the music to improve the kinematic parameters of the race in amateur athletes or those of walking in the Parkinsonian patient.

The tempo of most traditional musical compositions lies in an interval that includes the tempo of human locomotor activities, running or walking. In addition we have the ability to synchronize our movements with the pulsations of music, i.e. the accent intervening cyclically at the beginning of each musical time. So we took advantage of this ability to manipulate the cadence or tempo of the runner.

Making music at a specific tempo and asking the runner to synchronize in order to change his pace was not the aim: it would have led to assigning a double task to the runner, running and synchronization. On the contrary, we sought the parameters of music manipulation likely to engage the runner in a subliminal adaptation of his cadence. It is an adaptive system that has been developed to achieve this goal, ie the rhythmic characteristics of the music are manipulated in real time according to the cadence of the runner.

In order to make the runner and the mobile music application dialogue, BeatHealth is based on the following architecture:

two inertial units carried by the runner on each of its pins allow the real-time detection of the impact of each foot on the ground The mobile application gathers a music library with the annotation files of the pulsations of each song.

This information makes it possible to adapt the characteristics of each piece, which can thus be slightly compressed or expanded according to the requirements of the race.

This adaptation is carried out within limits dictated by musical aesthetics, too much adaptation would be detrimental to the quality of listening. If an important adaptation is required, the application automatically selects the song with a more suitable tempo. When changing from one song to another, the tempo change is progressive due to an alignment of the pulses of the two songs before the adaptation to the new tempo. Beyond the adaptation of the tempo of music, this architecture allows the control of the phase between the supports of the feet and the musical pulsations. Tempo and phase can be controlled independently. For example, for a musical tempo that is equal to the cadence of the runner, it is possible to cause the pulsation to occur before or after the step of the runner. It is this independent control of tempo and phase that allowed us to propose an original algorithm.

Our cadence training algorithm is based on the idea that it is possible to attract the runner to a target cadence by maintaining a phase shift. Let us take the most common case of a runner who has a cadence lower than the target cadence. The system will maintain both a slight difference in tempo, the tempo of the music being closer to the target tempo than the racer's rate, and a phase advance, ie the pulsation will occur in In advance of the pitch. The runner will then tend to increase his cadence to "catch up" the phase shift. This is what we have seen experimentally. The runner is driven to the target cadence.

Mobile applications on the market simply adopt a given tempo or leave the choice of it. We have therefore, during a proof of concept that we have designed, compared our approach with that of the other applications in the market. During a 9-week training session, we asked 28 amateur runners to use our mobile app. A reference cadence was measured during a barefoot running session. Indeed, we considered this cadence as more natural and likely to prevent the risk of injury. Of the 28 runners, 22 sets of exploitable data were collected. According to our predictions, 16 runners out of the 22 had a barefoot cadence greater than their paced feet, and we observed the effects of hearing stimulation during training in these 16 runners and the possibility of training them Towards the target cadence. The training consisted of two distinct phases during which the application broadcast music according to different algorithms:

Fixed musical tempo equal to the target cadence: this strategy is representative of the applications available on the market Musical tempo manipulated by our adaptive algorithm described above Our adaptive algorithm was able to increase the pitch frequency significantly after 5 sessions, in contrast to the constant tempo stimulation algorithm.

Algorithm Description

In this deliverable the stimulation parameters chosen to be implemented in BeatHealth Proof-of-Concept (POC) experiments will be outlined. For BeatPark, the parameters chosen are the direct result of the outcome of Task 2.1 and 2.2, targeting stimulation variability and adaptability. For BeatRun the specification of the stimulation parameters required two additional experiments conducted by WP3 in Task 2.3.

BeatPark—Stimulation parameters selected for the final version of the BeatHealth architecture The outcome of Tasks 2.1 and 2.2 (see Deliverable 2.3) showed that 1) rhythmic stimulation with so-called biological variability (long-range memory) embedded in the inter-beat-intervals allows improved performance as compared to isochronous beats, and that 2) adaptive stimulation in which the beat is weakly coupled to the patient's steps yield optimal performance. Note that adaptive stimulation with weakly coupled to the steps is also variable, thus incorporating all the beneficial effects of stimulus variability and adaptability. This mapping strategy (weak adaptive strategy) was superior as compared to all other non-adaptive and adaptive strategies tested in Tasks 2.1 and 2.2. Compared to the other reasonable candidates: non-adaptive stimulus with embedded long-range memory and adaptive stimulus with strong, immediate coupling, the weak adaptive is the only one that achieves optimal performance without compromise, by increasing both cadence and gait stability. These results led to using the weak adaptive mapping strategy as the most appropriate for the POC, using musical stimuli which in spite of providing the same effects of other simpler stimuli (i.e. a metronome) have the advantage of being motivating and well appreciated by the patients.

The weak adaptive mapping strategy is implemented via a coupled phase oscillator with frequency detuning (intrinsic frequency higher than the patient's self-selected) offers a unique blend of autonomy and cooperativeness. It can speed up cadence, it does not require patients to receive the explicit instruction to synchronize, it is easy to control and predict parametrically, and in general it is the most natural way to build an interactive musical player that mimics the dynamics of a human partner. This mapping strategy is implemented using on a phase oscillator dynamics (Kuramoto model of synchronization) which is particularly appropriate for patients with PD. The mapping strategy (i.e., simulating an interactive musical "partner") was implemented as a phase oscillator receiving a coupling term from the gait dynamics in terms of a sine function of the step phase:
$\dot{\theta}_{Machine} = \omega_{Machine} + N^{-1} k_{Machine} \sin(\theta_{Machine} - \theta_{Human})$ Here N=2, $\omega_{Machine}$ (rad/s) is the intrinsic preferred frequency of the musical player, and $k_{Machine}$ is the coupling gain. The continuous step phase θHuman is linearly extrapolated from the last two footfalls.

In the weak adaptive condition, the intrinsic frequency $\omega_{Machine}$ of the adaptive stimulus started at the participant's level and then gradually increased following a 15-s linear ramp, creating a so-called frequency detuning $\delta = \omega_{Machine} - W_{Human}$, and the coupling strength $k_{Machine}$ also increased in order to guarantee synchronization of the stimulus even if the participant did not "cooperate". For >15 s, $\omega_{Machine} = 1.2 \omega_{Human}$. This parametrization of the system allows implementing a good compromise between maintenance of a given frequency and a "cooperative tendency" in the adaptive stimulus. This was achieved via manipulation of the intrinsic frequency $\omega_{Machine}$ and coupling strength $k_{Machine}$ parameters. To this end, we set the coupling strength just over the critical value, $k_{Machine} = 1.1 * 2|\delta|$ (for more computational details, see Deliverable 2.3 and Periodic Report II).

BeatRun—Stimulation parameters selected for the final version of the BeatHealth architecture Tasks 2.1 and 2.2 did not allow to pinpoint final stimulation parameters for BeatRun POC The goal of the Task was to identify optimal parameters for rhythmic auditory stimulation (RAS) provided by the BeatHealth architecture. The effects of beat variability and beat adaptability on running performance were investigated. It was expected that RAS with ideal parameters would have led to maximal benefits on the energetic performance of runners. The general hypothesis was a reinforcement of the coupling between locomotion and respiration when listening to auditory stimulation with appropriate characteristics, associated with lower energy consumption.

Altogether, the results of the first Adaptability experiment during running indicate that RAS positively influenced the biomechanics and physiology of running in the first experiment, but this finding was not replicated in the subsequent ones (experiments 2 and 3, see Deliverable 2.3 and Periodic Report II). The effect of RAS seems not as robust as we thought after the first year of the project, and the factors governing this effect and potential confound variables need considerable attention. Moreover, the ground/treadmill comparison indicates a different locomotor dynamics and efficiency when participants run on the two surfaces, masking any potential effect of RAS. Finally, a large between-participants and between-trials variability was observed in these experiments, which was not expected based on the results of Experiment 1.

Variable RAS were first introduced in the form of white noise (Experiment 2) and then tested again with pink noise RAS in a subsequent experiment (Experiment 5, see Deliverable 2.3). Kinematic, LRC and energy consumption related variables were globally stable across all experimental conditions, and we could not find any benefit of RAS variability on our variables. Various and contrasting effects can explain this lack of significance across participants: the energy spent increased with RAS for some participants but decreased for others. Moreover the cost of running was affected differently with the type of complexity of RAS. The results based on white noise RAS do not contrast sufficiently with the ones obtained with periodic RAS to allow ranking these algorithms based on performance criteria. Pink noise RAS was not associated either with better performances: only 10% of participants significantly decreased their oxygen consumption when listening to this type of RAS.

Hence, it appears critical to evaluate and favour any beneficial effect of RAS to individualize the stimulation, and to consider the context in which the stimulation is provided (e.g., the surface). These considerations, although they depart from our previous hypotheses, are going to direct the next steps of the project.

Task 2.3 additional experiment conducted to find the optimal music alignment for the BeatRun POC Two experiments were conducted by WP3 in Task 2.3 to find the most optimal music alignment strategy to use in the BeatRun proof of concept (mobile) devices. The goal of the alignment strategy was to influence participants into a higher or lower cadence. An adjusted cadence could lead to a more optimal energy efficiency or reduced risk for injury, which could be used in the proof of concept.

An initial prototype with two simple alignment strategies was made. Both strategies were driven by a Kuramoto oscillator; leading to tempo and phase synchronization of the music to the runner. One strategy gradually shifted the music out of phase (negative, from 0° to −90°) and the other gradually shifted the music positively out of phase (0° to 90°). We hypnotized, based on previous BeatHealth research and the phase error correction mechanism, that a positive phase shift could lead to a lower cadence, while a negative phase could lead to a higher cadence. In all tests, running cadence deviated towards the hypothesized cadence (i.e., increased/decreased); whilst participants did not know in what condition they ran in. We thus concluded from this pilot that there is an influence of the relative phase to runner's cadence for our three participants; and that it is very likely that we will find this on a larger scale experiment.

Some shortcomings of the Kuramoto model for audio synchronization were found in the pilot and this led to an adjusted model: the second alignment strategy. The new strategy was also Kuramoto based with three parameters: coupling strength (α), maximum phase deviation/shift (β) and the target frequency (goal cadence).

The second experiment explored the adjusted model. 22 participants each ran 9 times: warm-up, a synchronization test, and 7 randomized conditions including control. All runs were around 4 minutes of self-paced running—a self selected tempo they could keep up for half an hour. Each of the 7 conditions attempted to manipulate the cadence and speed of the participants using a predetermined parameter set of the Kuramoto model. Three conditions were 5% speedup (subliminal 30°, barely noticeable 50° & conscious 70° phase shifts); three conditions were similar slowdown conditions and one was control (no phase shifting).

Initial data exploration showed that the subconscious phase shift (or the 30° phase shift) worked best to influence the cadence of the participants. Around 74% of the participants decreased their cadence 1% or more in the subliminal slowdown condition; whilst 43% of the participants increased their cadence 1% in the subliminal speedup condition. Around 47% of the participants decreased their cadence 2% or more in the subliminal slowdown condition; whilst 24% of the participants increased their cadence 2% in the subliminal speedup condition. Note that the intended decrease or increase would be around 5%, but no participant adjusted their cadence this much. No clear results were obtained from visual inspection of the speed (km/h).

Statistical analysis showed that the manipulation of the music had a significant main effect on cadence (SPM) and velocity (km/h). Contrasts revealed that all speeding-up conditions resulted in significantly higher running cadence than the control condition. Additionally, the subliminal speeding-up condition resulted in significantly higher velocity than the control condition. The subliminal slowdown condition resulted in significantly lower running cadence than the control condition, however velocity did not show any significant effects. We note that more in depth analysis also revealed a gender effect: the reaction to the stimuli was different for males then for females. However; due to the low number of participants per group and some invalid data; the groups were relatively small to compare. These results are similar to our data exploration: the subliminal conditions (both speedup & slowdown) seem to work best to influence participants. The condition did not influence qualitative measurements such as BORG & PACES.

The unified/adapted Kuramoto model can be used to manipulate runners' cadence and frequency by means of a subliminal phase shift. Optimal results were obtained using a target frequency+/−5%, a coupling strength of 0.03 and a maximum phase offset of 0.55 (maximum of 33° phase shift). This resulted in a 1% increased cadence for the speedup condition and a 2% decreased cadence for the slowdown condition.

Annex I

Report on Task 2.3 Experiment

Determining the Alignment Strategy to be Used in the BeatRun Proof of Concept

We hypothesize the following, based on previous experience obtained in BeatHealth, DJogger and entrainment/tapping literature:
1. When music is played with a strongly implied beat, a gait matching tempo and a negative phase shift, we expect a relative phase correction response towards 0° which results in an increased cadence.
   Or: if SPM & BPM are similar, and if a beat occurs just prior to a step (i.e., negative relative phase), the user will try to 'catch up' to the beat and thus speed up (cadence and velocity).
2. When music is played with a strongly implied beat, a gait matching tempo and a positive phase shift, we expect a relative phase correction response towards 0° which results in a decreased cadence.
   Or: if SPM & BPM are similar, and the beat occurs a bit later then a step (i.e., positive relative phase), the user will try to slow down to get in sync (cadence and velocity).

The experiment developed in Task 2.3 will try to confirm this hypothesises by using BeatHealth technology for exploring different alignment strategies. If this is the case, the concept can be applied in the BeatRun POC to subliminally manipulate runner's cadence.

First Pilot Experiment a. Introduction

Previous BeatHealth experiments have shown that the Kuramoto model appears to be the optimal choice for driving a music oscillator. The use of this dynamic model resulted in higher motivational scores then earlier algorithmic approaches; most likely due to a more 'natural' feel of the musical stimuli. Hence, the Kuramoto alignment strategy was used as a starting point for these experiments.

An initial prototype with two simple alignment strategies was made, one strategy for each of the above ideas. Both used the Kuramoto model as in previous alignment strategies; but one strategy gradually shifted the music out of phase (negative, from 0° to −90°, slowdown) and the other gradually shifted the music positively out of phase (0° to 90°, slowdown).

b. Setup

We let three music-trained participants run several times with this prototype for 5 minutes. Music started after one minute, phase manipulation started after 90 seconds.

c. Conclusions

In all tests, running cadence deviated towards the hypothesized cadence (i.e., increased/decreased); whilst participants did not know in what condition they ran in. We thus concluded from this pilot that there is an influence of the relative phase to runner's cadence for our three participants; and that it is very likely that we will find this on a larger scale experiment. In our data exploration, we noticed some different responses:
>50° relative phase is noticeable for the user and he can adjust consciously in a shorter timeframe
20-50° is less noticeable, and might subconsciously influence the user over longer timeframes
Less than 20° seems not to induce any effect, i.e., a dead zone.

d. Misbehaving of the Kuramoto Model

Some issues with the Kuramoto model were also noted during previous experiments, this pilot and simulations. While these were less relevant in controlled trials, they might pose a problem in ecological settings (as is envisioned for the Proof of Concept) and therefore should be fixed. These include:
Instability of the model when SPM and target frequency differ too much
The coupling strength is tempo-independent, and thus behaves differently for high frequency (SPM) runners then low frequency runners.
'Phase cycling' behaviour of the model in some ecological situations (speedup/slowdowns)
'Indefinite' speedup/slowdowns: there is no target defined so the phase manipulation continues even if cadence is adjusted.

These observations led to the development of the modified Kuramoto model; which could be used to manipulate runners' cadence whilst counteracting the above issues with the default model.

Modified Kuramoto Model

The following modified Kuramoto model provides a usable implementation that eliminates some of these undesirable properties of the basic model. A detailed description of this model can be found in Annex II.

$$\omega_M(t) = \omega_{Target}(t) + \frac{\tilde{K}(t)}{2}\sin(\theta_H(t) - \theta_M(t)) \quad (7)$$

where $$\tilde{K}(t) = 2\alpha\tilde{\omega}_{Target}(t) \quad (8)$$

$$\tilde{\omega}_{Target}(t) = \begin{cases} \frac{\omega_H}{1-\alpha\beta}, & \omega_H < (1-\alpha\beta)\omega_0 \\ \omega_0, & (1-\alpha\beta)\omega_0 \leq \omega_H \leq (1+\alpha\beta)\omega_0 \\ \frac{\omega_H}{1+\alpha\beta}, & \omega_H \geq (1+\alpha\beta)\omega_0 \end{cases} \quad (9)$$

$$\beta = \frac{|\omega_H - \tilde{\omega}_{Target,sync}|}{\alpha\tilde{\omega}_{Target,sync}}$$

The proposed model solves the instability of the Kuramoto model when both oscillation frequencies are outside the synchronisation range. The model attempts to drive the human oscillator towards a target frequency by manipulating the music oscillator. This works assuming the human oscillator is attracted or attempts to minimize the relative phase of music & human towards 0°. This assumption can be made from earlier work (pilots, analysing individual trials of different alignment strategies, showing a certain attraction towards phase locking in the 0° region). Certain similarities can be made with the HKB model.

The model is driven by human and music oscillators, and is governed by the following parameters:

α is the synchronisation strength and range; similar to the coupling strength but proportional to the cadence. α=0.05 has a 5% synchronisation range and a K value around 1.5 at 170 SPM β controls how $\tilde{\omega}_{Target}$ will adapt to the human frequency. This results in a maximum relative phase deviation that is allowed in the model. β=0 results in a system that operates at 0° relative phase independent of the difference between target & human frequency; β=1 results in a system that can reach up to 90° or −90° relative phase when difference between target & human frequency is high. Limiting beta can decrease the amount of 'phase cycles' experienced with the unmodified model. Too small and the user will always feel in sync; too large can result in undesired behaviour (too large phase difference to be attracted towards 0°, phase cycles, etc.)

$\tilde{\omega}_{Target}$: the target frequency at which we want the model to be in perfect synchrony (0°). This value is internally rescaled to an intermediary to avoid situations where the model could misbehave.

More details about this model and its parameters can be found in Appendix II.

The task 2.3 pilot will experiment with these parameters to find a combination which works in driving a participant towards a target frequency. These optimal parameters can then be used in the Proof-of-Concept experiment for driving participants towards an optimal cadence.

Revised Proposal for the 2.3 Experiment: Determining Kuramoto Parameters for the POC Introduction In the pilot we noted several different phase correction responses to the music; based on the relative phase. This led us to three interesting 'levels' of phase shifting between music and gait; which we wanted to test further.

Subconscious or subliminal: a subtle phase shift which is not perceivable by the participant, around 30° maximum (29.4 ms at 170 BPM). We expect limited positive results (i.e., in/decreased cadences).

Barely noticeable: a phase shift which is most likely not perceivable by the participant, around 50° maximum (49.0 ms at 170 BPM). In tapping literature, 50 ms is often used as the boundary for noticing phase shifts in music; thus this could be the threshold between unnoticeable and noticeable; and hence an interesting angle to test further.

Conscious: a phase shift which should be perceivable by the participant, around 70° maximum (68.6 ms at 170 BPM). This could be perceived as annoying by some, lead to system instability or lead to increased response.

Methodology 22 participants ran 9 times: warmup, synchronization test, and 7 randomized conditions including control. All runs were around 4 minutes of self-paced running—a self selected tempo they could keep up for half an hour.

The experiment started with a general questionnaire and informed consent.

The warmup condition was without equipment and music; to familiarize with the indoor track.

The synchronization test was a test for uninstructed spontaneous synchronization. For this, we used a fixed-tempo metronome for which the tempo was matched to the mean gait frequency of seconds 40 to 60. The metronome then started playing at second 60, and ended at 4 minutes.

Each of the 7 conditions attempted to manipulate the cadence and speed of the participants using a predetermined parameter set of the Kuramoto model (i.e., music with aligned tempo and phase). Three conditions were speedup (subliminal, noticeable and conscious); three conditions were slowdown conditions and one was control (no phase shifting).

Using the modified Kuramoto model, these three levels depicted in the introduction could be approximated with the following parameters in table 1

TABLE 1

| Condition name | $\tilde{\omega}_{Target}$ (target frequency) | α (coupling) | β (maximum phase angle) |
|---|---|---|---|
| Conscious slowdown | $f_{pref} - 5\%$ | 0.05 | 0.95 (phase offset ~= 72°) |
| Barely noticeable slowdown | $f_{pref} - 5\%$ | 0.04 | 0.75 (phase offset ~= 49°) |
| Subconscious slowdown | $f_{pref} - 5\%$ | 0.03 | 0.55 (phase offset ~= 33°) |
| Control condition | $f_{pref}$ | 0.03 | 0 |
| Subconscious speedup | $f_{pref} + 5\%$ | 0.03 | 0.55 (phase offset ~= 33°) |
| Barely noticeable speedup | $f_{pref} + 5\%$ | 0.04 | 0.75 (phase offset ~= 49°) |
| Conscious speedup | $f_{pref} + 5\%$ | 0.05 | 0.95 (phase offset ~= 72°) |

The system provided music stimuli and adapted the music based on the parameters. The Beta parameter is the maximum phase angle or phase shift at which music will be played if the current cadence is 5% or more off the target tempo. The closer the cadence to the target, the smaller the relative phase becomes. If the participant runs at the desired frequency the relative phase will be 0°. This model thus uses the assumed phase correction of the participant to get to 0°.

Participants were asked to fill in a BORG (exhaustion), BMRI (music), PACES (motivation), and familiarity with music after each condition.

The music was playlist with 120 songs spread over 4 genres and BPM range of 130-200. Participants could select 2 preferred genres minimum.

Measurements during or after each trial include:
SPM before stimuli starts (mean, std and var SPM of 0:40 to 0:60)
SPM during stimuli (mean, std and var SPM of 2:00 to 3:00; midway through the song)
Velocity (mean, std and var km/h) before stimuli starts
Velocity (mean, std and var km/h) during stimuli
Mean phase angle
Resultant vector length
Survey data Preliminary Data Analysis & Exploration Data Exploration: Cadence Adjustment Table 2 summarizes how many participants increased or decreased their cadence more than a certain percentage. This is calculated by comparing the average cadence before the music starts (from 40 s to 60 s) to the average cadence halfway through the music/stimuli condition (from 120 s to 180 s); 10% outliers ignored (to ignore missed/double steps).

TABLE 2

| | Participants decreased cadence (SPM evolution <= x %) | | | Participants increased cadence (SPM evolution >= x %) | | |
|---|---|---|---|---|---|---|
| X = | -3% | -2% | -1% | +1% | +2% | +3% |
| Conscious slowdown | 18% | 27% | 59% | 5% | 5% | 0% |
| Barely noticeable slowdown | 20% | 50% | 65% | 0% | 0% | 0% |
| Subliminal slowdown | 21% | 47% | 74% | 0% | 0% | 0% |
| Control | 13% | 25% | 42% | 13% | 8% | 8% |
| Subliminal speedup | 5% | 5% | 14% | 43% | 24% | 14% |
| Barely noticeable speedup | 0% | 0% | 5% | 33% | 14% | 5% |
| Conscious speedup | 0% | 4% | 12% | 48% | 8% | 4% |
| Sync Test-Metronome | 8% | 12% | 19% | 4% | 0% | 0% |

Bold cells indicate the most effective method to obtain x % speed adjustment.

Remarks/Observations:
We notice about control & sync tests that participants had the natural tendency to slow down over time.
People generally adapt their tempo towards the desired frequency
Slowing down is easier then speeding up
The subliminal conditions, i.e., lower coupling and close to 0° relative phase, yield the most optimal results/responders.

Data Exploration: Speed/Velocity Adjustment

Table 3 summarizes how many participants speed up or slowed down more than a certain percentage. This is calculated by comparing the average cadence before the music starts (from 40 s to 60 s) to the average cadence halfway through the music/stimuli condition (from 120 s to 180 s). We note that the speed measurement is a rough estimate and only used as an indicator (i.e., it is not a verified system).

TABLE 3

| | Participants slowed down (speed evolution <= x %) | | | Participants increased speed (speed evolution >= x %) | | |
|---|---|---|---|---|---|---|
| X = | -10% | -5% | -2.5% | +2.5% | +5% | +10% |
| Conscious slowdown | 5% | 23% | 32% | 23% | 14% | 5% |
| Barely noticeable slowdown | 0% | 20% | 45% | 30% | 20% | 5% |
| Subliminal slowdown | 5% | 21% | 37% | 16% | 11% | 5% |
| Control | 4% | 13% | 38% | 38% | 13% | 0% |
| Subliminal speedup | 0% | 5% | 10% | 57% | 38% | 10% |
| Barely noticeable speedup | 0% | 14% | 29% | 19% | 10% | 5% |
| Conscious speedup | 0% | 12% | 16% | 32% | 20% | 0% |
| Sync Test-Metronome | 15% | 35% | 54% | 8% | 4% | 0% |

Bold cells indicate the most effective method to obtain x % speed adjustment.

Remarks/Observations:
The control condition is quite symmetrical in terms of people speeding up and down
The metronome seems to slow down participants
The subliminal condition, i.e., lower coupling and close to 0° relative phases, yield the most optimal results for speeding up. Slowing down in terms of velocity seems to require a bit more noticeable coupling.

Conclusions of the Data Exploration

Initial data exploration showed that the subconscious phase shift (or the 30° phase shift) worked best to influence the cadence of the participants.

Around 74% of the participants decreased their cadence 1% or more in the subliminal slowdown condition; while 43% of the participants increased their cadence 1% in the subliminal speedup condition.

Around 47% of the participants decreased their cadence 2% or more in the subliminal slowdown condition; while 24% of the participants increased their cadence 2% in the subliminal speedup condition. Note that the intended decrease or increase would be around 5%, but no participant adjusted their cadence this much.

No clear results were obtained from visual inspection of the speed (km/h).

Statistical Analysis

Statistical Analysis of Cadence

The following figures, namely FIGS. 1 to 6, show all conditions on the X-axis (sync test, slow downs, control, speed ups) as this appears to be a logical order for representing the data. The conditions marked in red are statistically different from the control condition.

The Y-axis represents the SPM/cadence difference expressed in percentage. This is calculated by comparing the average cadence before the music starts (from 45 s to 60 s) to the average cadence approximately halfway through the music/stimuli condition (from 150 s to 210 s); 10% outliers ignored (to ignore missed/double steps).

FIG. 1 shows the results for all participants combined. The 'slow down' conditions seem to average around 2% slowdown; the speedup seems to average around 1% 'speed up'. The control condition itself seems to cause a slow-down in tempo.

A repeated measures ANOVA comparing all conditions with the control condition, revealed a significant main effect of the tempo manipulation of the music on the running tempo. Contrasts revealed that all speeding-up conditions resulted in significantly higher running tempo than the control condition, and the low manipulation slow-down resulted in significantly lower running tempo than the control condition.

Figure 2:
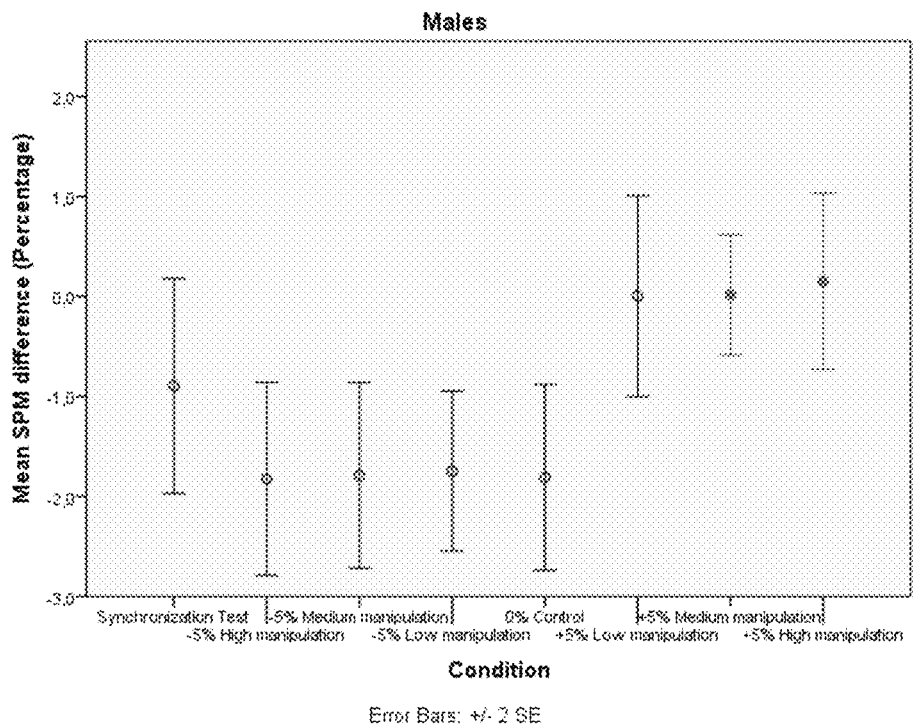
Figure 3:
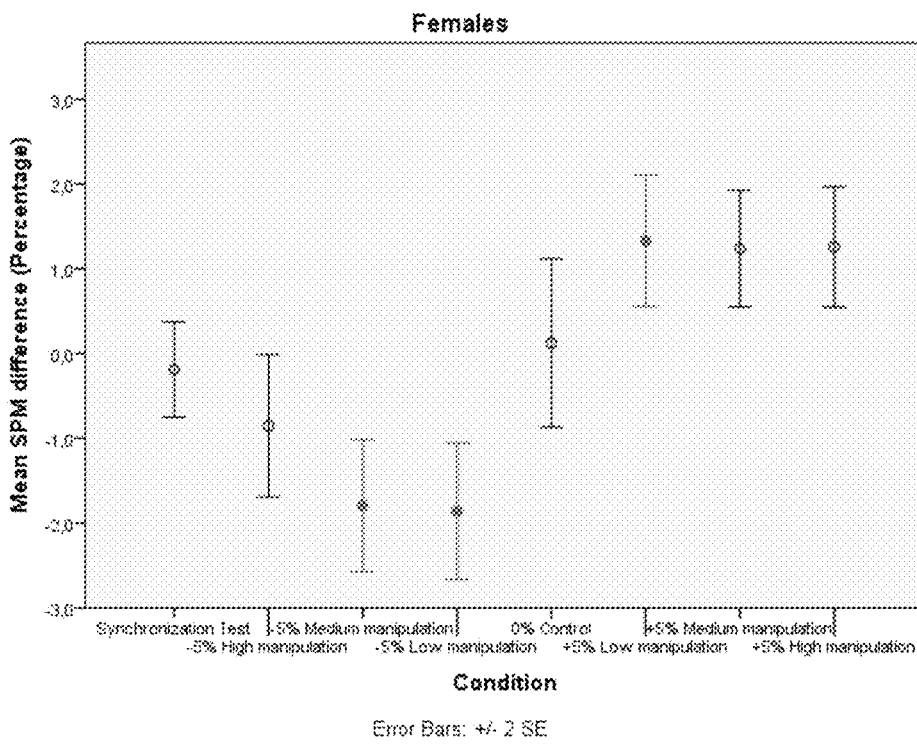

There was no significant effect of gender, indicating that running tempo for male and female participants were in general the same, see FIGS. 2 and 3 respectively.

However, there was a significant interaction effect between the target frequency manipulation conditions and the gender of the participant. Contrasts were performed comparing each of the target frequency manipulation conditions across male and female participants. These revealed that both males and females were able to speed up in some of the speeding-up conditions (marked in red in the following to plots), but only the women could be manipulated into slowing-down compared to the control condition. It seems that male participants in general slowed down during their 4-min runs, as shown by an almost −2% tempo decrease in the control condition. The slowing-down conditions had no extra slowing-down effect on top of that.

Looking at these gender differences, it seems that the slowing-down in the control condition is not an effect of the condition, but it is a result of how men are performing in these 4-min runs.

Statistical Analysis of Speed

The Y-axis represents the velocity difference expressed in percentage. This is calculated by comparing the average speed before the music starts (from 35 s to 65 s: takes 30 s to get a good mean) to the average cadence approximately halfway through the music/stimuli condition (from 150 s to 210 s).

A repeated measures ANOVA comparing all target frequency manipulation conditions with the control condition, revealed a significant main effect of the target frequency manipulation conditions on the running velocity. Contrasts revealed that the low manipulation speeding-up condition resulted in significantly higher velocity than the control condition.

Figure 4:
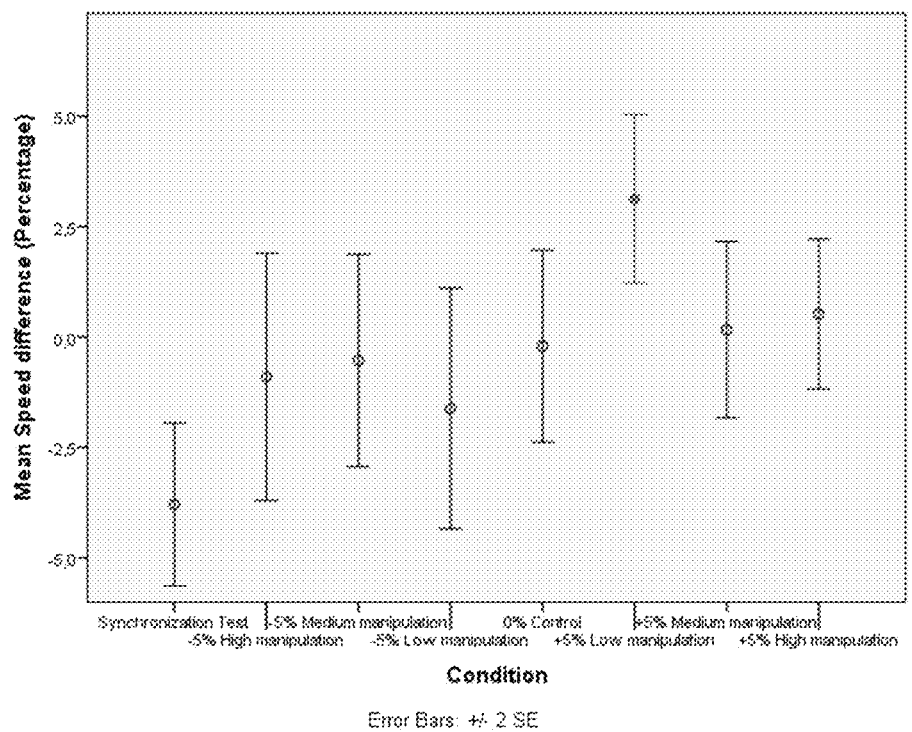
Figure 5:
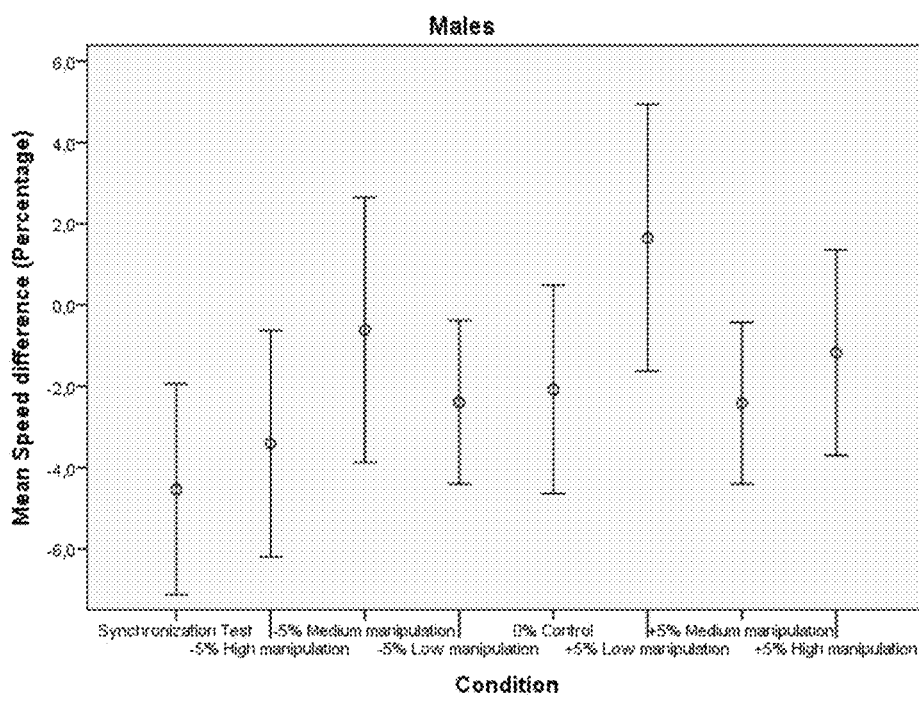
Figure 6:
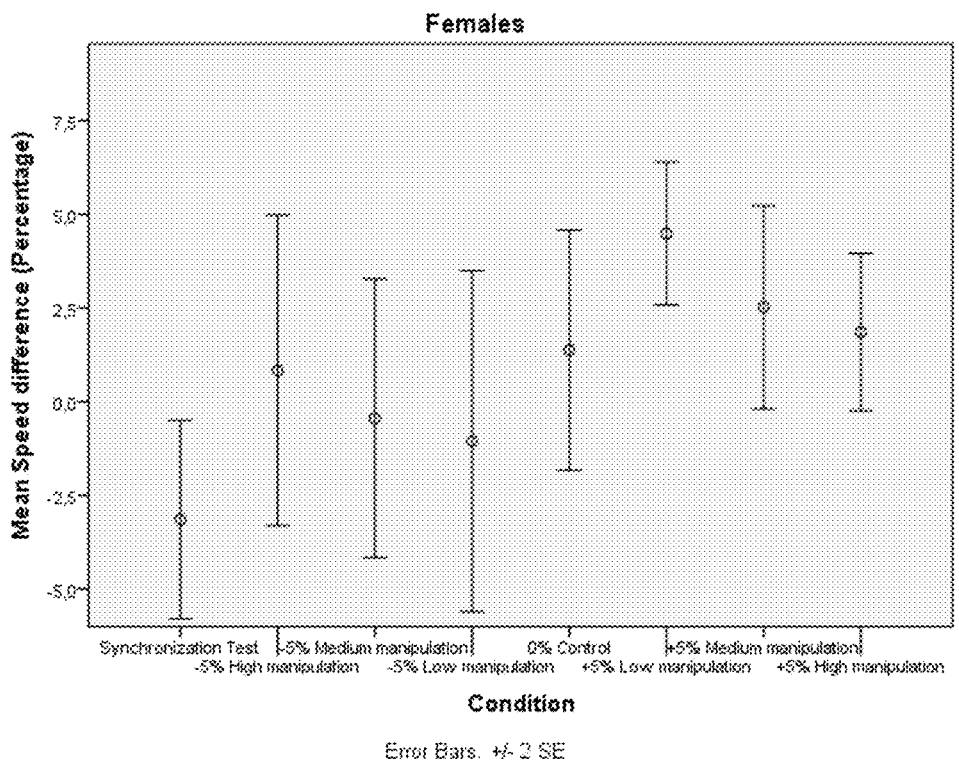

FIG. 4 also shows a big drop in velocity in the synchronization test where participants had to run to a metronome matching their running tempo.

There was no significant effect of gender and no interaction effect of the running velocity and gender. Note that splitting up the data into male and female participants only leaves 7 participants per gender group with measurements in all conditions, see FIGS. 5 and 6 respectively. Although no significant differences with the control conditions were found in the respective gender groups, the plots show some tendencies that might be shown more clearly with more participants.

Statistical Analysis of Motivation (PACES)

Comparing the Paces ratings of only the speeding-up conditions or only the slowing-down conditions did not show significant differences.

Also, no significantly different ratings were found compared to the control condition.

All target frequency manipulation conditions were rated significantly higher than the metronome condition, meaning that running to music in general was found to be more motivating than running to a metronome.

Conclusion of the Statistical Analysis

The manipulation of the music had a significant main effect on cadence (SPM) and velocity (km/h).

Contrasts revealed that all speeding-up conditions resulted in significantly higher running cadence than the control condition. Additionally, the subliminal speeding-up condition resulted in significantly higher velocity than the control condition. The subliminal slowdown condition resulted in significantly lower running cadence than the control condition, however velocity did not show any significant effects.

We note that more in depth analysis also revealed a gender effect: the reaction to the stimuli was different for males then for females. However; due to the low number of participants per group and some invalid data; the groups were relatively small to compare.

These results are similar to our data exploration: the subliminal conditions (both speed up & slow down) seem to work best to influence participants. The condition did not influence qualitative measurements such as BORG & PACES.

Conclusion

The unified/adapted Kuramoto model can be used to manipulate runner's cadence and frequency by means of a subliminal phase shift. Optimal results were obtained using a target frequency+/−5%, a coupling strength of 0.03 and a maximum phase offset of 0.55 (maximum of 33° phase shift). This resulted in a 1% increased cadence for the speedup condition and a 2% decreased cadence for the slowdown condition.

Annex II

Kuramoto Parameters and Dynamics

Minimum Background Information

Basic Kuramoto Model

In BeatHealth it is planned to use the Kuramoto model for coupled oscillators to drive music tempo modification for synchronisation to a human walker/runner. In this special case there are just two coupled oscillators (the music engine and the human) and we only have control over one of them (the music engine).

The Kuramoto equation governing the music engine is therefore:

$$\frac{d\theta_M}{dt} = \omega_0 + \frac{K}{2}\sin(\theta_H(t) - \theta_M(t)) \quad (1)$$

where $\omega_0$ is the target frequency of the model, K is the coupling constant, $\theta_M(t)$ is the phase of the music engine at time t, $\theta_H$ is the phase of the human gait at time t. This can be written as:

$$\omega_M(t) = \omega_0 + \frac{K}{2}\sin\delta(t), \quad (2)$$
$$= \omega_0 + \Delta\omega_M(t)$$
$$\delta(t) = \theta_H(t) - \theta_M(t)$$

where $\omega_M(t)$ is the instantaneous frequency of the model at time t and $\Delta\omega_M(t)$ is the frequency deviation (from $\omega_0$) at time t. This allows us to see the maximum and minimum synchronisation frequencies and the relationship to K:

$$\omega_{M,min} = \omega_0 - \Delta\omega_{max}, \omega_{M,max} = \omega_0 + \Delta\omega_{max} \quad (3)$$

$$\Delta\omega_{max} = \frac{K}{2} \Leftrightarrow K = 2\Delta\omega_{max} \quad (4)$$

Since we generally want to define $\Delta\omega_{max}$ as some fraction or percentage of $\omega_0$ then we get:

$$K = 2\alpha\omega_0 = 2\alpha\left(\frac{2\pi}{60}bpm_0\right), \alpha = \frac{\Delta\omega_{max}}{\omega_0} \quad (5)$$

where $\alpha$ is the maximum fractional frequency deviation with which we want to be able synchronise (e.g. $\alpha=0.1$ means the model can synchronize in the range $\omega_0\pm10\%$). Finally, if synchronisation is possible, $\omega_M$ will eventually equal the human (step) frequency $\omega_H$ so that from (2) and (4) we get the stable phase difference between the music engine and human, $\delta_{sync}$:

$$\delta_{sync} = \sin^{-1}\left[\frac{2}{K}(\omega_H - \omega_0)\right] = \sin^1\left[\frac{\omega_H - \omega_0}{\Delta\omega_{max}}\right] \quad (6)$$

Modified Kuramoto Model

The modified Kuramoto model is required to provide a usable implementation that eliminates some undesirable properties of the basic model (as described in section 0). Specifically the target frequency needs to be adapted over-time (and as a consequence, K, which should vary with target frequency, should also be adapted).

Therefore, we propose modifying (1) to give the following:

$$\omega_M(t) = \tilde{\omega}_{Target}(t) + \frac{\tilde{K}(t)}{2}\sin(\theta_H(t) - \theta_M(t)) \quad (7)$$

where $$\tilde{K}(t) = 2\alpha\omega_{Target}(t) \quad (8)$$

In (9), $\omega H$ is the estimated human step rate and (based on the work in Gent) this will be a smoothed version of the measured step rate.

The parameter $\beta$ controls how $\tilde{\omega}_{Target}$ will adapt to the human frequency, $\omega H$, and useful values range from 0, continuously equaling $\omega_H$, to 1 where $\tilde{\omega}_{Target}$ only adapts if $\omega_H$ exits the preferred frequency synchronisation range (i.e. $(1\pm\alpha)\omega_0$). Between these values, $\beta$ determines the maximum difference between the human tempo and model's target frequency as a fraction of the model's frequency synchronisation range.

From (6), (8), and (9), it can be shown that $\beta$ also controls the stable phase difference at synchronisation when $\tilde{\omega}_{Target}\neq\omega_0$ $$\delta_{sync} = \sin^{-1}\left[\frac{\omega_H - \omega_{Target,sync}}{\alpha\omega_{Target,sync}}\right] \quad (10)$$

$$= \begin{cases} \sin^{-1}[\beta], & \omega_H > (1+\alpha\beta)\omega_0 \\ \sin^{-1}[-\beta], & \omega_H < (1-\alpha\beta)\omega_0 \\ \sin^{-1}[\omega_H - \omega_0/\Delta\omega_{max}], & \text{otherwise} \end{cases}$$

Finally, to ensure that excessive tempo modification is avoided, even if a large value of $\alpha$ (and hence K) is chosen, we propose clamping the frequency output of the model in (6), such that:

$$\omega_{M,clamp} = \max((1-\gamma)\omega_{song}, \min((1+\gamma)\omega_{song}, \omega_M)) \quad (11)$$

where $\gamma$ defines the maximum and minimum frequencies that the model can use as a fraction of the unmodified song frequency, $\omega_{song}$. We are considering recommending that $\gamma$ is set to 0.2 which means that the tempo of a song will never be modified by more than $\pm20\%$.

Key Findings

We make the following parameter recommendations based on the findings below:
  Do not set K independently, instead set $\alpha$ so that the model can adapt to a wide range of BPMs
  Set $\alpha$ between 0.1 and 0.15 (which implies K between 1.68-2.51 at 80 BPM and between 3.77-5.65 at 180 BPM)
  If we want to follow the human tempo like Gent Strategy 4, Set $\beta=0$
  Otherwise, if we want to drive the human towards some target frequency, set $\beta$ between 0.5 and 0.7071. This implies $\delta_{sync}$ would range from 0 at the target frequency to between $\pm30$ and $\pm45$ degrees when too far away from the target frequency while still giving room for the model to handle step to step variation. [These values of $\beta$ or slightly higher/lower values could be validated experimentally]
  Choose the amount of smoothing applied to the $\omega_H$ estimate such that the model responds quickly enough to large perturbations (or run a separate, less smooth estimate specifically to detect short time scale perturbations)

Figure 7:
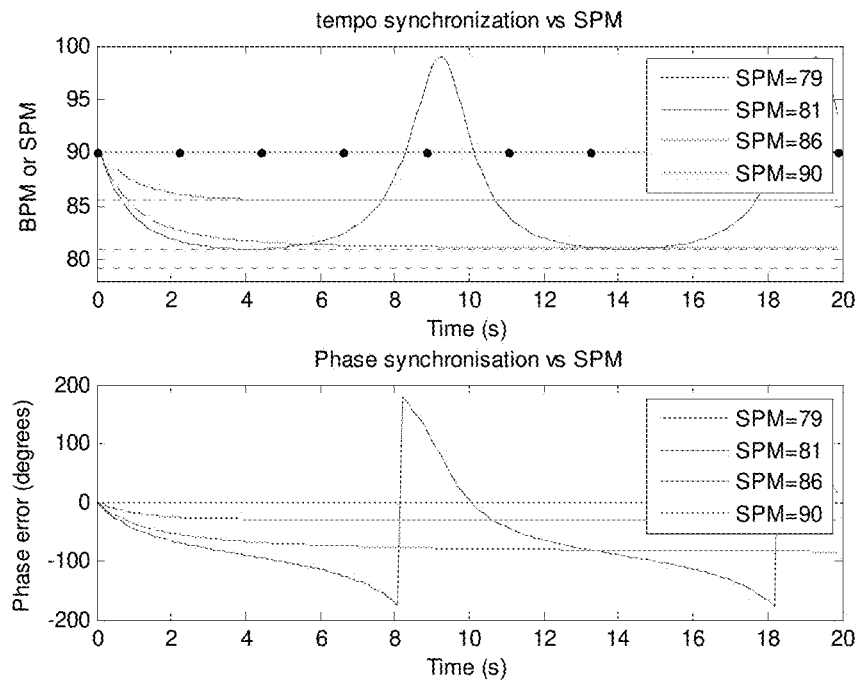
Figure 8:
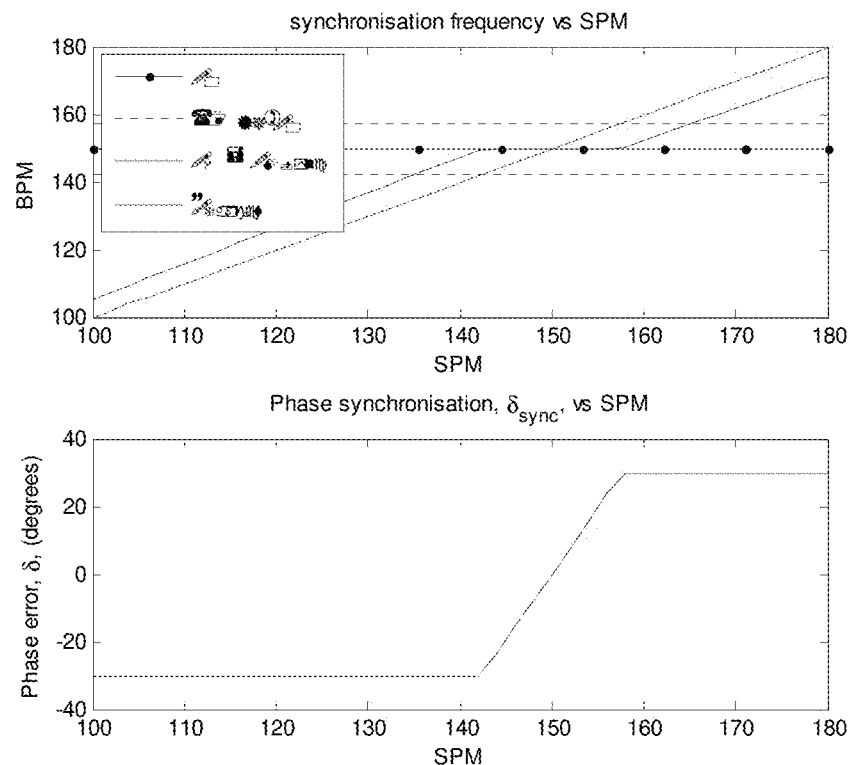
Figure 9:
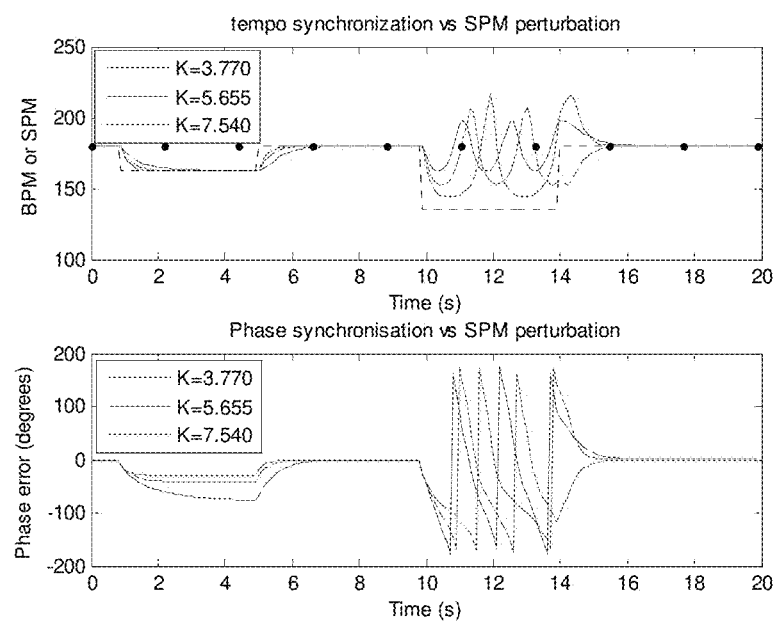
Figure 10:
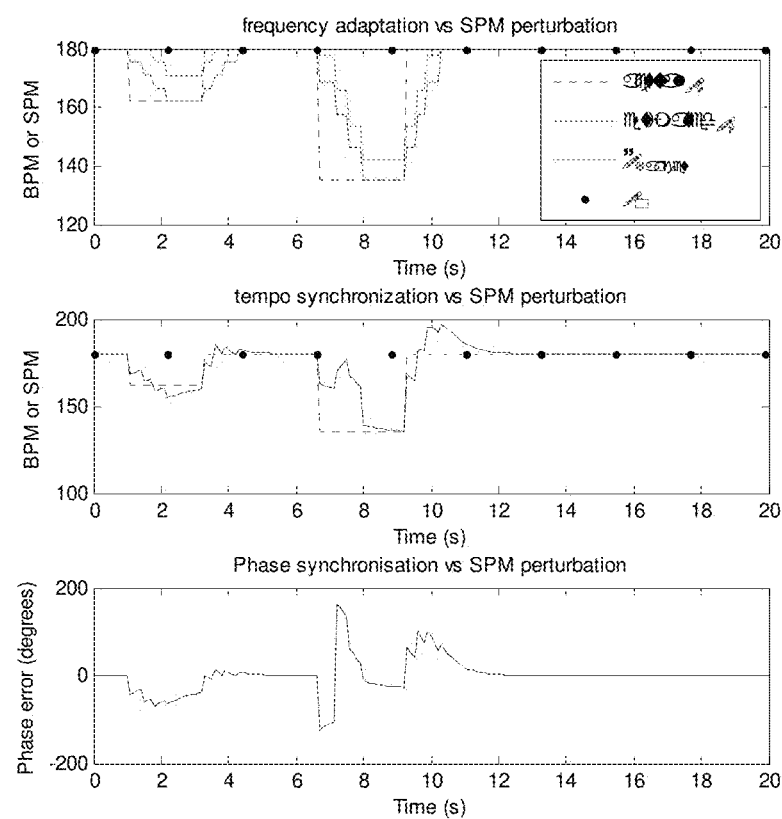

The key findings relating to the Kuramoto parameters and dynamics are as follows:
  1. The Kuramoto model has a hard limit on the minimum and maximum frequencies with which it can synchronise for a given value of K and $\omega_0$ or $W_{Target}$. Exceeding these limits, even slightly, causes the model (and hence the music tempo) to oscillate undesirably between its minimum and maximum frequencies (see FIG. 7: The response of the Kuramoto model (target frequency=90 BPM, $\alpha=0.1$) to various input SPMs, all starting from an initial phase error of 0. Within the synchronization range of the model the BPM converges on the SPM and the synchronised phase error depends on the required frequency deviation from preferred. With an SPM just outside the synchronization range (blue line) the model BPM oscillates and the phase error does not converge.). It may not happen often, but in an ecological context and with no target frequency adaption (or adaption that is too slow) it can be expected occasionally.
    Recommendation: If no target frequency adaption will be used, choose $\omega_0$ and $\alpha$ (and hence K) so that the frequency limits are difficult for the human to exceed.
    Recommendation: Preferably, adapt $\omega_{Target}$ as necessary (see FIG. 8: The synchronisation behaviour of the modified Kuramoto model with $\omega0=150$ BPM, $\alpha=0.1$, and $\beta=0.5$. Note how it can synchronise across the entire SPM range, but sets the phase to "encourage" the human SPM towards the preferred frequency, $\omega0$, at which point the phase error reduces to zero.). Choose $\beta$ to place limits on $\delta_{sync}$ and choose $\alpha$ to provide enough frequency synchronisation range so that normal gait frequency changes do not exceed the limits (but see point 2 below).
  2. Human gait tempo, $\omega_H$, can change suddenly in an ecological context (e.g. due to an obstacle on the path). Changes which exceed the model frequency limits more quickly than $\omega_{Target}$ can be adapted will cause the Kuramoto model to behave badly (see FIG. 9: The response of the Kuramoto model to short (4 second) perturbations of the "human" tempo (dotted line) at 1 and 10 seconds. The perturbation at t=1 second is within the model's synchronisation frequency range. The perturbation at t=10 seconds is outside the model's synchronisation frequency range and causes the music tempo to oscillate undesirably between minimum and maximum values). Although these are artificial perturbations, it may be difficult to adapt $\omega_{Target}$ quickly enough for short term events without making the model too "twitchy". (See FIG. 10 which includes adaptation but is still not fast enough. The response of the modified Kuramoto model to the same perturbations as in FIG. 3. Note that the less smooth tempo and phase in this figure is related to the real time phase estimation and unrelated to adaptation process. The adaptation process removes the later tempo oscillations but still allows some through while it is "catching up" with the perturbation.)

Recommendation: To detect these transients it may be necessary to maintain a less smooth estimate of $\omega_H$ which would need careful tuning. If this less smooth $\omega_H$ exceeded the model synchronization range, it may be appropriate to disconnect the model output temporarily so that BPM continues at its last valid value. There would be a temporary loss of phase synchronization (which would happen anyway) but it avoids music BPM oscillation. If the situation persists, $\omega_{Target}$ adaptation will eventually catch up so that the SPM is back in synchronization range and the model output can be connected again.

Figure 11:
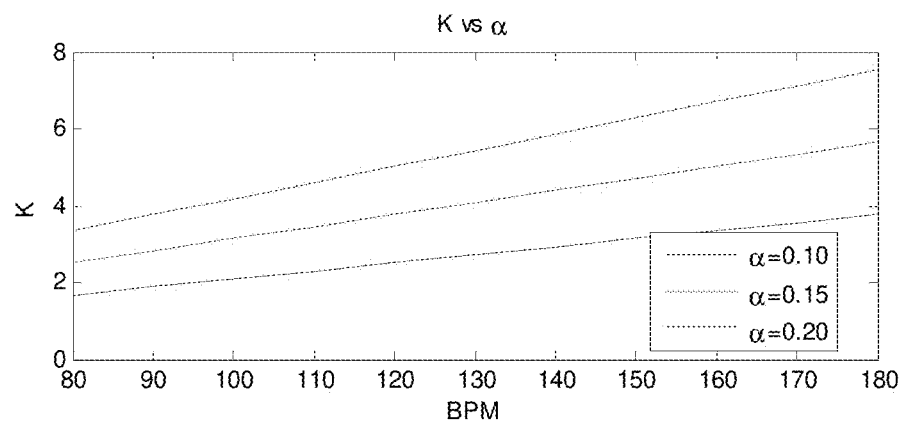

3. We assume that we will usually want to maintain a constant value of a across the operating range (e.g. if the frequency limits of the model should be ±10% of the target frequency). In this case, the appropriate value of K depends on the preferred SPM and the value of K for runners will be about twice as large as that that for walkers (see FIG. 11: The relationship between K and $\omega 0$ (in BPM) required to maintain a constant maximum percentage frequency deviation, a).

4. The constant phase difference, $\delta_{sync}$, that will be present when the music has been "synchronised" to the human depends on the difference between the human frequency and target frequency divided by the maximum frequency deviation, $\alpha\tilde{\omega}_{target}$. At the synchronisation limits, $(1\pm\alpha)\omega_{target}$, this phase difference will be 90° (corresponding to a very audible and perhaps undesirable time difference of 167 ms at 90 SPM). Halfway between the target frequency and the frequency synchronisation limits, $\delta_{sync}$ reduces to 30°. If target frequency adaption is being used, then β explicitly controls the value of $\delta_{sync}$ (see equation (10))

Figure 12:
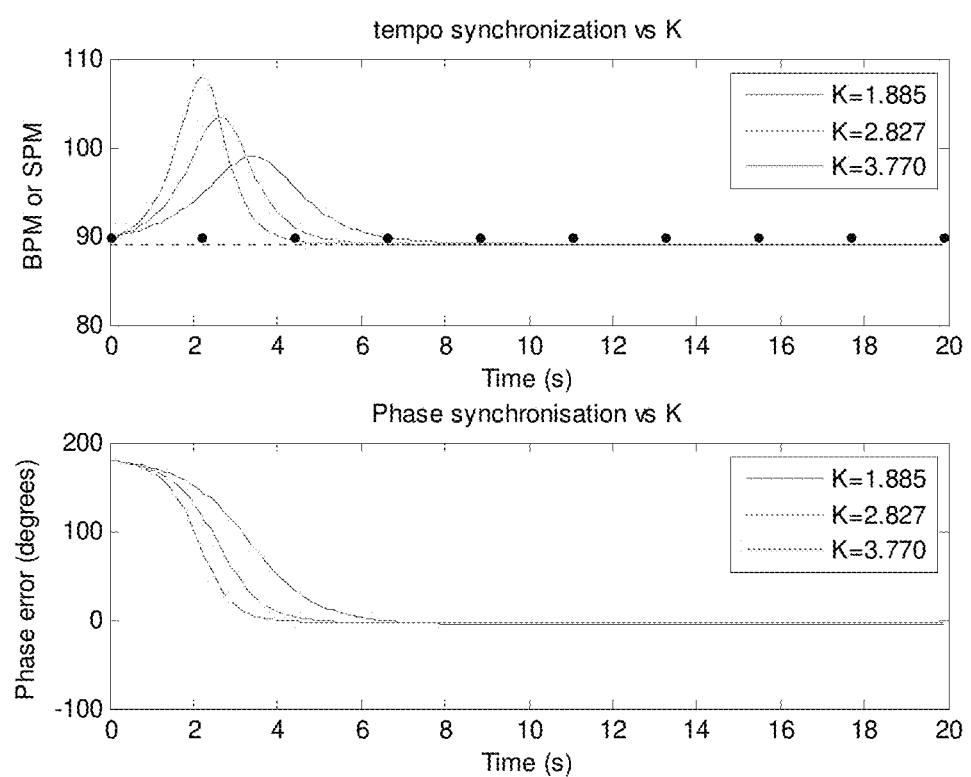

Recommendation: Choose α to control the responsiveness of the model and choose β (which controls $\omega_{Target}$ adaptation) to avoid excessively large values of $\delta_{sync}$ 5. α (and hence K) also determines the maximum tempo increase/decrease that the music engine will temporarily apply while trying to synchronise (see FIG. 12: The dynamics of synchronising to a human at the preferred tempo of the model but initially 180 degrees out of phase. K affects both the synchronisation time of the model and the maximum frequency deviation employed during synchronisation. Larger K implies larger frequency deviation but quicker synchronisation.). Since tempo increases or decreases of more than 10% start to degrade and more than 20% should be avoided, this places an upper limit on the value of K that may be chosen for any $\omega_0$.

Figure 13:
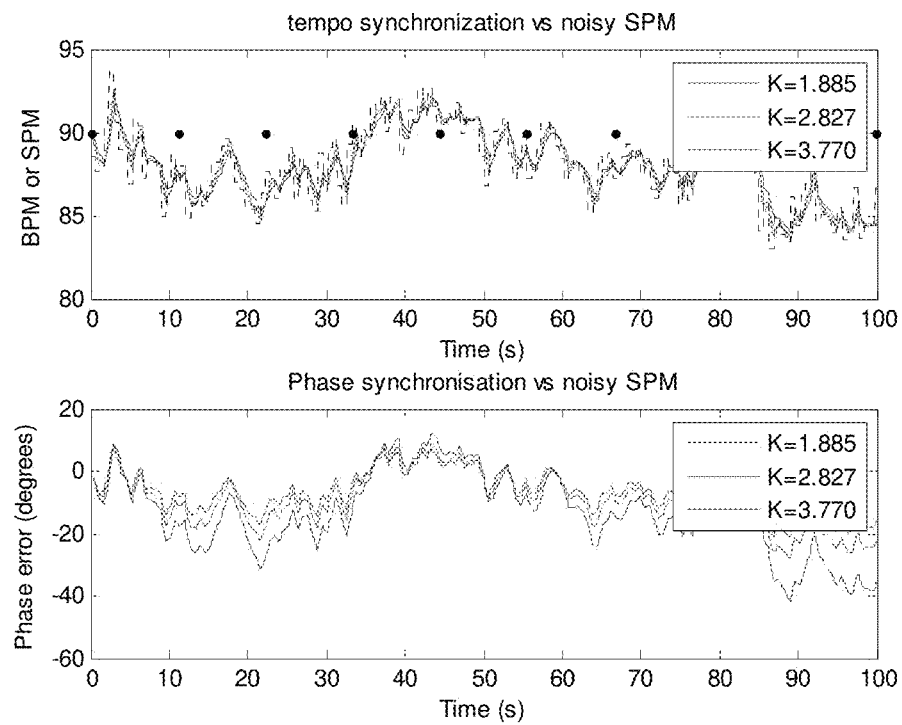

Recommendation: preferably choose α less than 0.2 (i.e. 20%). If not possible then choose γ=0.2 to prevent tempo modifications larger than ±20%. 6. The value of a (and hence K) affects the dynamics of the model and how well it can synchronise with noisy/variable human gait (see FIG. 13: The response of the model to low level noise and variability. The "human" input (dotted black line) was 90 SPM with added pink noise (SD step interval=20 ms). The preferred tempo of the model was also 90 BPM. The K values correspond to maximum frequency deviations of 10%, 15%, and 20% respectively at this preferred tempo.). The choice of a (and hence K) does not seem to have a dramatic effect here but the response is a bit worse for small α.

Recommendation: choose α around 0.15—the response seems a bit worse with α=0.1

Part-3-Project-610633_Deliverable-4.2: Sensors and Protocols Description;

Deliverable Description

Deliverable D4.2, "physiological sensor integration" focuses on the integration of a suitable suite of sensors into the BeatHealth mobile application platform. In Task 4.1 it was decided that the BeatHealth mobile application would be Android based. Therefore Task 4.2 and deliverable D4.2 are primarily concerned with integrating sensors that are compatible with mobile devices using the Android operating system.

Laboratory prototypes developed in WP3 (Task 3.3) for experiments run in WP2 initially used iPods as their inertial sensors (as DJogger had used previously). However, using the same sensors as the mobile platform would make it more likely that the results from the WP2 experiments would translate directly to the mobile platform implementation in WP4. Therefore it was desirable to ensure that the same sensors were used in both the laboratory prototypes and the mobile platform where possible. This desire also affected the selection of sensors and sensor technologies.

The remainder of this document is organized as follows. First we provide some insight into the selection of the sensor technologies and devices for BeatHealth. Next we describe the implementation of custom sensors designed specifically for BeatHealth. Thereafter we examine sensor data acquisition (Subtask 4.2.2 in WP4) and feature extraction (Subtask 4.2.3) in detail. Finally we report the status of development in D4.2 and give some indication of future work to be performed.

Sensor Solutions for BeatHealth

Sensor Requirements

Early discussions between partners identified the need for three primary sensing modalities: kinematic (primarily gait-related) sensing, heart rate sensing, and respiration sensing. Of these, we noted that the kinematic and heart rate sensing would likely be part of a final end-user BeatRun system whereas respiration sensing was more likely to be part of the laboratory prototypes but might not often be used by end-users because respiration sensors are often too inconvenient to be used by end-users.

For Parkinson's Disease (PD) patients using BeatPark, kinematic sensing appeared to be the most important modality. In contrast to BeatRun, interest was expressed in additionally measuring non-gait related movements of clinical relevance, perhaps related to specific exercises. Although details of this have not yet been formalized in a user story, the general idea was to move the kinematic sensor to another location on the body to facilitate alternative measurements. Additionally user stories (requirements) have been proposed which indicate that clinicians would have an interest in measuring both respiration rate and heart rate while patients are using the BeatPark app.

It was agreed that kinematic sensing would be achieved by inertial sensors. UGent/WP3 specifically indicated that their prior algorithms should work with a 3-axis accelerometer (5 g scale) mounted at the ankle or hip and/or a 3 axis gyrometer mounted at the upper or lower leg. In either case, existing UGent algorithms required sensors to sample and stream data at a rate of at least 100 samples per second in real time.

Other possibilities discussed include pressure sensors in sole of the shoe and sensors which send just one notification per step rather than streaming the raw inertial samples. These possibilities have not been investigated further at this time due to some impracticality mounting sensors in the shoes and concern regarding communication latency for sensors that just send only one notification per step.

CHRU also noted that the gait of PD patients can become very flat in the saggital plane, sometimes sliding their feet along the ground. For this reason we currently believe (but have not yet received confirmation) that PD patients will require gait sensors worn on the leg/ankle and that sensing at the hip may be insufficient for this user population.

The requirements for heart rate and respiration sensing were simply that both rates could be recorded over time (for example the duration of a run). No specific sample rates were mentioned, but commercial heart rate sensors will usually provide heart rate updates at intervals of one or more seconds.

Compatible Communication Technologies

The principal communication technologies compatible with Android mobile devices are WiFi, Bluetooth 2.1, Bluetooth 4, and ANT+. All of these technologies operate using the 2.4 GHz ISM band. We considered the advantages and disadvantages of each:

WiFi: The power consumption of WiFi is higher than other technologies listed so it is not typically used for low power (small and lightweight) sensors. Furthermore WiFi connectivity usually relies on access to a WiFi router making it less suitable for outdoor exercise (although WiFi direct can provide a solution when out of WiFi network range for mobile devices which support it). There are two main choices for communication over WiFi. TCP provides a reliable transport at the expense of non-real time behavior when packets must be retransmitted. In contrast, UDP provides no reliability guarantees (that is, some data may be lost) but it is frequently used for real time data streaming where it is better to maintain timing than wait for retransmissions.

Bluetooth 2.1 (also known as Bluetooth Classic): Bluetooth 2.1 is a well established protocol that is widely supported on most mobile devices. It is a short range communications scheme—the most common class 2 devices have a communication range of approximately 10 m. The most commonly used transport protocol is RFCOMM which is a reliable transport that emulates a standard serial port at a fixed rate with a theoretical maximum data rate of 720 kbps (but 450-500 kbps in practical use).

Bluetooth 4 (also known as Bluetooth Smart): Bluetooth 4 is an enhanced version of Bluetooth, standardized in 2010. Bluetooth Low Energy (BLE) is a subset of Bluetooth 4 that is particularly optimized for low energy applications such as sensing and this is this variant that we will focus on in the remainder of this document. Support for Bluetooth 4 was added in Android 4.3 and it is also supported in iOS (iPhone), Mac OS X, Linux, and Windows 8.

The main advantage of BLE for BeatHealth is that it permits much lower power communication than Bluetooth 2.1 so that sensors may be smaller (due to a smaller battery) and yet operate for longer. A potential disadvantage is that the Generic Attribute (GATT) profile that is required for low power communications limits the maximum size packet that can be transmitted and limits the data rate that can be achieved. The highest data rates of up to 60 kbps(Gomez, Olle, & Paradells, 2012) required for real time inertial streaming are achieved with GATT notifications but, like UDP over WiFi, some notifications can be lost.

Bluetooth 4 also defines a Health Device Profile, used by a number of fitness and medical devices, such as the Polar H7 Heart Rate Monitor (see section 0). It defines formats for a number of common attributes such as blood glucose, blood pressure, and pulse oximeter values. However this profile is oriented at specified set of health device types and has limited flexibility. For the devices that do support it, it provides a single straightforward interface to retrieve frequently used vital statistics.

ANT: ANT+ is an interoperability enhancement of the ANT protocol, an open access multicast wireless technology designed specifically for sensors focusing on sport and wellness, in addition to home automation and control. It can be seen as competitor to BLE, however it is currently only supported by a limited set of Android devices: specifically devices from Samsung, Sony, and one HTC device. For this reason we decided not to pursue this technology further.

Of the technologies listed, Bluetooth 4 was considered to be the most appropriate choice for sensors used by the BeatHealth mobile platform. As many commercially available sensors still use Bluetooth 2 technology it is important that the mobile platform shall also support Bluetooth 2 devices.

DJogger Solution

The DJogger system which precedes BeatHealth is based around a Windows PC running a custom app implemented in Cycling 74's Max/MSP audio processing framework. Inertial sensing for gait detection is provided by two iPod Touch devices strapped to the ankles of a runner. The iPods run a third party app, Sensor Monitor Pro by Young-woo Ko. This app samples the iPod internal accelerometers and gyrometers at rate of around 100 samples per second (see section 0 for more details). The app also streams the sample data to the Windows PC using UDP over WiFi.

While this setup works well in a laboratory environment, the iPods make rather expensive inertial sensors and WiFi may not be the best communication technology for sensors.

Current Commercially Available Sensors and Review

We reviewed the specifications for a number of commercially available sensors.

The iRhythm Zio (iRhythm Technologies Inc., 2014): at the time of investigation this sensor did not appear to support streaming and therefore did not lend itself to the real time signal acquisition required The Zen (renamed Lumafit) sensor by Zinc Software (Zinc Software, 2014): this device is worn at the ear, measures heart rate, and incorporates an accelerometer. It is potentially interesting to BeatHealth and indeed we held some discussions with the company to get early access to a prototype device. However the device has been held back by multiple production delays and is still not commercially available at the time of writing. Once it is available we are keen to test and evaluate its capabilities.

The IMEC ECG Patch: We have not been able to get access to a device from this supplier and again there appears to be issues with realtime connecting for streaming and the availability of an Android SDK. The current status of this technology is described in a recent press release from the company (Imec, 2014).

Polar H series heart rate sensors (Polar Electro, 2014): These sensors are potentially the most practical so far and we envisage using these once the heart rate feature development commences.

We also obtained two further sensors for test and evaluation.

The MetaWatch WDS112 is a smartwatch released in 2012 that incorporates an accelerometer and communicates over Bluetooth 2 RFCOMM using a custom message format. The accelerometer is sampled at 50 samples per second and 12 bit resolution, but truncated to 8 bit resolution for transmission.

The Zephyr H×M is a heart rate monitor that includes inertial sensing (although this is not explicit in the specifications) and communicates over Bluetooth 2 RFCOMM using a custom message format. One data message is transmitted each second containing the heart rate, the last 15 heart beat timestamps, the instantaneous speed, the distance covered, and the number of strides taken.

Of the inertial sensors listed, none appear suitable for attaching at the foot or lower leg which is the sensor location for which pre-existing DJogger algorithms have been designed. Moreover the DJogger algorithms are designed to work with an inertial sensor that can stream samples at around 100 samples per second and again, none of the inertial sensors met this requirement.

We expect to select and integrate support for heart rate sensors later in the project based on the results and needs of scientific activities in WP2.

Android Device Internal Sensors

Android phones normally contain a number of built in internal sensors which are relevant to BeatHealth:

An accelerometer is required for Android certification and compatibility. However there are no specific requirements for the resolution or sampling rate. We have observed sample rates from 12 samples per second to 100 samples per second depending on phone model. Internal accelerometers with low sample rates will not be suitable for BeatHealth kinematic sensing.

A gyroscope is optional and typically only present in mid to high end phones. Where present, a suitable gyroscope can improve the quality of kinematic sensing available for BeatHealth.

A GPS receiver is optional but rarely absent. The GPS is an integral part of walk and run tracking in typical exercise apps and therefore expected to be used in the BeatRun app.

A heart rate sensor (using LEDs and photosensors) has been included in some recent phones but the method of use (placing a finger over a sensor on the phone) makes it generally unsuitable for measurement while exercising.

Although using sensors already embedded in a phone is attractive for BeatHealth we determined that the mobile app could not depend exclusively on internal sensors in the short term. In the longer term we plan to evaluate the capabilities of internal sensors more completely and determine whether new or modified algorithms can be used to overcome the variable timing (see section 0) and issues surrounding the variety of placements on the body typically used by runners. We also plan to investigate sensor fusion techniques for combining readings from internal and external sensors to provide better quality processed signals.

Conclusion

In summary then, no commercial inertial sensor that we evaluated offers the required data streaming rate. Many phone-internal sensors also fall short of the required streaming rate and internal sensors do not (easily) allow sensor placement on the foot/ankle (as may be required for BeatPark and desirable for BeatRun). As a consequence we agreed to design and build our own sensors, for now at least.

BeatHealth Custom Sensors

Figure 14:
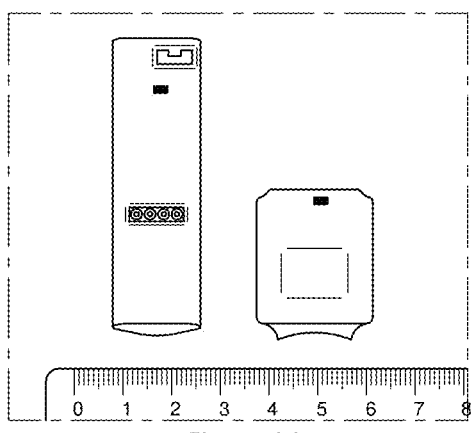

Two families of inertial sensors were developed. The BeatHealth IM4 family uses Bluetooth 4 (BLE) communications and is powered by a coin cell battery such that the entire package is easily small and light enough to attach to shoelaces if desired as shown in FIG. 14 (Top view showing indication LED (IM2 sensor on the left, IM4 sensor on the right)) and FIG. 15 (Bottom view showing batteries (IM2 sensor on the left, IM4 sensor on the right).

Figure 15:
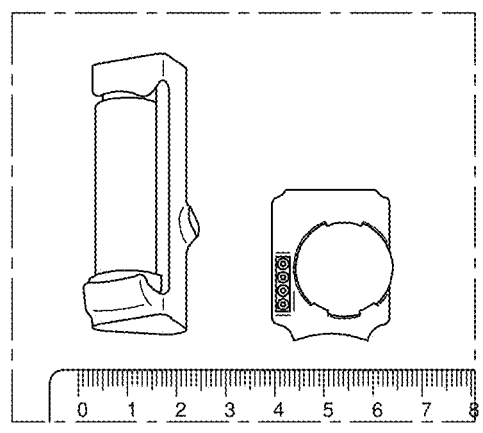

The BeatHealth IM2 family uses Bluetooth 2.1 communications and is powered by an AAA (or AA) battery so that it can provide reasonable operating time despite the higher power consumption of Bluetooth 2.1 devices. The device is still relatively small and the physical package is dominated by the battery as shown in FIG. 15.

Bluetooth 4 Sensors

Figure 16:
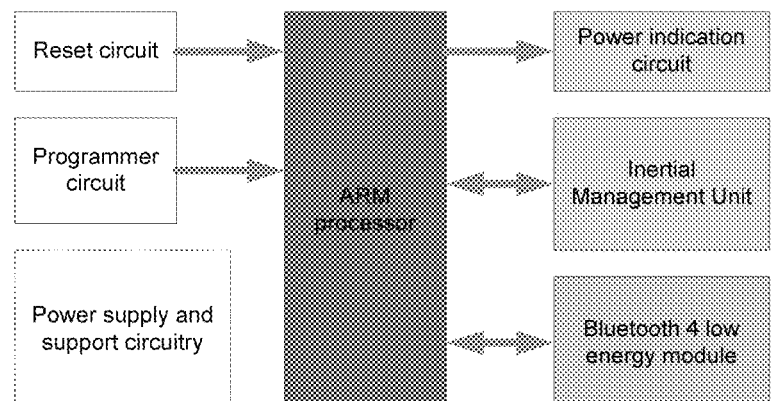
Figure 17:
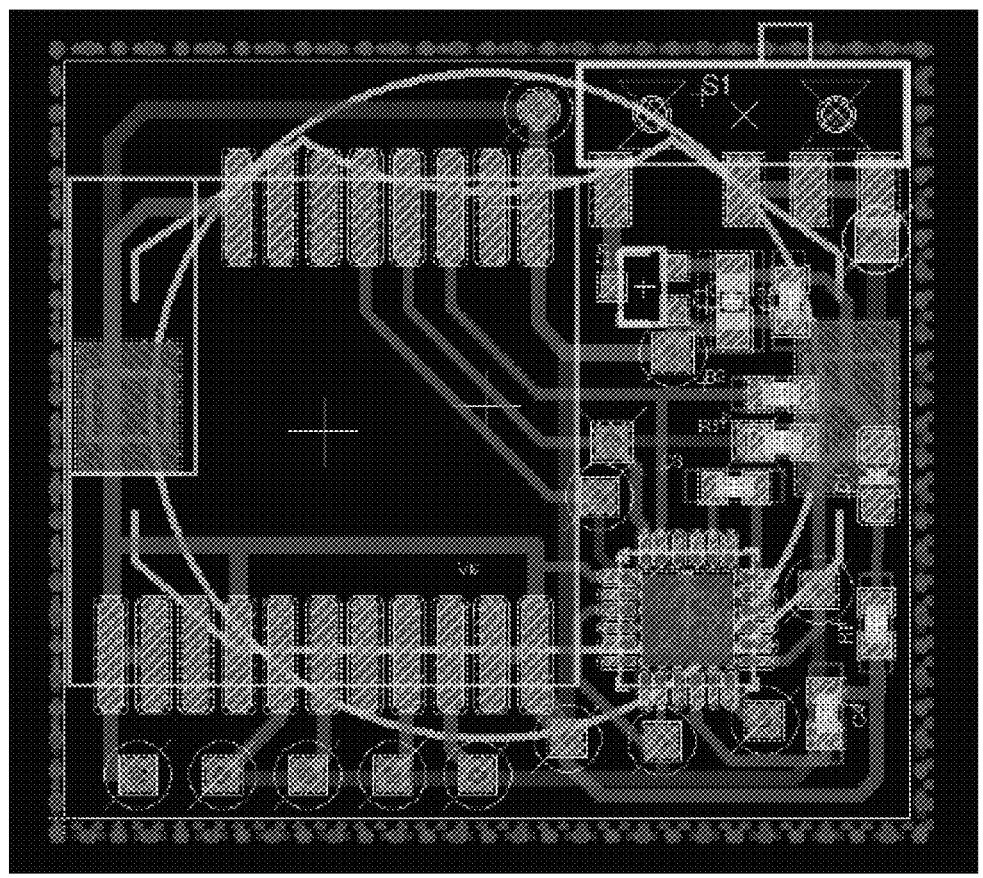

At the high level, the IM4 sensors all follow the same basic design, comprising an ARM Cortex microcontroller, inertial management unit, Bluetooth 4 low energy radio module, and support circuitry as shown in FIGS. 16 (high level block diagram) and 17 (printed circuit layout).

Several variants of the IM4 sensor were developed. These differed in the choice of inertial management unit and Bluetooth module used as listed in Table 4.

TABLE 4

BeatHealth IM4 sensor variants

| Sensor name | Engineering code | Components and features |
| --- | --- | --- |
| IM4-130 | 2RFD84 | RFDuino integrated Bluetooth 4 module (transmission up to 10 m), 3-axis accelerometer (±8 g), CR2032 coin cell power source (up to 7 hours operation) |
| IM4-160 | 3RFD60 | RFDuino integrated Bluetooth 4 module (transmission up to 10 m), 3-axis accelerometer (±8 g), 3-axis gyronneter (±1000°/sec), CR2032 coin cell power source (up to 5.5 hours operation) |
| IM4-230 | 1H1184 | HM11 Bluetooth 4 module (transmission up to 10 m), 3-axis accelerometer (±8 g), CR2032 coin cell power source (up to 5.5 hours operation) |
| IM4-260 | 4H1160 | HM11 Bluetooth 4 module (transmission up to 10 m), 3-axis accelerometer (±8 g), 3-axis gyronneter (±1000°/sec), CR2032 coin cell power source (up to 5.5 hours operation) |

All IM4 family sensors communicate using the Bluetooth 4 GATT profile. Messages are of fixed size and contain 12 bytes of binary data comprising a message number (1 byte), microseconds timestamp (4 bytes), accelerometer x, y, and z (each 2 bytes), and the battery voltage (1 byte).

Bluetooth 2.1 Sensors

Although we believe Bluetooth 4 sensors are the most appropriate choice for BeatHealth because they are designed for low energy consumption, we also developed Bluetooth 2.1 sensor. These were developed both for comparison purposes (yielding interesting results in the timing investigation detailed later in this document) and to facilitate integration with the laboratory prototypes developed by WP2. (In WP2, UGent experienced some problems between Windows 8.1 and the MAX/MSP framework used for the laboratory prototypes and this ultimately led them to revert back to Windows 8 and to seek an alternative to the Bluetooth 4 sensors.)

Figure 18:
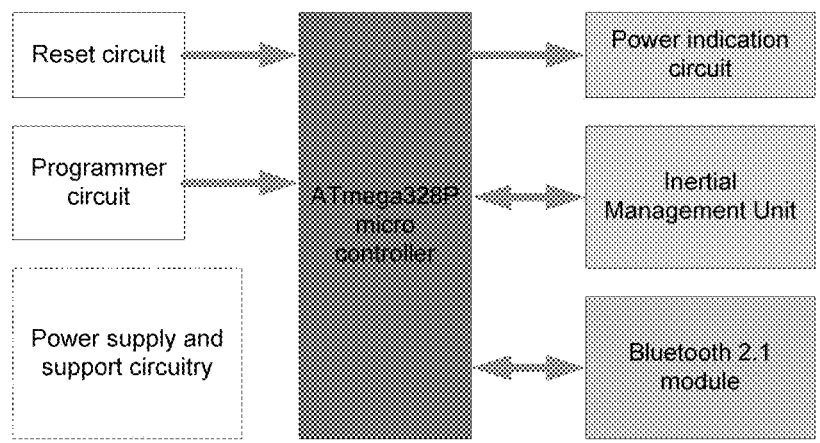
Figure 19:
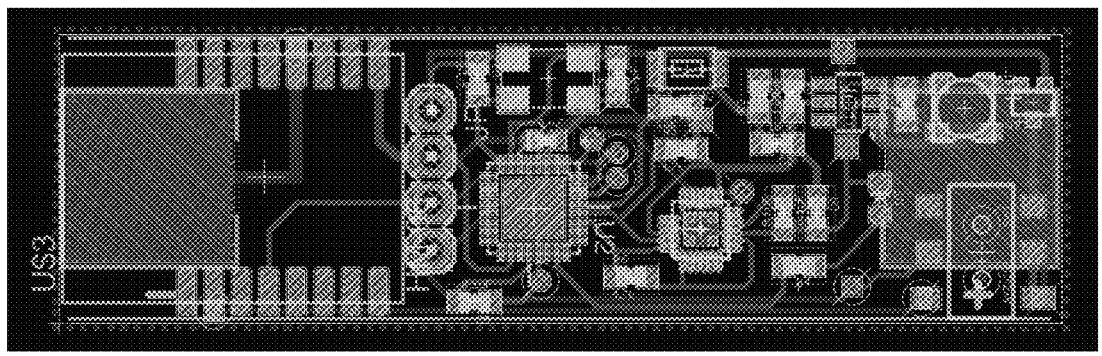

The high level block diagram of the IM2 sensors is broadly similar to the IM4 sensors as shown in FIGS. 18 (high level block diagram) and 19 (printed circuit layout). Although it is not obvious from the figure this was a new design and much of the low level circuit implementation differs from the IM4 sensors. In particular, the initial Bluetooth 2.1 sensors used the same coin cell power source as the Bluetooth 4 sensors, but operation time was unacceptably low (less than 1 hour). The circuit board was redesigned to take an AA or AAA battery and voltage conversion circuitry was added to step up from the 1.5 V supplied by the battery to the level required by the sensor hardware.

Unlike the IM4 sensor family, just one basic IM2 sensor variant was created though several instances of this sensor were fabricated. The only minor difference between instances was the battery used as indicated in Table 5.

TABLE 5

BeatHealth IM2 sensor variant

| Sensor name | Engineering code | Components and features |
| --- | --- | --- |
| IM2-190 | 5H0692, 6H0692, 7H0692 | HM06 Bluetooth 2.1 module (transmission up to 10 m), 3-axis accelerometer (±8 g), 3-axis gyronneter (±1000°/sec), and 3-axis magnetometer, AAA alkaline battery (up to 7.5 hours operation) |
| IM2-191 | 8H0692 | Same as IM2-190 except for AA alkaline battery (up to 15 hours operation) |

The IM2 sensors communicate using the Bluetooth 2.1 RFCOMM protocol. To simplify integration of the IM2 sensors into the laboratory prototypes developed by WP3 we designed the sensors to send data in readable text format. While this accelerates the debugging and testing process, the disadvantage of this is that messages are much longer (that is, more data must be transmitted for each sample). In the future, for final tested prototypes, it is possible to modify the communication to use a binary message format which should yield a substantial data reduction.
For now, messages are of fixed size and contain 72 bytes of ASCII formatted text comprising the following: a message number (3 bytes), a microseconds timestamp (10 bytes), 3-axis accelerometer values (each 8 bytes), 3-axis gyrometer values (each 7 bytes), the battery voltage (4 bytes), commas between each field (10 bytes), and the end of message indicator (1 byte).

Sensor Data Acquisition

Connection

Since many Bluetooth devices and sensors can expose private data, the devices to be connected first bond through a pairing process to confirm device identities. The pairing process may require some level of user interaction (for example to enter a passcode). Once paired, devices remember the bond so that they may connect again in the future without repeating the pairing process.

We use a pairing method known as Secure Simple Pairing which uses a form of public key cryptography for security and has been supported since Bluetooth 2.1. We specifically use the "Just Works" mode in which no user interaction is required and the user does not need to know a predefined pass code. We note that Windows 8 does not currently support the "Just Works" mode and a user has no choice but to go through a pairing process, which installs a virtual device representing the sensor. This can be confusing as there is no clear indication available to determine whether the device is currently in range or has simply been used in the past.

To select a device, we use the Bluetooth radio to scan for nearby slave devices, which broadcast information using the advertising channel. From this information we can get the device's engineering code, which allows us to infer the capabilities, and the device MAC address, which is needed to establish a connection. The BeatHealth mobile application (see D4.1 report) stores the MAC address of the last device selected.

The Bluetooth 4.0 specification does not set a limit on the number of connected BLE devices. Nevertheless, practical Bluetooth implementations have limited internal resources and hence Android phones may be limited to as few as 2 or 3 active BLE connections. Unlike BLE, the Bluetooth 2 specification sets a hard limit of 7 active connections, but again the number devices that can be practically connected may be less than that.

It is possible to connect both Bluetooth 2 and Bluetooth 4 sensors simultaneously to an Android phone. Current BeatHealth prototypes support one active Bluetooth 2 and one active Bluetooth 4 device simultaneously. This is a temporary software limitation and not a hardware limitation. Nevertheless, the results of ongoing testing are required before we can fully specify the maximum number of simultaneous connections supported by the specific hardware we are using.

Data Streaming Capacity, Packet Loss, and Reliability

Although several Bluetooth devices can be connected at once, the total data bandwidth available to them is also constrained. In other words, if a single sensor can successfully stream 100 data packets/second and if 3 sensors may be connected at once (before streaming data) there is no guarantee that all 3 connected sensors can successfully stream 100 data packets/second simultaneously.

We conducted some specific tests with the Moto G Android phone and an RFDuino (BLE) based test device and found the following:

With one connected BLE device, 100 notifications/second can be transmitted with little packet loss. (Using a slightly different approach to testing and a single connected BeatHealth IM4-230 sensor, packet loss in one trial was 75 from 985 packets, almost 8%. Closer inspection of the data indicated that packet loss occurred in batches of 3 or 4 consecutive packets at a time which is problematic for signal recovery. While it is natural to expect some packet loss in wireless communications this appears to be a rather high percentage and further investigation is required.)

With two connected BLE devices each attempting to send 100 notifications/second, 22.5% of the notifications were lost.

With three connected BLE devices each attempting to send 100 notifications/second, 28% of the notifications were lost.

Similar tests to verify the scalability for Bluetooth 2 devices are planned but have not been conducted at this time. We also plan to repeat the tests with alternative Android devices.

Feature Extraction

In the feature extraction module, the raw data supplied by sensors will be processed to produce the features and events required for the BeatHealth core music adaptation process. To avoid the need to store and upload large data logs of raw sensor data to the cloud there is also a desire to perform some processing of the raw sensor data to produce parameters of clinical or user value on the phone.

Extraction of the following fundamental features has been discussed and captured in user stories (requirements) where appropriate:

Step instants (time series per step) and gait cadence (derived from step instants)
Stride length (time series per stride or per second derived from GPS and inertial sensors)
Monopodal support duration
Respiration rate (time series)
Heart rate (time series, one update per second)

Of the features above, only the identification of cadence and step instants have been given detailed attention to date.

Gait Detection and Cadence

Development effort so far has focused on integrating sensors and attempting to resolve questions regarding timing variability and latency. For convenience therefore, the initial gait detection algorithm used in the mobile prototype app is an older DJogger algorithm designed for a single 3-axis accelerometer signal. The algorithm is described more completely in the Deliverable 3.2 report.

WP3 have subsequently developed a simple gyrometer based gait detection algorithm designed to be used with sensors worn on the leg (typically around the ankle). Again the algorithm is described in the Deliverable 3.2 report. This is the algorithm that is currently used by the Windows based laboratory prototype used for WP2 experiments. As it is compatible with the BeatHealth custom sensors we expect to implement this algorithm in the next iteration of the feature extraction module.

In general there is more work to do on gait detection, to ensure that it works with slower gaits (such as walking), with PD specific gaits, with Android and mobile device specific issues, and with a variety of sensor locations and sensor types.

Through companion projects (with undergraduate and masters students) we have done some preliminary investigation of alternative gait detection algorithms which may be more robust to non-uniform sampling. For example, we created a preliminary implementation of the RRACE algorithm for cadence estimation (Karuei, Schneider, Stern, Chuang, & MacLean, 2014) which utilises the Lomb-Scargle Periodogram (Lomb, 1976) for non-uniformly sampled data. This algorithm does not detect step instants however and would therefore need to be extended or to operate in conjunction with other algorithms to detect step instants.

Additional accelerometer-only gait detection algorithms studied in these companion projects included (Paller, Hausmann, & Wac, 2011; Tomlein et al., 2012).

Sensor Sample Timing Variability with an Android Client

The main challenge for the sensor integration activity in BeatHealth is to ensure that data from sensors can be received in a sufficiently timely manner to reliably estimate the instant that a step occurred. This is complicated by the manner in which network communications are normally implemented.

In general a sensor will sample some signal and then immediately attempt to transmit the sample value to the Android phone. For efficiency and protocol reasons, most transmitters do not actually transmit the data immediately but instead add it to a buffer (a type of first-in-first-out queue) to be sent at a later time. In particular, Bluetooth 4 GATT communications are limited to take place during prescribed connection intervals, often 20 to 40 ms apart, and sample data to be transmitted must be buffered between these connection intervals.

At the receiving Android device, data that is received will not necessarily be forwarded to the BeatHealth app immediately (since the operating system may be busy with other tasks). Instead the data will usually be added to a hardware buffer or low level operating system (OS) buffer to be forwarded to the app at a later time. The sensor transmit and Android receive buffers therefore add some variable amount of latency to communications. Furthermore, on a multitasking OS like Android, apps must wait their turn to run and for this reason there may often be several samples waiting in a buffer by the time the app is scheduled to run. The consequence of all this is that a signal sampled at uniform intervals by the sensor will appear to be both delayed and non-uniformly sampled by the time samples arrive at the BeatHealth app.

Estimating the Bluetooth Buffer Delay

The BeatHealth sensors use off-the-shelf Bluetooth modules whose buffer delays are not specified. Therefore we developed a method to empirically estimate the buffer delays. Briefly, this entailed configuring one Bluetooth module as the master and another as the slave. The same power source and clock source were used to drive both devices so that it was certain that the real time clocks of both devices (from which timestamps are obtained) were synchronized. Thereafter we measured the delays sending data from slave to master and used this to estimate of the buffer delay introduced by the sensors.

This delay was measured as 26.5 ms for the HM11 Bluetooth 4 module (used in the IM4-2xx sensors) and 18.3 ms for the HM06 Bluetooth 2.1 module (used in the IM2 sensors). In practice, however, this does not directly model the delay that will be experienced in transmitting from a sensor to an Android phone and it should therefore be considered an approximate estimate.

Sensor Sample Timing

It is possible to recover the uniform sample timing (except for some unknown communication delay) if the sensor can provide timestamps with each sample. This is the strategy used by the BeatHealth sensors (and used previously by the iPod "sensors" in connection with the DJogger system). However many commercial sensors do not provide timestamps (see for example the Metawatch) and in this case, the regularity of the received sample intervals becomes more important.

For this reason, detailed timing measurements were collected for a variety of sensors. Where sensor time stamps were provided, they were used to confirm that the sensor was sampling the signal of interest at regular intervals (typically 50 to 100 samples per second). This was confirmed to be the case for the BeatHealth IM2 and IM4 sensors. Therefore the investigation focused on the inter-sample intervals seen by the BeatHealth app on the receiving Android device.

Sample timing data was measured for a number of different sensors. In each test, just one sensor was connected and used. BeatHealth sensors were set to stream samples at a rate of 100 samples per second; other sensors streamed at their fastest native rate. In addition, BeatHealth sensor samples contained a message number and a sensor time stamp (in microseconds) in addition to other values. As soon as the BeatHealth software received a sample it obtained an Android timestamp and logged the message contents with this receiver timestamp to a file for later analysis. Using the logged data we could detect packet loss, confirm the accuracy of the sensor sample rate, and investigate the variability of the received sample intervals. Each trial in the experiment consisted of around 1000 or more samples collected from the sensor under test. In general several trials were conducted for each sensor but only one representative trial for each sensor is reported here. The following figures show the results for the individual sensors tested.

Figure 20:
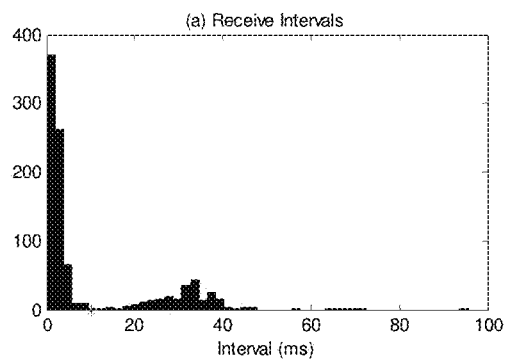
Figure 21:
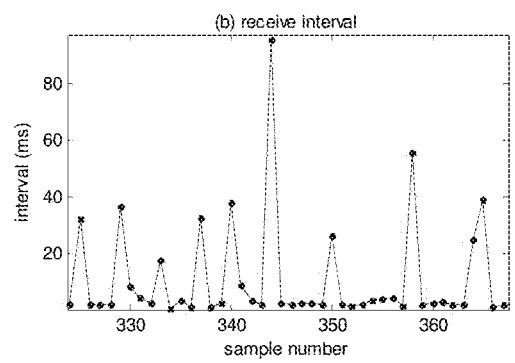

FIG. 20 (the histogram of intervals between received sensor samples) shows the results for the first sensor to be tested, the BLE based BeatHealth IM4-260 sensor. FIG. 21 is a subset of intervals between consecutively received sensor samples.

It is clear that the interval between consecutive samples at the receiver is almost never the 10 ms that would be expected for a 100 samples per second sample rate. Instead the receiver experiences a delay of 30 to 40 ms and then receives several samples with almost no delay between them. This is consistent with GATT inter-connection intervals of around 40 ms and 4 packets transmitted during each brief connection. Occasional longer delays were experienced and in this case samples were sometimes lost (because GATT notifications do not guarantee reliable delivery).

Figure 22:
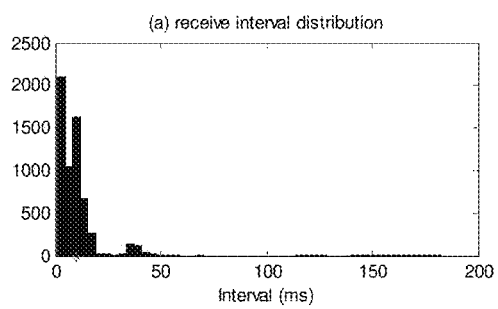

The results from the Bluetooth 2 based IM2-190 sensor were somewhat different as shown in FIG. 22 (the histogram of intervals between received sensor samples).

Figure 23:
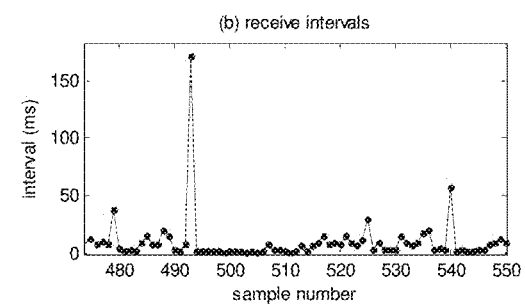

In this case the delay between consecutive samples was often around 10 ms though shorter and longer delays were experienced. Unlike the IM4 sensors, the IM2 sensors use a reliable transport (Bluetooth 2.1 RFCOMM). Therefore a delayed sensor reading (for example sample 492 in FIG. 23 (a subset of intervals between consecutively received samples) is followed by several readings in quick succession (interval between readings is almost zero) so that no readings are lost and the average sample rate is maintained.

Figure 24:
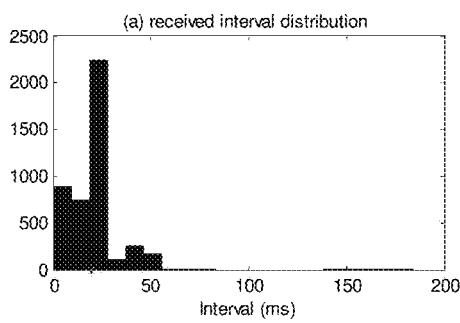
Figure 25:
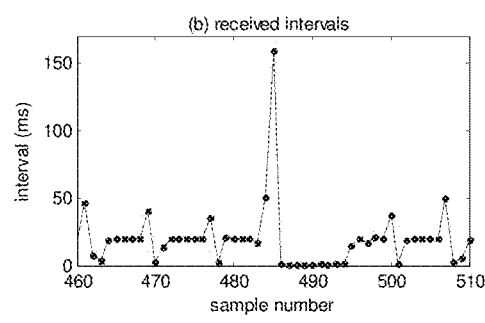

To examine the behaviour of Bluetooth 2 based sensors further, we measured received timing variability for the Metawatch. The results (shown in FIGS. 24 and 25) were even more consistent than for the IM2 sensor. FIG. 24 is the histogram of intervals between received sensor samples and FIG. 25 is a subset of intervals between consecutively received samples.

In this case the predominant interval between received samples was approximately 20 ms which matched the sampling rate of the Metawatch sensor. Somewhat longer delays (up to 50 ms) occurred in a seemingly regular pattern but were compensated immediately after by shorter intervals between samples. As before, there were occasional long delays (more than 150 ms in some cases). A possible explanation of the more regular pattern of received intervals observed is that the Metawatch sends less data for each sample and transmits samples less frequently.

Figure 26:
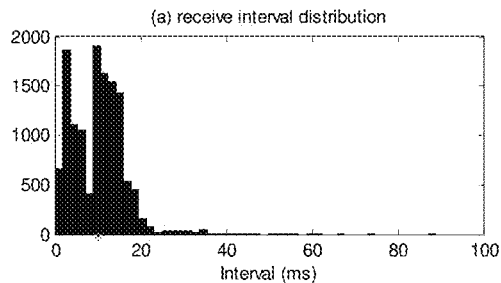
Figure 27:
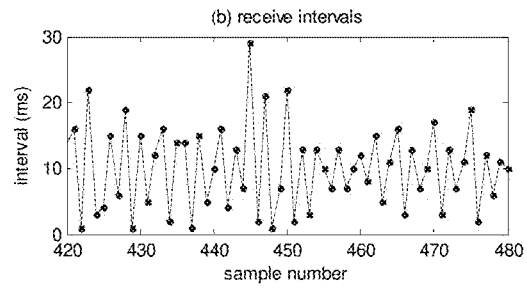

Finally we examined the behaviour of the MotoG internal accelerometer sensor. In this case there is no wireless communication delay or buffering expected. The Android application programming interfaces (APIs) allow one to ask for a sensor to stream at its fastest rate but no guarantees about that rate are given. Each sample passed to the app by Android contains a timestamp which represents the time at which the sample was taken (not shown below). The results for the received timing at the Android app can be seen in FIG. 26 et 27: FIG. 26 FIG. 26 is the histogram of intervals between received sensor samples and FIG. 27 is a subset of intervals between consecutively received samples.

The mean sample rate was approximately 99 samples per second. The sensor timestamps indicated that the sampling interval was predominantly 10 ms with occasional 20 ms intervals and, rarely, intervals as low as 5 ms which always followed an interval longer than 10 ms. The intervals between receiving the samples at the app are more variable. Some longer intervals (up to 90 ms) did occur, but these were always followed by several samples in quick succession (indicating that samples had been buffered).

The summary finding is that the received timing of samples cannot be relied upon. If a particular sensor does not supply sample timestamps, then we will need to integrate algorithms for recovering the sample timing using online measurements and certain assumptions about sample rate and sample interval variance. This naturally has implications for our ability to integrate off-the-shelf commercial sensors while achieving the timing accuracy necessary for BeatHealth.

We continue to examine the cause of the intermittent longer intervals between samples received by the Android app but one hypothesis to be investigated is that it may simply be due to task scheduling within Android. Specifically, if there are other tasks to execute, then Android must switch away from the BeatHealth app temporarily, run those other tasks and then switch back to the BeatHealth app again. If this switched-away period is sufficiently short, then there should be little impact, but if the period is longer (for example 100 ms) then it could explain the occasional long intervals.

Sensor Sample Timing Variability with a Windows 8.1 Client

We decided to investigate the timing of sensors with Windows 8.1 for two reasons: the laboratory prototypes provided by WP3 were based on a Windows 8 Tablet and we wanted to know if the Bluetooth behaviour on Windows 8 differed substantially from that on Android.

The tests were conducted using the same methodology as the Android tests except that in this case the client software, which was responsible for receiving and logging the sensor samples, was running on Windows 8.1. The Windows 8.1 hardware platform was a MacBook Pro that had been booted into the Windows 8.1 OS (that is, it was not simply running a virtual machine).

Figure 28:
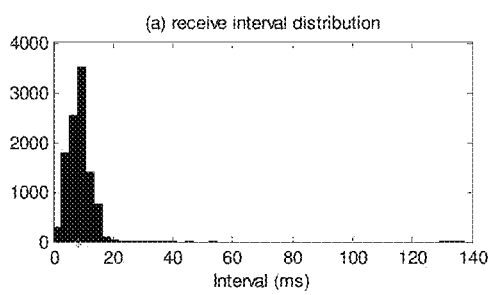
Figure 29:
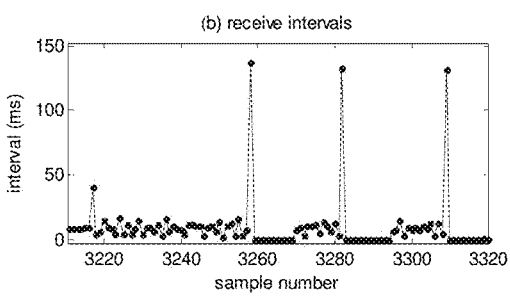

To understand the performance of the current DJogger system and WP3 laboratory prototypes we tested a single iPod Touch 4 "sensor" using the Sensor Monitor Pro app on the iPod to send samples over WiFi to the Windows 8.1 device. The WiFi network was a dedicated network hosted directly by the Windows device without the use of any other router. The results are shown in FIGS. 28 and 29. FIG. 28 is the histogram of intervals between received sensor samples and FIG. 29 represents a subset of intervals between consecutively received samples.

Samples sent from the iPod device contain a timestamp which indicates when the sample was taken. Although the iPod app streamed samples at 120 samples per second the results showed that this data stream contained duplicate entries (two or more sample values with the same timestamp and values). The mean accelerometer sampling rate on the iPod (derived from the mean interval between non-duplicate samples) was measured to be 93-96 samples per second (depending on how outliers due to lost samples were identified).

At the receiver, the mean interval between (possibly repeated) samples was 8.6 ms (corresponding to 116 samples per second) but occasional intervals were much larger than this (up to 137 ms in the worst case).

As the iPod app uses UDP transport over WiFi (as is typically used for real time data) there is no guarantee of reliable delivery of samples. Analysis of the sensor time stamps indicates that some samples (approximately 1.4%) were lost in the test. It should be noted that packet loss occurred intermittently throughout the trial and was not particularly associated with long internals between received samples. It is worth noting that the test was conducted in ideal laboratory conditions with just one sensor streaming data and the Windows device and iPod sensor both stationary and within 1 m of each other.

Although the iPhone was not considered a sensor platform we felt it would be useful to understand its performance since the iPhone is the major competitor to Android phones. Therefore we performed a similar test to the iPod and discovered that the iPhone 5 internal accelerometer is sampled less frequently than that of the iPod, at around 54 samples per second. This means for example that the DJogger gait detection algorithms (which currently require a sampling rate of 100 samples per second) would need to be adapted to use the internal accelerometer in an iPhone.

As mentioned previously, the consortium partners wished to replace the iPod "sensors" used in the initial WP3 laboratory prototypes with the sensors that would be used by the mobile platform as soon as possible. In support of this we examined the timing behaviour of the BeatHealth IM2 sensor with a Windows 8.1 client. The results are shown in FIGS. 30 and 31 and these should be compared with the results in FIGS. 22 and 23 (which showed the same sensor used with an Android client).

Figure 30:
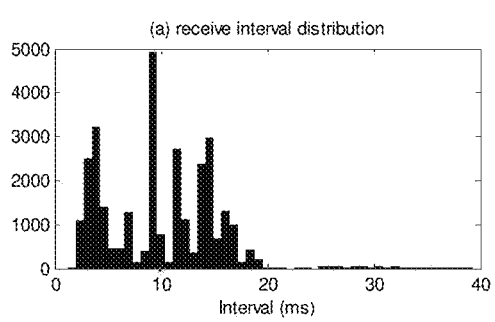
Figure 31:
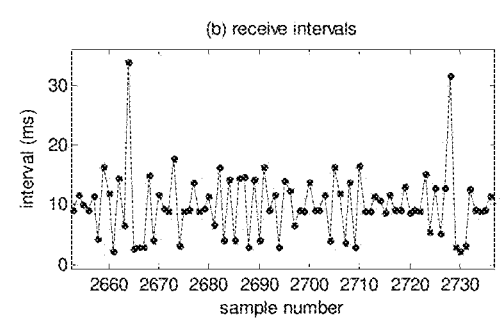

FIG. 30 represents) the histogram of intervals between received sensor samples and FIG. 31 is a subset of intervals between consecutively received samples.

It is clear that the received sample intervals are much more consistent with the Windows 8.1 client than with the Android client. In this case the largest intervals were less than 40 ms. It is currently unclear whether the improved performance is a result of better operating system scheduling, higher performance computing hardware, or a better Bluetooth implementation on the client.

Unlike the iPod sensors (FIGS. 28 and 29) the IM2 sensors do not suffer from any lost samples. The received interval consistency for IM2 sensors (SD=5.3 ms) was similar to the iPods (SD=4.6 ms). These positive results indicate that the IM2 sensors should perform as well as the iPod sensors with the Windows 8 based laboratory prototypes. Finally we examined the behaviour of the BeatHealth IM4 sensors with the Windows 8.1 client. The results are shown in (FIGS. 32 and 33) and should be compared with those in (FIGS. 20 and 21).

Figure 32:
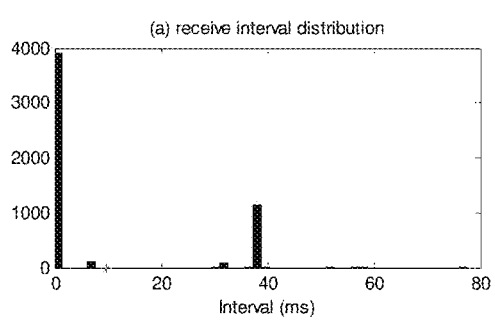
Figure 33:
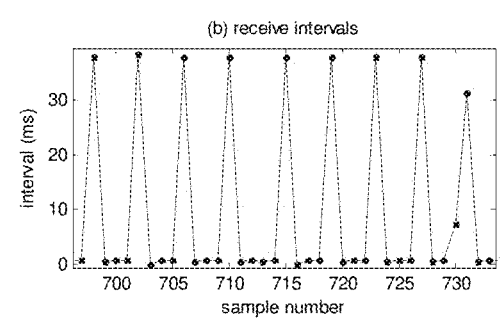

FIG. 32 represents the histogram of intervals between received sensor samples and FIG. 33 represents a subset of intervals between consecutively received samples.

The first 40 samples in the received stream (not shown in the figure) featured some larger intervals (up to almost 80 ms) but stabilized thereafter into the pattern shown in FIG. 33. This is much more consistent than the pattern observed with an Android client. Again it is not clear if the operating system scheduling, computing hardware, or Bluetooth implementation is the dominant factor in the observed difference and further tests will need to be conducted.

It is clear however that the timing behaviour of the IM4 sensors with the Windows 8.1 client is perfectly satisfactory for BeatHealth. Moreover, just 0.2% of all samples were lost in this configuration compared to almost 8% when the same sensor was used with an Android client.

Event to Audio Latency

Ultimately the purpose of physiological signal feature extraction in BeatHealth is to identify the features and events which drive the music adaptation process. A very important aspect of this is ensuring that the adapted music is close to zero degrees out of phase with the events to be synchronised (for example, steps when running). This problem is complicated by various sources of latency which occur in the system. In the previous section we examined the communication latency between sensor and client, but there are also additional latencies within the client.

Figure 34:
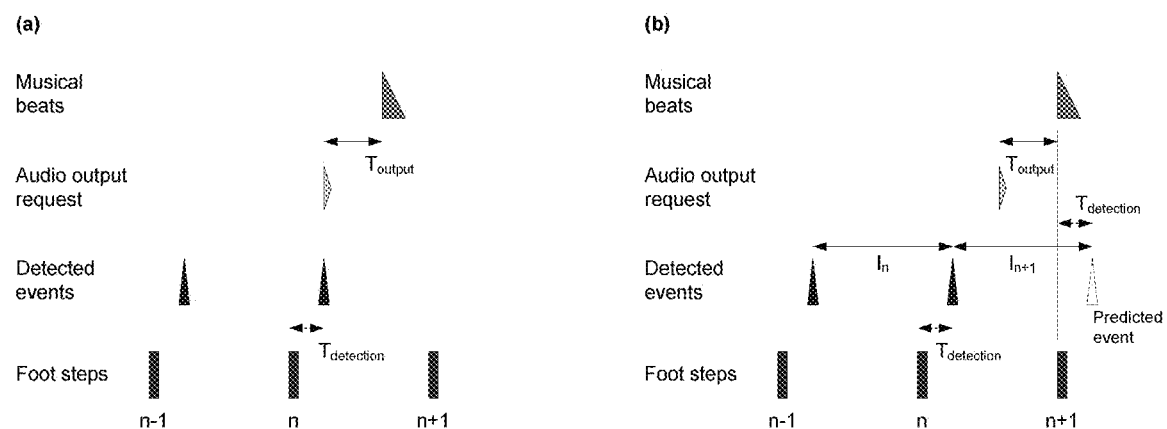

If all latencies are small enough it is possible to achieve sufficiently good synchronisation between extrinsic events (foot steps) and the musical output using a reactive approach. This approach is shown in FIG. 34(a) (reactive output without latency compensation) where the musical output is requested immediately after the event at time n is detected. If the detection latency, $T_{detection}$ (between the step event and its detection in the app), and the audio output latency, $T_{output}$ (between the app requesting sound output and the sound actually being produced), sum to less than the detection threshold for asynchrony then the music will be perceived as if it is synchronous with the step events. This detection threshold appears to be between 10-50 ms, depending on the source (see for example Rasch, 1979; Repp, 2002).

If the latencies are not small enough to ignore then it is no longer possible to use a reactive approach to sound output-instead a predictive approach must be taken as shown in FIG. 34(b) (predictive output incorporating latency compensation). In this case predicted event n+1 is predicted to occur at interval $I_{n+1}$ after the detected event n. To compensate for the audio output latency, $T_{output}$, the sound output must be requested $T_{output}$ seconds prior to the predicted event time. Furthermore, to ensure that the sound output is synchronous with the actual step event, the sound output must be requested a further $T_{detection}$ seconds earlier again.

The measurements in section 0 indicated that the detection latency for Android (which is affected by the interval between received samples) varied and could exceed 50 ms on its own. We also designed test equipment and experiments to measure the total latency ($T_{detection}+T_{output}$) for the BeatHealth sensors and MotoG Android phone. Initial results suggest that the total latency is between 200 and 300 ms indicating that a predictive approach to music output synchronisation will be required.

This experimental work is ongoing and further data is due to be collected for analysis. We expect to repeat this work for different Android devices to determine whether the latency varies much among devices. Furthermore, results have not yet indicated whether the latency is stable for a given device or if the total latency can vary between runs of the app.

Although there are several timing issues which affect feature detection and music synchronisation we believe that appropriate modelling, estimation, and prediction algorithms will permit these issues to be overcome and this is part of the focus of future work in Task 4.2.

Deliverable D4.2 Status

The deliverable D4.2 has been successfully delivered but the scope has changed from that originally anticipated in the description of work. On one hand some additional work arose when it became clear that we would need to develop BeatHealth custom sensors (at least for now). On the other hand the schedule for Task 4.2, wherein all effort was expended in year one of the plan, was inconsistent with the resources allocated to NUIM in the project.

Therefore, in agreement with the coordinator, we propose revising the task to distribute the effort over the three years of the project (ending month 30). We have prioritised key aspects of the sensor integration task in year 1 and remaining items will be addressed in year 2 and 3. In addition, we propose a new deliverable, D4.7, which will report on the conclusion of the sensor integration task in month 30.

In year 1, Task 4.2 focused on the most important and necessary aspects of sensor integration. We have successfully evaluated a number of sensors and sensor technologies. Custom BeatHealth sensors and the Android phone's own internal accelerometer signal have been integrated into the data acquisition and feature detection subsystems of the prototype BeatHealth app. Finally, a prototype BeatHealth mobile app which utilises these subsystems has been developed, thereby satisfying the WP4 requirements for MS3, the second version of the BeatHealth prototypes.

Nevertheless it is clear from the body of this report that further investigation and development is required on many of the more subtle and complex aspects of sensor integration. In particular, the implementation of latency correction is quite basic in the current prototypes and this affects the ability of the mobile app to achieve true zero phase alignment of music and steps. These issues will be addressed in year 2 and 3.

Future

As a result of ongoing changes to the wider technological environment outside BeatHealth and the modified scope of deliverable D4.2, currently planned future work includes the following items among others:

- Accurate characterization of extrinsic event to music output latencies so that true zero phase alignment can be more closely achieved by the music adaptation algorithms
- Additional testing of the BeatHealth custom sensors to confirm their robustness and communication reliability over time and during exercise
- Possible step detection on board the BeatHealth sensors to greatly reduce the amount of data traffic to be transmitted (subject to being able to adequately synchronise time between the sensor and mobile device)
- Integration of the heart rate sensor (and possibly the respiration sensor) into the mobile app
- Confirmation regarding the upper limits for the number of devices that may be connected at once and the simultaneous streaming data rates that can be achieved
- Investigation of the impact of the Google fit SDK (Google, 2014b) Investigation of the impact of Google's Android Wear (Google, 2014a) initiative and the current trend towards smart watches
- Investigation of the possible benefits of the next version of Android, dubbed "Android L", which claims to introduce real time audio and reduce the input and output latency to 10-20 ms

REFERENCES

Gomez, C., Olle, J., & Paradells, J. (2012). Overview and Evaluation of Bluetooth Low Energy: An Emerging Low-Power Wireless Technology. *Sensors*, 12, 11734-11753.

Google. (2014a). Android Wear Retrieved 23 Sep. 2014, from https://developer.android.com/wea r/index.html Google. (2014b). Google fit Retrieved 23 Sep. 2014, from https://developers.google.com/fit/

Imec. (2014). Hoist Centre and imec Unveil Small, Light Health Patch with Enhanced Accuracy.

iRhythm Technologies Inc. (2014). ZIO XT Patch Retrieved 23 Sep. 2014, from http://www.irhyth mtech.com/zio-solution/zio-patch/index.html Karuei, I., Schneider, O. S., Stern, B., Chuang, M., & MacLean, K. E. (2014). RRACE: Robust realtime algorithm for cadence estimation. *Pervasive and Mobile Computing*, 13, 52-66.

Lomb, N. R. (1976). Least-squares frequency analysis of unequally spaced data. *Astrophysics and Space Science*, 39(2), 447-462.

Paller, G., Hausmann, J., & Wac, K. (2011). Using digital Phase-Locked Loop (PLL) technique for assessment of periodic body movement patterns on a mobile phone. Paper presented at the 1st Int. Workshop on Frontiers in Activity Recognition using Pervasive Sensing.

Polar Electro. (2014). H7 Heart Rate Sensor Retrieved 23 Sep. 2014, from http://www.polar.com/en/products/accessories/H7 heart rate sensor Rasch, R. A. (1979). Synchronization in Performed Ensemble Music. *Acustica*, 43, 121-131.

Repp, B. H. (2002). Automaticity and voluntary control of phase correction following event onset shifts in sensorimotor synchronization. *Journal of Experimental Psychology: Human Perception and Performance*, 28(2), 410-430.

Tomlein, M., Bielik, P., Krátky, P., Mitrík, Š., Barla, M., & Bieliková, M. (2012). *Advanced Pedometer for Smartphone-Based Activity Tracking*. Paper presented at the International Conference on Health Informatics, Vilamoura, Portugal.

Zinc Software. (2014). Lumafit Retrieved 23 Sep. 2014, from http://www.lumafit.com/

Part-4-Project-610633_Deliverable-4.7: Signal Processing Description

Deliverable Description

Deliverable D4.7 is the final report on "physiological sensor integration". This report follows on from Deliverable 4.2 and documents the final results on the incorporation of the suite of sensors into the BeatHealth mobile application platform.

Deliverable D4.2 contained the initial work on building sensors for the BeatHealth system and integrating those sensors with mobile devices using the Android operating system. At the close of this report it was realised that further development was needed to tackle many of the subtle and complex aspects of sensor integration that had arisen. The tasks identified included:

- Finalizing the sensor design, its enclosure, and determining how it will be attached to the person.
- Integration of a suitable heart rate sensor into the mobile application.
- Improving the communication system between the sensors and the mobile app during activity to ensure robustness.
- Implementation of step detection and analysis algorithms on the mobile platform that utilizes data delivered from the BeatHealth sensors
- Examine the sample timing variability between the sensors and the client platforms This document explains the work carried out in the meantime to satisfy these tasks. The remainder of this document is organized as follows. First, an illustration of the overall system architecture to show the relationship between the sensors and mobile devices is given. Then, with reference to Deliverable 4.2, a short recap on the sensor technologies and devices selected for BeatHealth is provided. Next the implementation of custom sensors designed specifically for BeatHealth is described. The specification for the selected Heart Rate capture sensor is then given. Experiments carried out to measure the connectivity of sensors are documented in the next section. After this, the implementation of the Step detection and stride length measurement algorithms is explained. The final technical section describes the sample timing variability measurements. A conclusion section finally closes the document.

Overall System Architecture

The BeatHealth System is composed of two parts: a portable smartphone or tablet device that interacts with a set of sensors that are worn by the user on their person. The sensors are used to measure physiological signals as the user is walking or running and send this data to the mobile device for analysis and recording. The result of the signal processing on the mobile device is auditory feedback that is delivered to the user though the manipulation of the playback of music tracks. This manipulation of the music acts as a personalized rhythmic auditory stimulation (i.e., tailored to the individual's motor performance and physiological response) that should improve gait and mobility performance.

Figure 35:
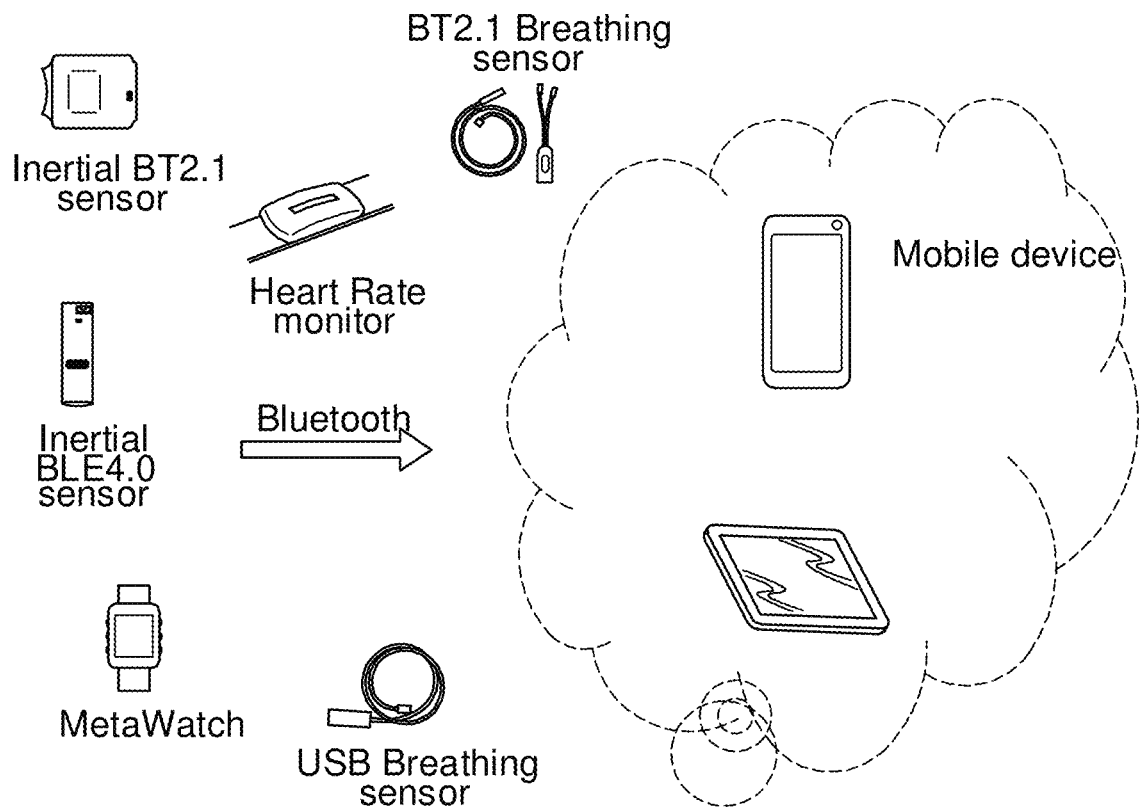
Figures 57, 58:
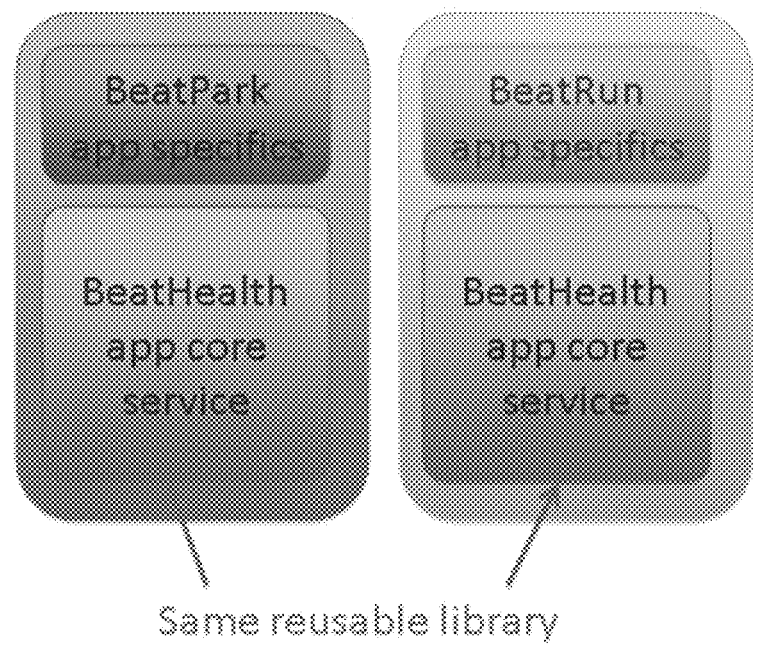

A variety of sensors can be connected within the BeatHealth system as shown in FIG. 35. These sensors measure signals such kinematics (via inertial sensors), Heart rate, and Breathing patterns. All communication with the mobile devices is via the Bluetooth protocol and therefore all can be considered as wireless wearable sensors. An early task in this work was to assess the availability of suitable commercial off-the-shelf sensors for the needs of BeatHealth. This evaluation required formalizing a number of essential criteria which were:

The suitability of the communications technology,
Their compatibility with the envisaged hardware platforms,
The availability of an open Application Programming Interface (API),
The data sampling rate
The battery operating time, FIG. 57 in the Appendix provides a screenshot of the spreadsheet where this comparison was carried out under these headings. The next section will briefly explain the outcome of this evaluation and then describe the custom sensor technology developed at NUIM.

BeatHealth Sensor Technology

Introduction

Kinematic and heart rate sensing were determined by the consortium team as the required measures for the final end-user BeatRun system. For the Parkinson's Disease (PD) patients using BeatPark, kinematic sensing only was required. The Breathing sensor was determined to be of interest for the experimental trials only. Kinematic sensing could be achieved with inertial sensors: a 3-axis accelerometer (5 g scale) and a 3 axis gyrometer. The internal sensors available on typical Android mobile phone devices were determined insufficiently accurate for the project's purposes and no other suitable of-the-shelf commercial sensing devices were available. This motivated the development of a customised solution that could be mounted as required on the lower limbs (in the vicinity of the ankle).

Figure 36:
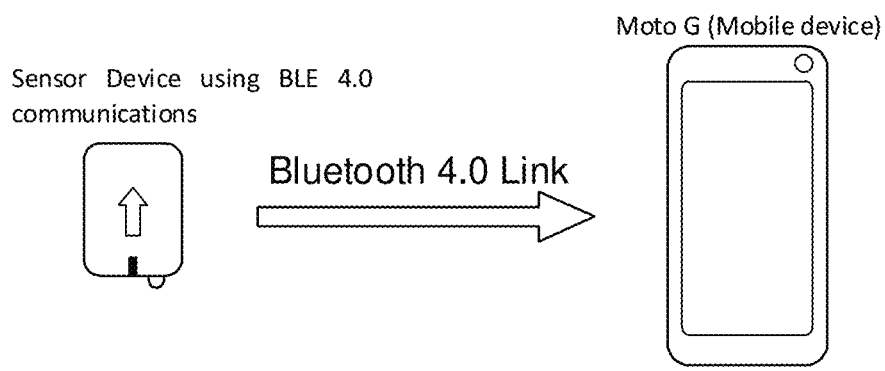
Figure 37:
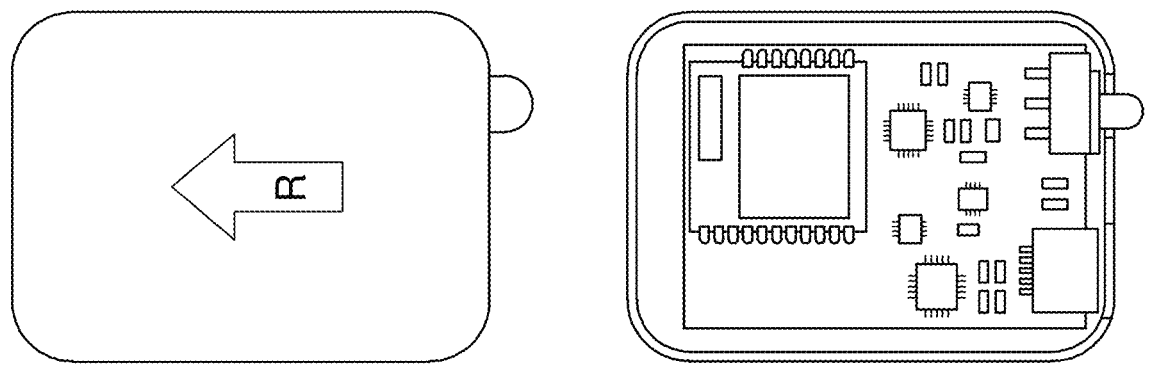

The principal wireless communication technologies compatible with Android mobile devices, such as the Motorola Moto-G phone (selected for the BeatHealth application) (Motorola, 2016), and Windows 8.1 Tablets (used in trials by UGhent) were considered first of all as discussed in Deliverable 4.2. Here it was determined that Bluetooth 4.0 Low Energy (BLE) and Bluetooth 2 (classic Bluetooth) were the most useful supported wireless stacks. BLE was determined to be the first choice for sensors used by the BeatHealth mobile platform primarily because of its power consumption profile. BLE permits low power communication facilitating smaller sensors (due to less battery bulk) and longer operation times (for a given battery pack). However, one disadvantage of this protocol is that some data packets can be lost in the communication process. This can be accommodated at higher layers but must explicitly be managed in the BeatHealth application. FIG. 36 illustrates the simple connectivity between a sensor and a mobile device.

The mobile platform was also required to support Bluetooth 2 devices (for compatibility with the sensor systems used in the experimental studies). For example the requirement for heart rate sensing was that the signal could be recorded over a particular time period such as the duration of a run. This was best accomplished using a commercial sensor: the Zephyr H×M (Zephyr, 2016). Beyond the physiological sensing user location was also considered as relevant data (for walk and run tracking). Geolocation is sensed using GPS and fortunately this is available as an integrated function in the chosen mobile phones for BeatHealth.

The Custom BeatHealth Inertial Sensor

A number of deficiencies prevented the use of off-the-shelf commercial sensors. These became apparent after the comparison process (see FIG. 57). The primary drawbacks included (1) significant cost for a large number of sensors, (2) the lack of real-time data streaming, (3) the data rate available was too slow, or (4) timestamps were not integral to the data packets which would facilitate step detection and step length measurement. Thus, for BeatHealth a decision was made after the feasibility studies to produce a customised BeatHealth sensor device to measure running and walking movements. The evolution of the sensor design is well documented in Deliverable 4.2. The final Bluetooth 4.0-equipped sensor uses an advanced MEMS (Micro-Electro-Mechanical Systems) inertial-sensor technology. The sensor supports one communications link at a time and uses the Bluetooth 4.0 Generic Attribute Profile (GATT) to communicate with other devices. The data is transmitted at the high speed rate of 100 data samples per second. The device has been designed to be small enough to attach to shoelaces or can fit into the pocket beneath the insole of compatible shoes. It is powered by a small rechargeable battery that will retain its charge for about thirty five hours full time use which is sufficient for multiple training sessions of the type envisaged by the BeatHealth proof of concept experiments and subsequent real world use. Images of the sensor casing and its internal PCB are shown in FIG. 3.2. On the casing of the sensor is a letter to mark which leg it should be placed on ('R' for right for example). In the second image on the right the sensor can be seen to have a power switch (on/off) and a microUSB port for interfacing with a computer and for recharging.

Figure 38:
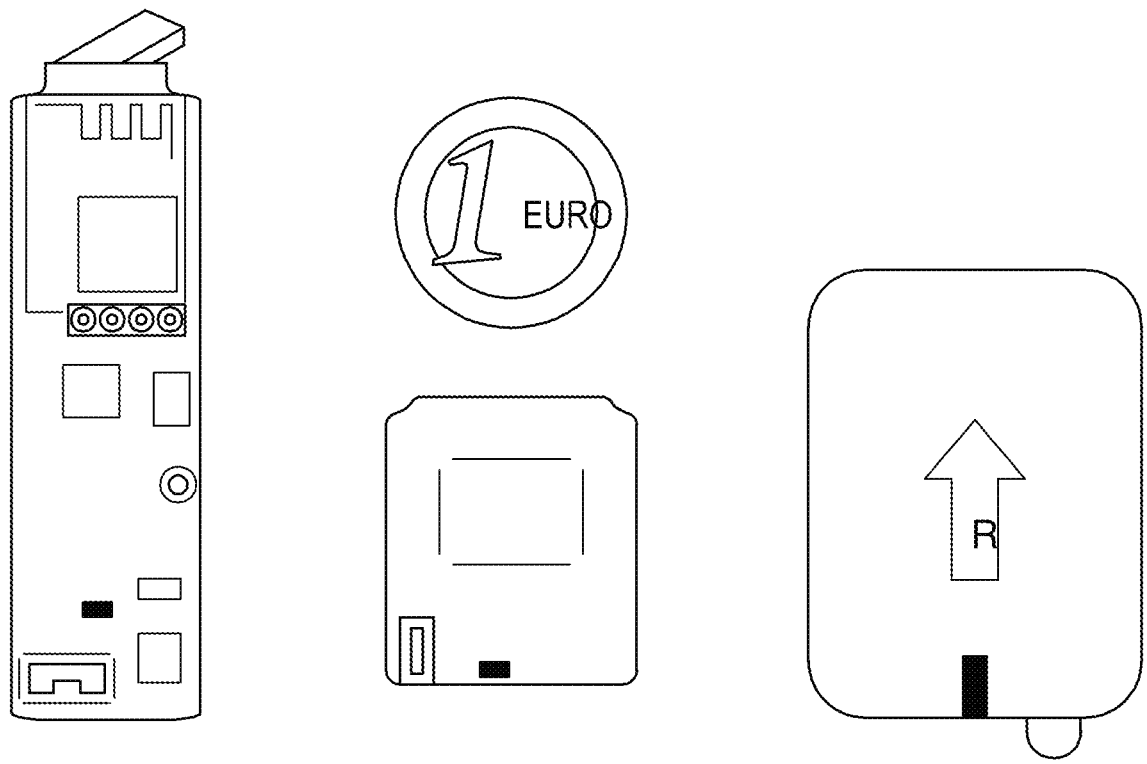

The sensor dimensions are L×W×H [mm]=41×30×17, and its weight is 16 g. An impression of the physical size of the current sensor shown in FIG. 35 can be found in FIG. 38 by comparing it with a 1 coin. Also shown in the figure are the earlier prototypes of the BeatHealth sensors (the Bluetooth 2 sensor is on the far left and an earlier version of the Bluetooth 4.0 sensor in the middle). It can be seen that the final sensor size is midway between that of the earlier models. The slightly larger size compared to the smallest prototype is explained by the addition of a robust enclosure and a larger, rechargeable power pack. For reference, Deliverable 4.2 described the design and implementation of the early prototypes.

The primary design improvements that lead to the final sensor are as follows:

Inertial technology: this has been redesigned and improved on. An upgraded version of the Inertial Measurement Unit (IMU) has been included so that now it is equipped with a 3-axis accelerometer, a 3-axis gyroscope, a 3-axis magnetometer and an internal temperature sensor. The printed circuit board (PCB) for this sensor includes circuitry for monitoring the battery charge level and the Bluetooth signal strength. Both these functions improve integration and the user experience.

Battery life: the non-rechargeable cell coin batteries used previously have been replaced by a similar size but higher capacity lithium-polymer rechargeable battery set. This provides a 5-fold improvement in battery life to 35 hours.

Interfacing: a charge management controller and microUSB port have been integrated so that now a standard smart-phone charger can be used to charge the device. The microUSB port can also be used for interfacing with the sensor's firmware for updates.

Enclosure: a proper, robust plastic enclosure was designed for the sensors to protect them during the experiments.

3.3. Sensor Production

The sensor system prototypes were built in-house at NUIM. Given the important requirement of a small formfactor for the sensors it necessitated the use of small, surface mount electronics components. It is thus a very time-consuming and rather complex process to build an individual sensor. Furthermore, it is difficult to produce high quality Printed Circuit Boards (PCB) on which the electronic components are mounted without industrial standard equipment. Thus, for the production of the sixty sensors needed for the Beatealth Proof-of-Concept (POC) experiments, it was decided that the most sensible approach was to contract their manufacture to a professional company that could deliver consistent quality at a reasonable cost but within a short time span. A suitable company was found and they produced all subsequent sensors in accordance with the design and bill of materials supplied by NUIM. As each batch of sensors was received from this contract manufacturer, they were tested at NUIM to ensure that they were working correctly.

3.4. Hardware Architecture of the Sensors

Figure 39:
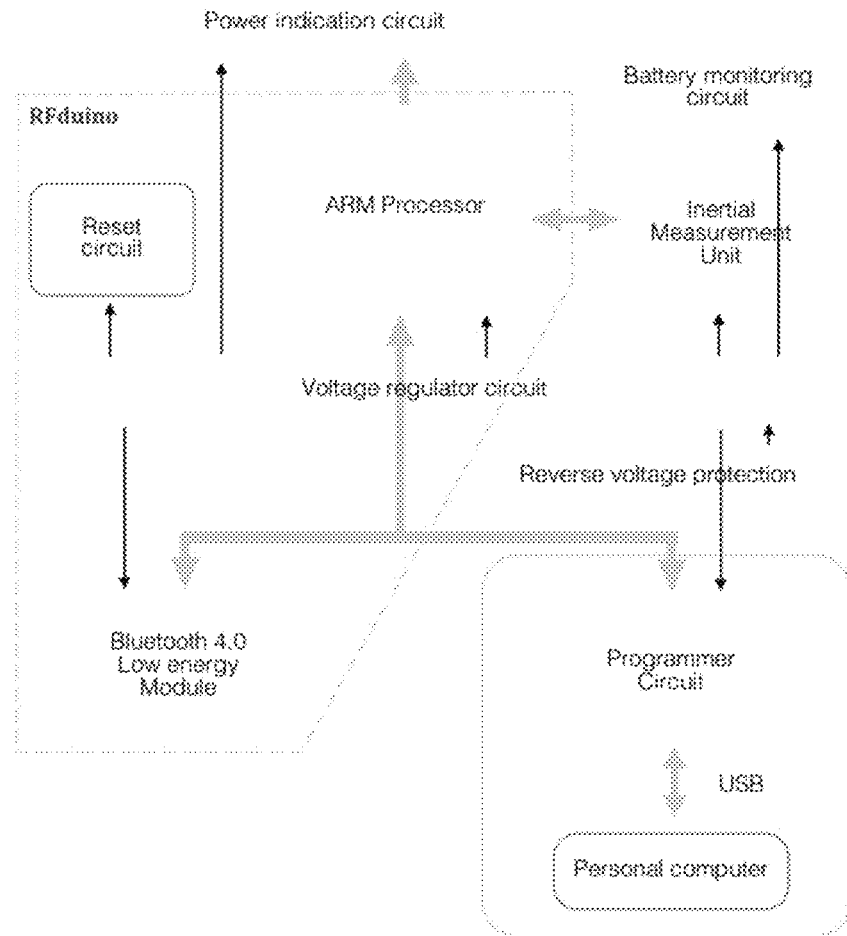

A block diagram indicating the primary components of the sensor is given in FIG. 39. The hardware design is based on an embedded system implementation using the ARM Cortex-M0 32-bit processor. Its clock source is a 16 Mhz low power crystal oscillator. It has 128K bytes of in-system self-programmable flash program memory and 16K bytes internal RAM memory. The ARM processor controls all peripheral components of the system.

This processor communicates directly with the Inertial Measurement Unit. The IMU unit is a MPU-9250 rev 1.0 by InvenSense incorporated (Invensense, 2016). This unit contains a 3-axis accelerometer with a full-scale range of ±8 g, a 3-axis gyroscope with a full-scale range of ±1000°/sec, and a 3-axis magnetometer full-scale range of ±4800 µT. Its sampling rate is 100 Hz. The unit collects the raw data from the accelerometer and gyroscope, and provides it to the microcontroller for further processing.

The sensor system through the BLE unit transmits this data obtained from the motion sensors to the mobile device. This BLE (Bluetooth 4.0) module is an off-the-shelf RFduino device with a transmission range specified to reach up to 10 meters (RFduino, 2016).

It also can connect to the programming interface that facilitates microUSB connectivity to an external computer for firmware updates. An important component is the Reset circuit for the microcontroller. This ensures that the microcontroller commences operation in the correct state on start-up.

Figure 40:
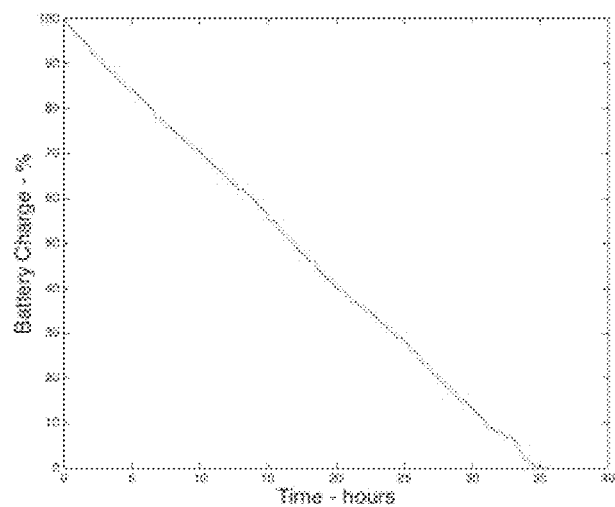

The remaining circuitry is related to power regulation and distribution. The sensor is powered by a lithium polymer 300 mAh battery, with a typical battery life of 35 hours. A graph of the battery discharge characteristic is given in FIG. 40 (Discharge characteristic of RFduino BLE 4.0 sensor with a 300 mAh battery) and is clearly linear over time. The Battery Monitoring circuit facilitates the provision of feedback to the user in terms of remaining battery hours and the current usage. The output of the battery pack provides an operating voltage of 3.3V. This is conditioned through the Voltage Regulator circuit which is responsible for the regulation and stabilization of this input voltage. The Reverse Voltage Protection circuit protects the system's components from damage in the case of an accidental incorrect polarity terminal connection with the battery. The Power indication circuit drives a LED when the sensor is switched on.

3.5 Format of the Sensor Data Messages

Figure 41:
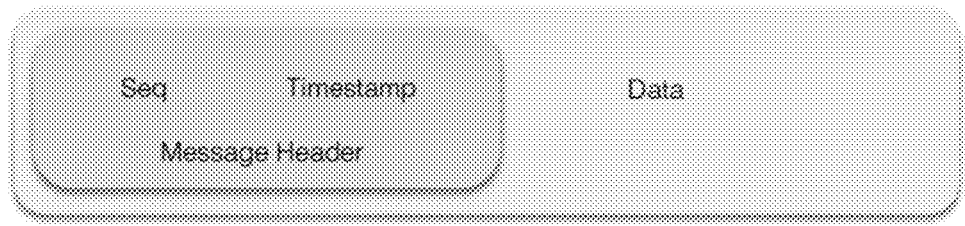

The Bluetooth 4.0 inertial sensor can only communicate with one paired device at a time. Furthermore, the sensor works in slave mode so that the connection can only be established by the master device. It transmits 100 data packets per second and ignores any incoming data. The packet size is fixed and contains 20 bytes. FIG. 41 (Bluetooth 4.0 inertial sensor packet structure) illustrates the packet structure: there is a Message Header along with the data itself.

The Message Header has two components:

Seq [1 byte]—this is the overlapping packet sequence number that lies within the range [0-255] which is used to keep track how many messages have been sent/received. The order of messages can be checked at the receiver, and thus that the occurrence of lost or duplicated messages can be detected.

Timestamp [4 bytes]—this is the number of microseconds since the sensor board began running the current program. This number will overflow, after approximately 70 minutes. For a sensor with a 16 MHz crystal the resolution is 4 microseconds (i.e. the value returned is always a multiple of four).

The Data format can be described as follows:

Data [15 bytes]—this field contains the 3-axis acceleration information within the full-scale range of ±8 g and a measure of the battery voltage, its state of charge, and a Received Signal Strength Indication (RSSI) value.

Figure 42:
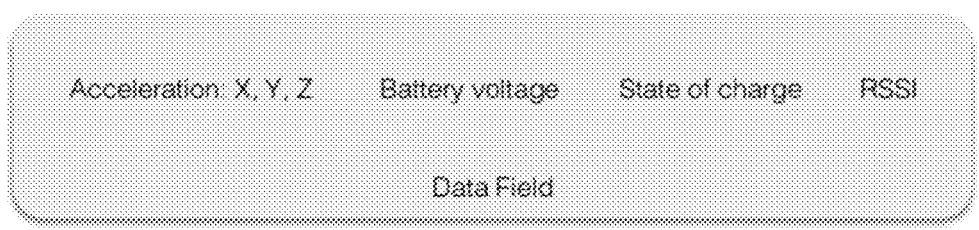

This information is illustrated in graphical form in FIG. 42 (Data field structure). In more detail, the format of the data field is

[2 bytes] 16-bit 2's complement value of the most recent X axis accelerometer measurement

[2 bytes] 16-bit 2's complement value of the most recent Y axis accelerometer measurement

[2 bytes] 16-bit 2's complement value of the most recent Z axis accelerometer measurement

[1 byte] battery voltage (floating point value encoded in 1 byte)

[1 byte] battery state of charge (from 0-100%)

[1 byte] RSSI level (the signal strength)

The Battery voltage (up to 3.3V) is encoded in 1 byte: 11|0011|00→3.30V

|11| this is the first 2 bits that stores the mantissa [0-3]

|0011| the next 4 bits stores the first digit of the exponent [0-9] |00| the last 2 bits stores the second digit of exponent (0 or 5)

This is 0 if between [0-4], or 1 if between [5-9]

For example: 11|0011|00 this represents 3.30V mantissa: 3 exponent first digit: 3 exponent second digit: 0

3.5. Sensor Circuit Schematic

Figure 43:
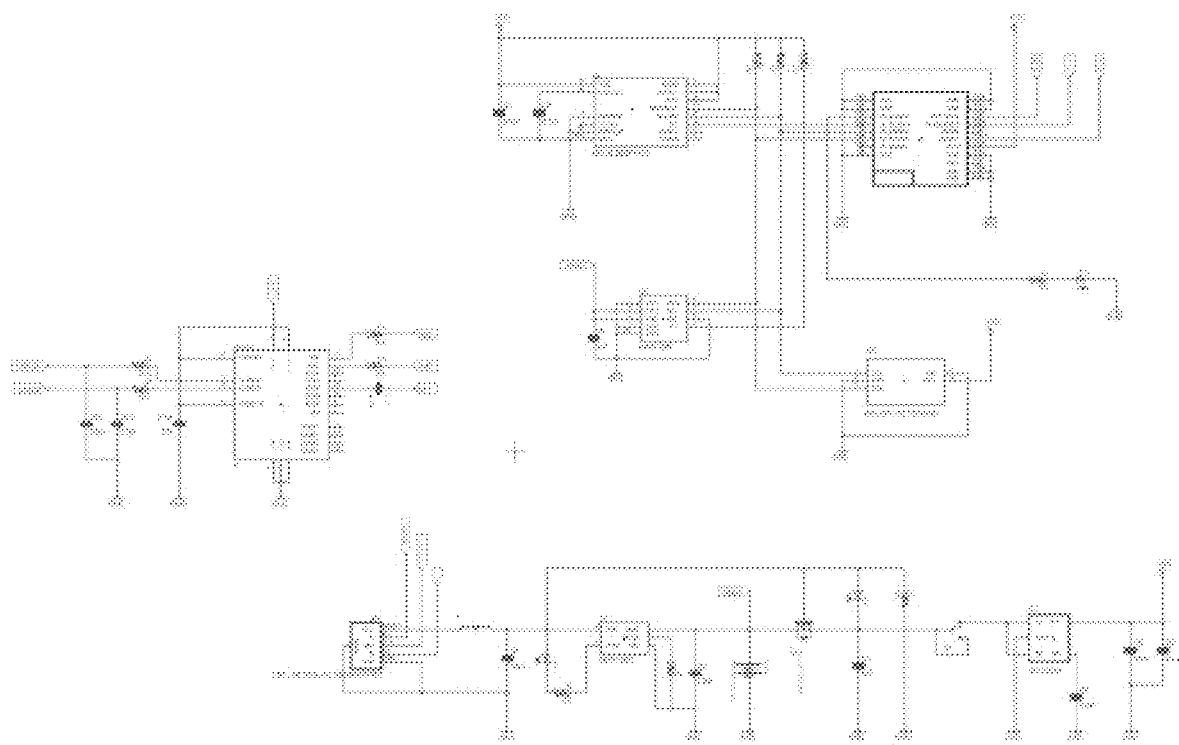

FIG. 43 (Bluetooth 4.0 inertial sensor schematic) provides a detailed schematic diagram of the sensor. It illustrates the connections between the primary Integrated Circuit (IC) components, the USB interface IC connections, and the circuit power management components. All BeatHealth sensors were designed using the EAGLE Light Edition software package (CadsoftUSA, 2016).

Figure 44:
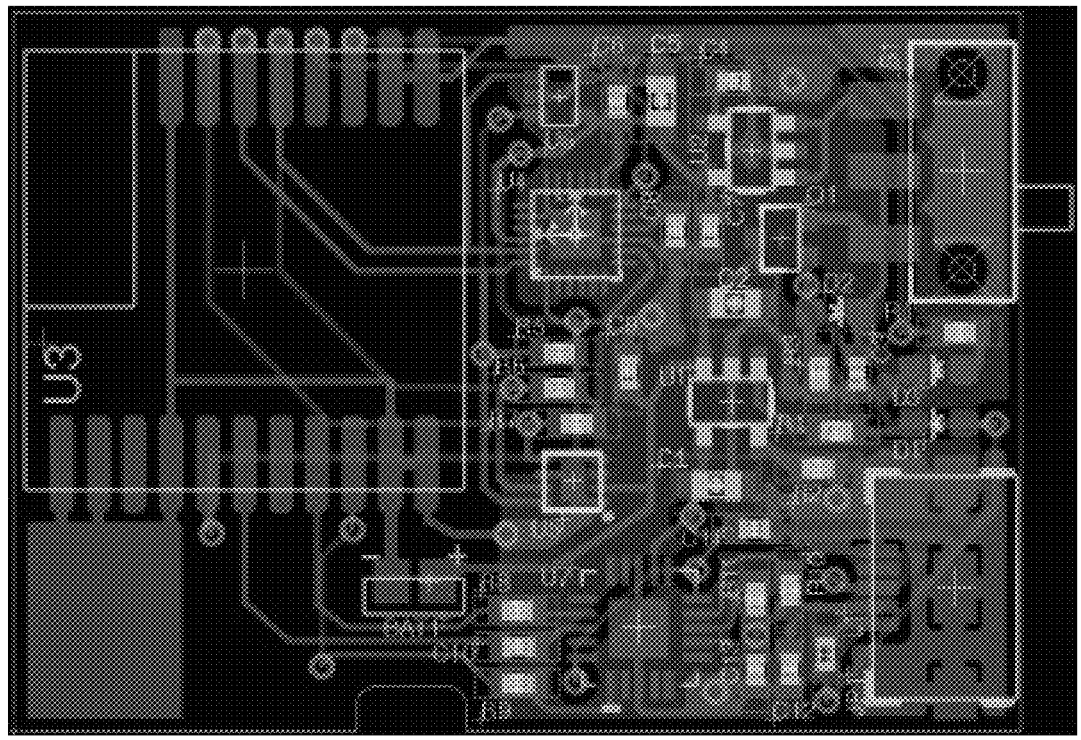

The Eagle Software package will automatically generate the Printed Circuit Board (PCB) layout from the schematic. This is shown in FIG. 44 (Bluetooth 4.0 sensor PCB). The key is to make it as compact and lightweight as is possible so that it is an unobtrusive as possible and thus facilitate a small sensor size.

3.6. Sensor Enclosure Solution

Figure 45:
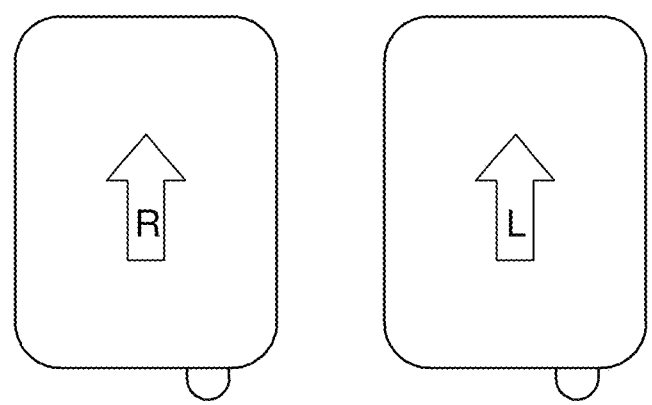

Once the PCB design was completed and the bare boards were tested, numerous commercially available enclosures for the BeatHealth sensors were evaluated. However, none of them were found to be satisfactory. It was agreed at a consortium meeting that NUIM would design a robust enclosure that was of a proper size and shape. Based on responses from a number of manufacturers specializing in producing plastic enclosures and companies providing 3D printing services, one was selected (3DprintUK, 2016) that produced enclosures from design files provided by NUIM. FIG. 45 provides a photograph of the final sensor enclosures. The final dimensions including the enclosure are 41 mm (L)×30 mm (W)×17 mm (H). The letter R and L signify the ankle each sensor is to be attached to and the arrow points out the direction of sensor orientation. The protruding piece seen on the bottom of the sensor is not part of the enclosure but is a switch attached to the sensor PCB that is used to turn the board on and off.

3.7. Strap for Sensor Attachment

Figure 46:
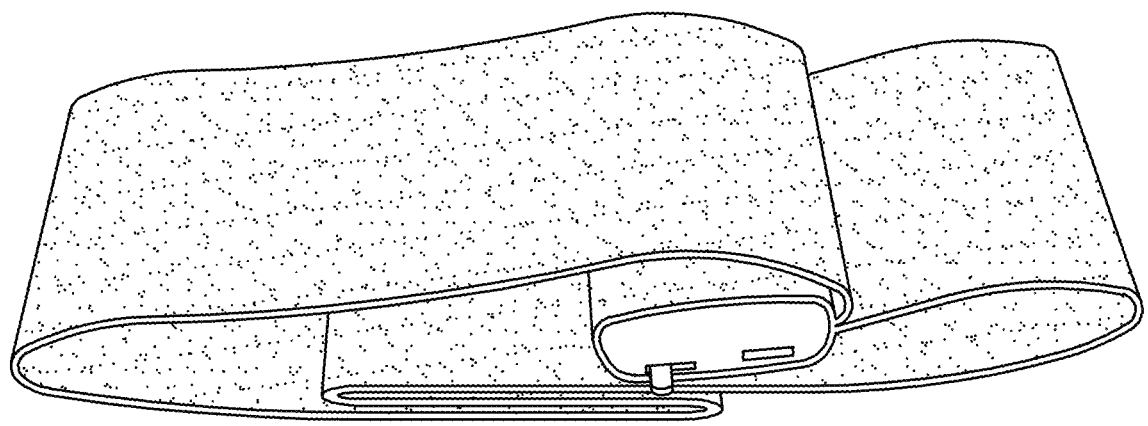
Figure 47:
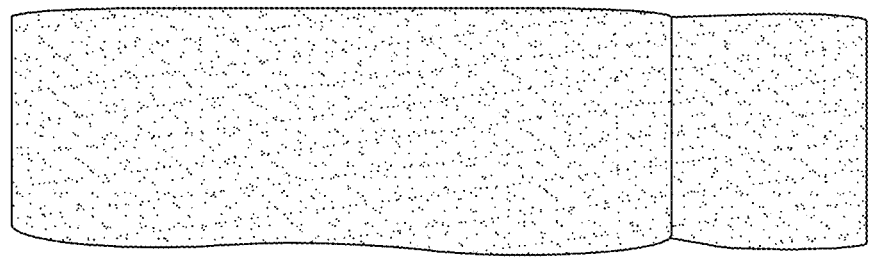
Figure 48:
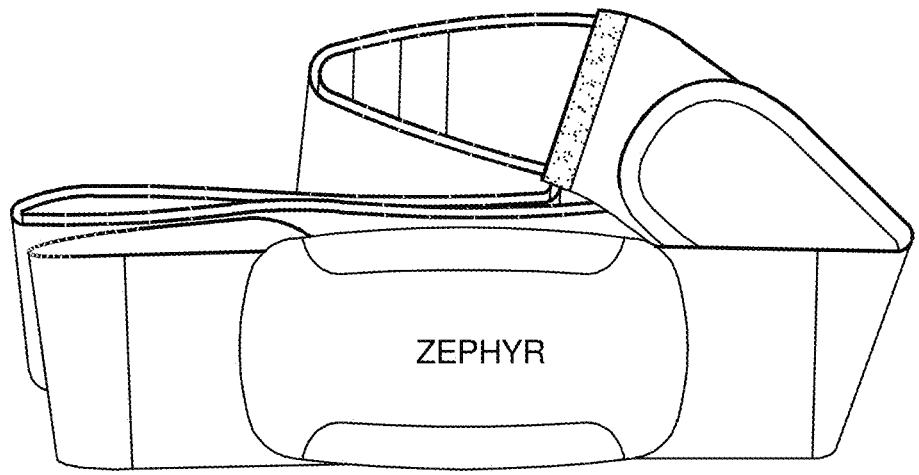

The sensors need to be attached to the users using straps. In particular, as PD patients will require gait sensors to be mounted comfortably on the leg/ankle there was a need to design good quality straps. A number of prototypes were made using an elasticated fabric as shown in FIGS. 47 and 48. A small pocket is made using a loop to hold the sensor. This is shown in the top panel of FIG. 46 with the sensor inserted and is shown empty in the bottom panel. Velcro is used to secure the strap around the ankle as it facilitates both easy fastening and quick opening. Additionally, with Velcro pads of sufficient size it allows the tightness of the strap to be adjusted to the diameter of the ankle of the user.

3.8. Heart Rate Sensor

As discussed in Deliverable 4.2 a number of candidate off-the-shelf heart rate sensors were evaluated and the Zephyr H×M heart monitor (Zephyr, 2016) (which is shown in the FIG. 48) was selected for use with the BeatHealth application. It is worn on a strap that fits around the upper body with the sensor positioned at the front of the chest. It communicates only over Bluetooth 2 RFCOMM using a custom message format. One data message is transmitted each second containing the heart rate, the last 15 heart beat timestamps, the instantaneous speed, the distance covered, and the number of strides taken. Its specifications are Heart Rate range: 25-240 BPM
Battery type: Rechargeable Lithium Polymer
Battery life: 26 Hours per charge
Transmission range: 10 m
Transmission Frequency range: 2.4-2.4835 GHz
Its Operating limits are:
Temperature range: −10° C. to 50° C.
Humidity range: 5%-95%
Water Resistant up to 1 m For completeness it is worth recalling the reasons that this device was chosen:

It is compatible with Android devices
It has a stable Bluetooth connection
Its battery is rechargeable
It provides an API available for developers
Along with providing the heart rate, other parameters, such as the RR interval, are also available These attributes are fully compatible with the desirable sensor features mentioned in Section 2 earlier in this document.

4. Sensor Data Communications

4.1. Sensor Connectivity

The connection technology of the sensors has been described in Deliverable 4.2. To summarise, the sensors must bond with the mobile device through a pairing process to confirm device identities. A pairing method known as Secure Simple Pairing in "Just Works" mode is used. To select a sensor, the BeatHealth application running on the mobile device uses Bluetooth to scan for nearby slave devices. All identified devices appear in the application to be selected by the user. Once paired, the BeatHealth mobile application stores the MAC address of the sensors. It is possible to connect both Bluetooth 2 and Bluetooth 4 sensors simultaneously to an Android phone. Tests carried out discovered that it was possible to connect 4 BeatHealth sensors simultaneously with a consistent data streaming rate of 100 Hz.

More than 4 BeatHealth sensors could be connected, up to the Bluetooth protocol limit of 7 devices, but this larger number was observed to have a significant impact on the streaming rate which slowed considerably.

The streaming rate is reliable with the require number of devices connected: 2 BeatHealth sensors and the heart rate sensor. The BeatHealth application has thus been configured to support two active Bluetooth 4 (Inertial ankle-mounted sensors), and one active Bluetooth 2 (Heart rate sensor) simultaneously. It is possible to expand this at a later stage if desired.

4.2. Data Packet Loss Measurements

The Bluetooth 4.0 protocol is not reliable (it does not guarantee the arrival of every packet sent) and it is therefore perfectly normal and expected to find a certain amount of packet loss. Bluetooth disconnections are also possible but these are expected to happen less frequently. The software automatically recovers from disconnections, by reconnecting to the sensor, but this can take several seconds during which no packets can be received from that sensor.

The connectivity of the sensors in terms of dropped connections and missing packets was tested with both indoor and outdoor trials using a Moto-G Android phone, the chosen mobile platform for the BeatHealth experiments. The indoor trials consisted of the sensors remaining stationary on a desk. The outdoor trials consisted of participants wearing the sensors while walking and running.

For the indoor basic connectivity tests the BeatHealth system was left recording information for 30 minutes where the phone and sensors were placed 1 m apart. Three tests were performed: (1) one sensor connected, (2) two sensors simultaneously connected, and (3) three sensors simultaneously connected. For all of these tests there were no disconnections and no packet losses recorded. Thus, the test was completely successful.

In order to test the connectivity of the sensors in an outdoor environment a series of experiments were undertaken. The first experiment involved two participants taking short brisk walks around a track over a distance of approximately 400 m. These walks began and ended with approximately 10 seconds of standing still. The phone was worn in different locations on the person of the participants for each trial: (1) in a pouch placed on the waist, (2) in the side pocket of a jacket, and (3) in the breast pocket of a jacket. The results for these trials are presented in Tables 6 and 7 for participants 1 and 2 respectively.

TABLE 6

Results for Participant 1 for outdoor walking trials with different phone positions

| Sensor Location | Duration of Trial (seconds) | Left Sensor- Number of Disconnects | Left Sensor- Total Duration of Disconnects (seconds) | Left Sensor- Number of Packets lost other than disconnects | Right sensor- Number of Disconnects | Right Sensor- Total Duration of Disconnects (seconds) | Right Sensor- Number of Packets Lost other than Disconnects |
|---|---|---|---|---|---|---|---|
| Waist facing left | 200 | 0 | 0 | 48 | 0 | 0 | 0 |
| Jacket, right side pocket. | 186 | 0 | 0 | 0 | 0 | 0 | 0 |
| Jacket, right breast pocket. | 202 | 0 | 0 | 0 | 0 | 0 | 3 |

For Participant 1 Table 4.1 shows that there were no disconnections by either the left or right sensor due to disconnections. However, for the left sensor when it was placed at the waist there were 48 packets lost (0.2%) and for the right sensor when it was placed in the breast pocket of the jacket there were three packets lost (0.01%).

TABLE 7

Results for Participant 2 for outdoor walking trials with different phone positions

| Sensor Location | Duration of Trial (seconds) | Left Sensor- Number of Disconnects | Left Sensor- Total Duration of Disconnects (seconds) | Left Sensor- Number of Packets lost other than disconnects | Right sensor- Number of Disconnects | Right Sensor- Total Duration of Disconnects (seconds) | Right Sensor- Number of Packets Lost other than Disconnects |
|---|---|---|---|---|---|---|---|
| Waist facing left | 194 | 0 | 0 | 0 | 0 | 0 | 0 |
| Jacket, right side pocket. | 190 | 0 | 0 | 0 | 0 | 0 | 0 |
| Jacket, right breast pocket. | 206 | 0 | 0 | 0 | 0 | 0 | 0 |

In Table 4.2 for Participant 2 there were no packets lost for either sensor under any circumstances. Overall, remembering that 100 packets/second are transmitted, the results are excellent indicating that sensor connectivity is strong. For participant 1 it was hypothesized that the lost packets were due to a shadowing effect on the signal caused by the large physical size of the participant.

For a second experiment a single participant went for two outdoor runs in a suburban environment; the first with a duration of approximately 28 minutes, and for the second it was approximately 3 minutes. For both experiments the mobile phone was placed in a pouch on the waist. The results of these trials are presented in Table 8. From the Table it can be seen that only a small number of packets were lost from both sensors, no more than five (0.03%) overall from either sensor in both experiments.

TABLE 8

Results for two outdoor running trials with same phone position

| Waist facing left | Duration of Trial (seconds) | Left Sensor- Number of Disconnects | Left Sensor- Total Duration of Disconnects (seconds) | Left Sensor- Number of Packets lost other than Disconnects | Right sensor- Number of Disconnects | Right Sensor- Total Duration of Disconnects (seconds) | Right Sensor- Number of Packets Lost other than Disconnects |
|---|---|---|---|---|---|---|---|
| Waist facing left | 1668 | 0 | 0 | 4 | 0 | 0 | 0 |
| Waist facing left | 197 | 0 | 0 | 2 | 0 | 0 | 5 |

These results show significant improvement over the early results reported in Deliverable 4.2 and demonstrate the improvements in the sensor performance that have been achieved in the intervening time.

5. Feature Extraction

Processing of the raw data supplied by sensors occurs on the mobile device. In essence this examines the data for features and events from which physiological descriptions of the current activity can be derived. These can then drive the BeatHealth music adaptation process. Extraction of the following fundamental features occurs currently:

Step instants and number of steps per minute (or gait cadence)

Heart rate (time series, one update per second)

Another feature that is of particular interest for PD patients is the Stride length that can be derived both using GPS and the data from the inertial sensors. However, the GPS system does not work indoors and in such circumstances an algorithm driven using the data from the inertial sensors must be used.

5.1. Step Detection and Stride Analysis

The report for Deliverable 3.2 describes gait detection algorithms that use a 3-axis accelerometer signal and a gyroscope based approach that works with sensors worn on the lower limbs. These have been integrated into the BeatHealth application, tested, and then refined where necessary. It is desirable to include stride length measurement as part of the BeatHealth system. Of particular interest to the BeatHealth clinical researchers is the impact of the BeatHealth technology on the Stride length of PD patients (Morris et al, 1996). Imparting a cognizance to the patient that could lead to regularization of their stride length using the technology would be a positive outcome. The necessary data processing can be carried out online or it can be tackled offline as long as the accelerometer and gyroscope data is stored as the user is engaging with the application. It is difficult, however, to compute the stride length accurately as it must be calculated indirectly from the accelerometer and gyroscope readings under a number of assumptions. If these assumptions are inaccurate then the estimates will contain errors. The algorithms can be tuned to balance their influence if an alternative set of measurements using sophisticated equipment can be accessed that will provide accurate ground truth values for stride length by which a comparison with the sensor results can be made, and thus from which tuning parameters can be derived.

Figure 49:
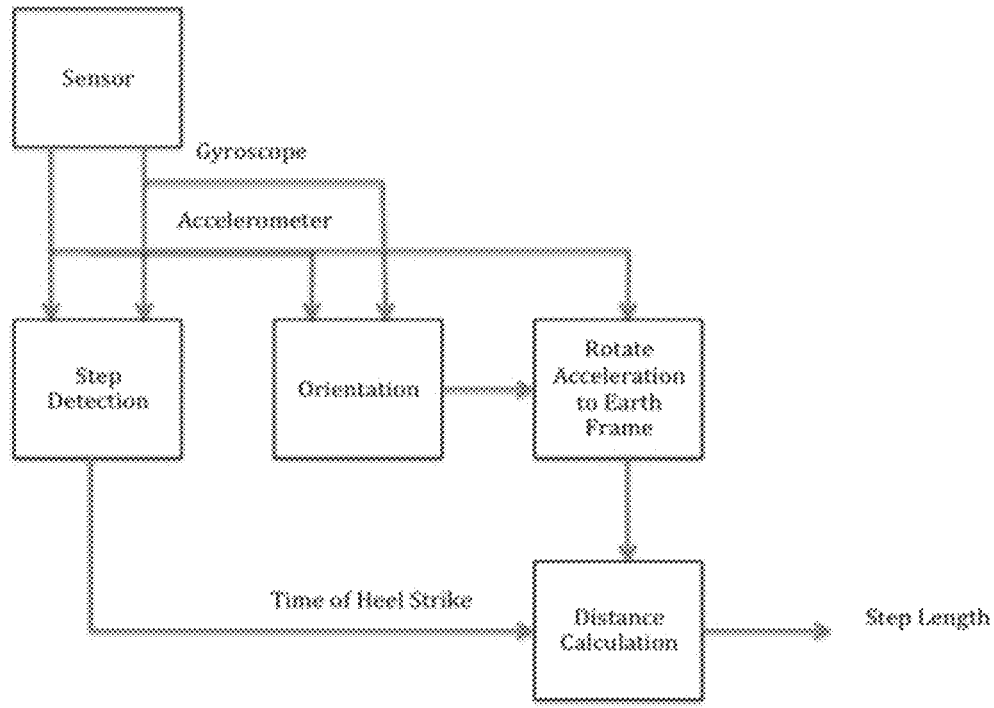

The BeatHealth stride length algorithm has to find the distance between consecutive heel strikes using the data from both the accelerometer and gyroscope sensors. Heel strike timing is determined using the algorithm described in Deliverable 3.2. The estimation of the stride length has many similarities to the problem of estimating one's position based on knowledge of a previous position plus estimates of speed and direction (dead reckoning). It is required to first choose an initial heading in an arbitrary direction to define the inertial frame. From there it is possible to find the orientation of the sensor, and then rotate the data from the accelerometer into this inertial frame, followed by a double integration of the acceleration to get the position. This process is illustrated by the block diagram in FIG. 49 (Block diagram of stride length measurement algorithm.).

The estimation of the orientation relative to the inertial frame is used in two vital steps of the calculation of change in position; 1) to calculate the relative change in direction of the sensor, and 2) to remove the effect of the acceleration due to earth's gravitational field from the acceleration measured by the accelerometer in the calculation of distance travelled. There are several methods for estimating sensor orientation including methods based on Kalman filtering (Nilsson et al, 2012), the complementary filter (Mahony et al, 2008) and gradient descent (Madgwick et al, 2011). The gradient descent technique has been shown to be comparable in accuracy to Kalman filter approaches (Madgwick et al, 2011), while having less tuning parameters and being more computationally efficient. This algorithm uses a quaternion representation of the orientation which avoids singularities that can occur when using Euler angle representations.

In order to estimate the change in position, an initial estimate of the orientation and an initial velocity is required. Data from the accelerometer is used to initialize the orientation. Zero-velocity (ZV) detection is also an essential element of the stride length estimation as it prevents the position error increasing quadratically over time. For each stride there is a point at which the velocity of the sensor approaches zero. This is during the stance phase when one foot carries the body's full weight. The zero velocity point is detected using both the accelerometer and gyroscope data. The zero velocity corrections are applied at one point per stride and at these points the velocity is set to zero, and the excess velocity is removed before integrating to find the change in position. The gradient descent algorithm is then used to adjust the orientation estimate in the direction of the acceleration vector.

To evaluate the performance of the stride length algorithm an experiment was performed in Montpellier. Ten Subjects participated and all of these had been diagnosed with PD. Ground truth was recorded using the Vicon system (Vicon, 2016). The Vicon capture space was about 5 m. Each participant made 20 passes through the capture space, giving an average total of 138 strides per participant. BeatHealth sensors were worn on the ankles of the patients and the data from the BeatHealth sensors recorded on a Motorola Moto-G phone. Vicon markers were placed on top of the BeatHealth sensors. In order to align the BeatHealth data with the ground truth Vicon data, Delsys Inertial Measurement Unit (IMU) sensors (Delsys, 2016) were mounted in close proximity to the BeatHealth sensors. A Delsys Trigger Module was also used to ensure synchronization between Vicon and Delsys systems. Analysis of this experiment is ongoing and will be reported in detail in deliverable D4.8.

Figure 50:
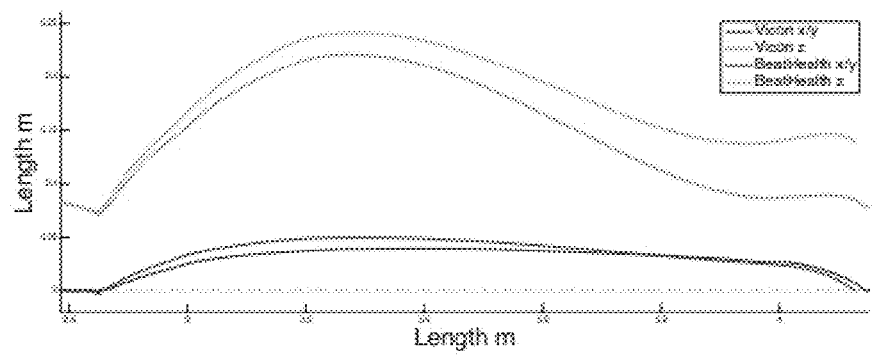
Figure 51:
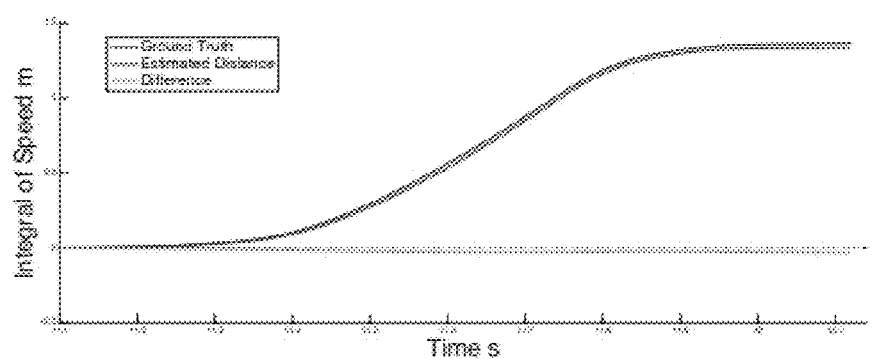

FIG. 50 provides an example of data for a single step trajectory. The blue and red lines (representing Vicon and BeatHealth step data respectively) are the trajectory of a step projected onto the x/y plane. The green and light blue lines (representing the Vicon and BeatHealth respectively) lines are the corresponding z-axis values. As can be seen in the plot there is a good match in terms of shape for the z-axis data, and more importantly there is a close agreement between the x/y data for the Vicon and the BeatHealth sensors, with the BeatHealth step length estimate falling just a little short in this particular case. Integration of the x/y data to get an estimate of the velocity is shown in FIG. 51. The difference between the ground truth and the velocity derived from the BeatHealth sensor is given by the green line and its deviation from zero is shown by its misalignment with the dashed black line.

Over all the measured patient data the average ground truth stride length 1.098 m. The average absolute error between the ground truth stride length and the estimated stride length using BeatHealth sensor data was 6.53 cm. The Spearman correlation coefficient between the estimated and ground truth stride length was found to 0.95. The algorithm used to estimate stride length is still undergoing further refinement and it may be possible to improved this performance. It will be possible to run any improved algorithm post hoc on the raw data collected as part of the proof of concept experiments.

Figure 52:
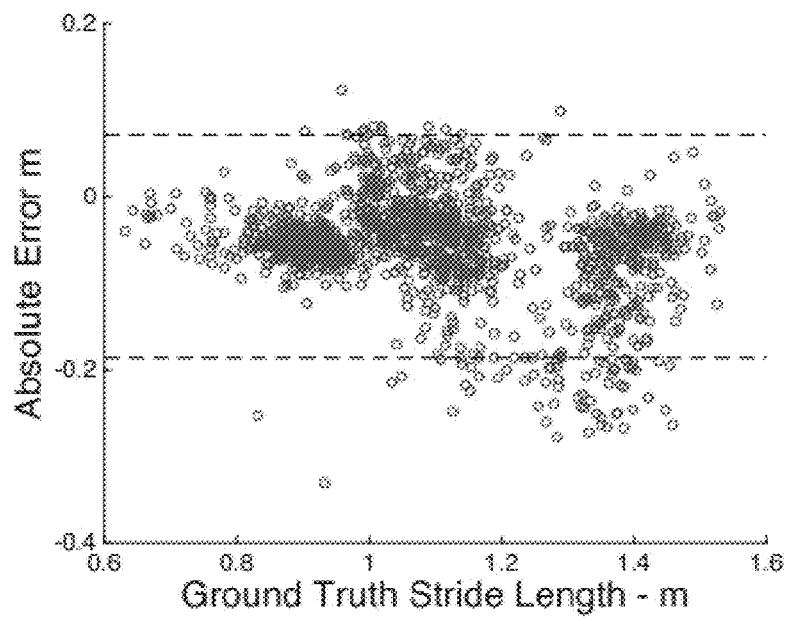

FIG. 52 illustrates the distribution of the absolute error with respect to the stride length and additionally plots dashed lines at ±1.96 SD. This interim result based on the current algorithm and analysis to date compares favourably with recently published work (Rampp et al, 2015). Nevertheless the stride length estimates appear to become less accurate for longer stride lengths and this point will be examined further in deliverable D4.8.

6. Sensor Sample Timing

A key challenge for the sensor integration activity in BeatHealth was to ensure that data from sensors can be received in a sufficiently timely manner to reliably estimate the instant that a step occurred. This is slightly complicated by the manner in which network communications are normally implemented. Specifically, Bluetooth 4 GATT communications are limited to take place during prescribed connection intervals, often 20 to 40 ms apart, and the sample data to be transmitted must be buffered between these connection intervals. Additionally, at the receiving Android device, the received data will not necessarily be forwarded to the BeatHealth application immediately but instead the data will usually be added to some buffer for an intermediate period. The sensor transmit and Android receive buffers therefore introduce some variable amount of latency to the communications. Ultimately, a signal sampled at uniform intervals by the sensor will appear to be both delayed and non-uniformly time sampled when it arrives at the BeatHealth app.

6.1. Measuring the Buffer Delay with the Motorola Moto-G Phone

Figure 53:
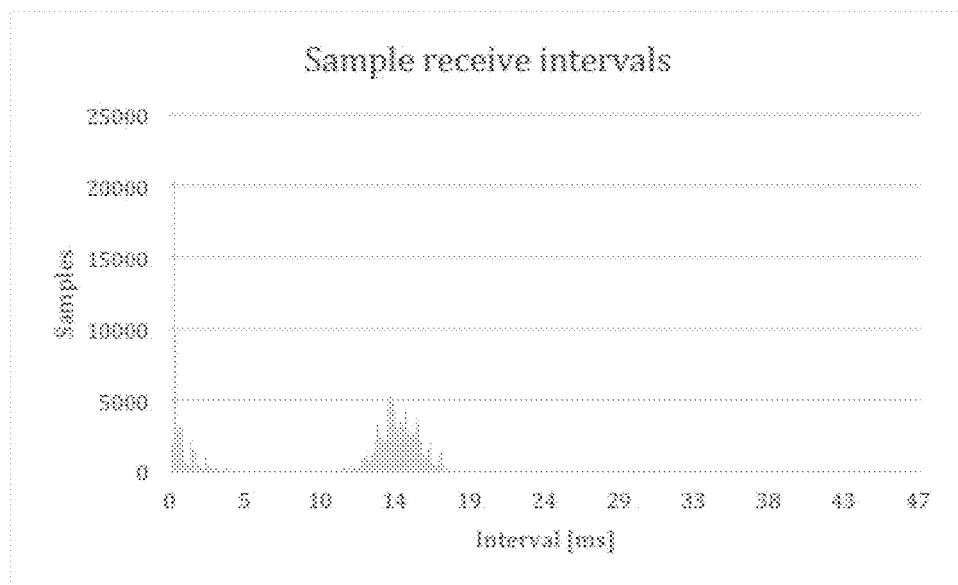

The BeatHealth sensors use off-the-shelf Bluetooth modules (see Section 3.4) whose buffer delays are not specified. As described in Deliverable 4.2 a method was developed empirically to estimate these buffer delays. This entailed configuring one Bluetooth module as the master and another as the slave. The same power source and clock source were used to drive both devices so that it was certain that the real time clocks of both devices (from which timestamps are obtained) were synchronized. Thereafter, the delays in sending data from slave to master were measured and this was used to form estimates of the buffer delay introduced by the sensors. FIG. 53 plots a histogram of the intervals between the received sensor samples on the Motorola Moto-G phone running the latest Android OS for a sensor sampling rate of 100 samples/second.

From FIG. 53 is can be seen that there are two clusters of intervals on the histogram, around 0 ms and just above 14 ms. A more detailed view of the sample timing is available by examining a subset of intervals between consecutively received sensor samples.

Figure 54:
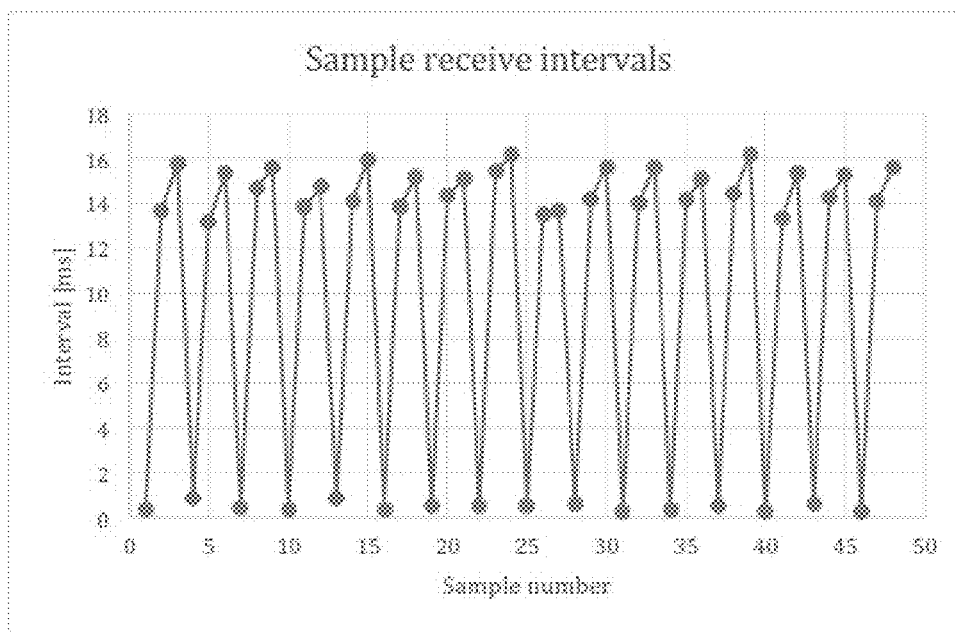

In FIG. 54 the detailed plot shows that the sample intervals appear to vary between approximately 0 ms and the vicinity of 15 ms. From both figures it is clear that the interval between any two consecutive samples at the receiving phone is not the 10 ms that would be expected for a 100 samples/second sample rate. However, it is worth noting that the sample interval averaged across many samples is of course 10 ms as would be expected. The observed intervals between received samples is consistent with the specified Bluetooth 4.0 GATT inter-connection intervals of around 15 ms and the fact that one or two packets are transmitted during each brief connection.

6.2. Measuring the Buffer Delay with the Windows 8.1 Client

As in Deliverable 4.2 the timing of sensors was also investigated with Windows 8.1 (used as the computer OS in the experimental trials). The tests were conducted using the same methodology as the Android tests with the Moto-G except that in this case the client software, which was responsible for receiving and logging the sensor samples, was running on Windows 8.1. The Windows 8.1 hardware platform was a MacBook Pro that had been booted into the Windows 8.1 OS so it was not running a virtual machine.

Figure 55:
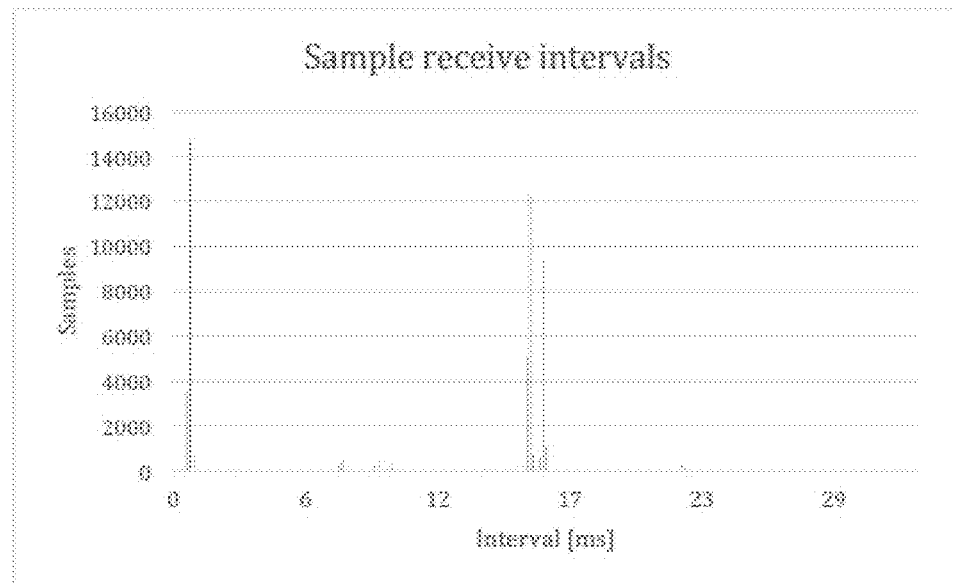

FIG. 55 shows the histogram of sample intervals which are very close to 0 ms and 15 ms. Additionally, the consistency of the sample intervals, particularly around 15 ms, appears to be much stronger than for the previous results with the Android Motorola Moto-G phone as the histogram peak is much narrower.

Figure 56:
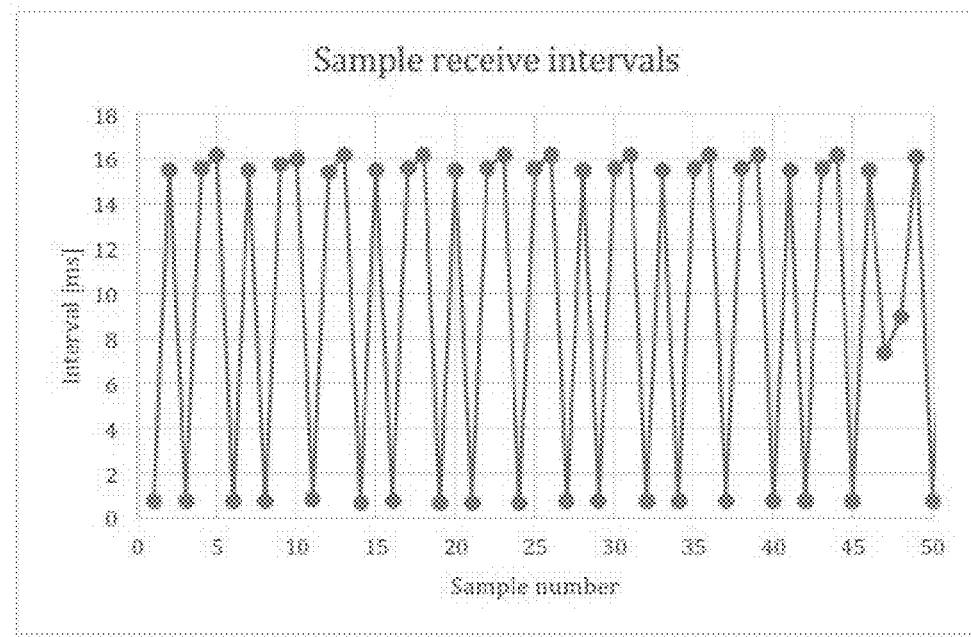

In FIG. 56 a detailed plot of a subset of consecutive sample intervals is provided. As would be anticipated following FIG. 54, the sample intervals appear to vary between two modes of approximately 0 ms and 15 ms. Unusually there are two samples at indices 46 and 48 with an interval of approximately 8 ms each. The results here match those in Deliverable 4.2 in that there is a more consistent pattern in the timing for the Windows 8.1 client than the Android client.

7. Conclusion

This Deliverable 4.7 has introduced the final BeatHealth physiological sensor system architecture. It explained the final design of the custom-made inertial sensors in detail and also discussed their enclosure and attached to the user. The selected Heart rate sensor was also mentioned. Experiments that examined sensor connectivity, physiological feature extraction from the sensor data, and the sample timing variability for the Android and Windows 8.1 systems were explained. There has been a marked improvement in the final design and the functioning of the inertial sensor since Deliverable 4.2. Its finished form is compact, portable, and has a generous battery life. The connectivity, in terms of number of simultaneous devices and packet losses, along with the sample timing variability figures are much better. A step detection algorithm has been implemented though this is still undergoing refinement and will be reported in final form in D4.8. The BeatHealth sensors have been manufactured and are now currently being prepared for the proof-of-concept experiments.

8. Future

Now that the BeatHealth sensors have been manufactured and exposed to more in depth use and testing it has become apparent that they may be satisfy a niche in the market due to relatively low cost, small form factor, and the integration of certain signal processing algorithms. It is worth investigating this beyond the lifetime of the BeatHealth project.

9. References

Companies
3DprintUK (2016). 3D printing service, from https://www.3dprint-uk.co.uk
CadsoftUSA (2016). EAGLE freeware, from http://www.cadsoftusa.com/download-eagle/freeware/
Delsys (2016), Wearable sensors for the movement sciences, from http://www.delsys.com
Invensense (2016). MPU-9250 Nine-Axis (Gyro+Accelerometer+Compass) MEMS MotionTracking™ Device, from http://www.invensense.com/products/motion-tracking/9-axis/mpu-9250/
Motorola (2016). The Moto-G third Generation Mobile phone, from http://www.motorola.com/us/products/moto-g
RFduino (2016). RFduino SMT Bluetooth Smart, from http://www.rfduino.com
Vicon (2016). Motion Capture technology, from http://www.vicon.com/home
Zephyr (2016). HxM BT—Wireless Bluetooth Heart Rate Monitor for Android & Windows Phone 8 from http://www.zephyra nywhere.com/products/hxm-bluetooth-heart-rate-monitor

JOURNALS

Madgwick, S.; Harrison, A.; Vaidyanathan, R. (2011). Estimation of IMU and MARG orientation using a gradient descent algorithm, Proceedings of the 2011 IEEE International Conference on Rehabilitation Robotics (ICORR), Zurich, Switzerland, 29 June-1 July, (pp. 1-7).
Morris, M. E., Lansek, R., Matyas, M. A., and Summers, J. J., (1996) Stride length regulation in Parkinson's disease. Normalization strategies and underlying mechanisms, Brain, 119 (2), (pp. 551-568).
Mahony R., Hamel, T., and Pflimlin, J.-M. (2008). Nonlinear complementary filters on the special orthogonal group, IEEE Trans. on Automatic Control, 53(5), (pp. 1203-1218).
Nilsson, J-O, Skog, Hari, I, K. V. S., and Handel, P. (2012). Foot-mounted INS for everybody—An open-source embedded implementation, IEEE/ION Position Location and Navigation Symp. (PLANS), Myrtle Beach, S.C.
Rampp, A., Barth, J., Schulein, S, GaBmann, K. G., Klucken, J., Eskofier, B. M. (2015). Inertial Sensor-Based Stride Parameter Calculation From Gait Sequences in Geriatric Patients, IEEE Trans. on Biomedical Engineering, 62(4), (pp. 1089-1097).

Part-5-Project-610633_Deliverable-4.6: Software Architecture;
Previous Reports and Deliverable Description Deliverable D4.6 is the final report on "BeatHealth Mobile Application". The BeatHealth application is manifested in two forms as BeatRun and BeatPark. This report reflects the culmination of work presented in previous deliverables:

D4.1 was an early report on the development of the BeatHealth mobile application
D3.1 and D3.2 described the development of the software tools for music and movement analysis for the BeatHealth application respectively.
D4.2 contained the initial work on building and integrating the hardware sensors with the BeatHealth Mobile Application.
D4.3 concerns integration of the data from the BeatHealth Application with the cloud platform
D4.4 explained the processes involved in the User Interface design for the BeatHealth Application
D4.5 explained the development of the Cloud services in detail.
D4.7 was a final report that detailed the integration of the movement sensors within the BeatHealth system.
D4.8 reported on the validation of timing and measurement in the BeatHealth system.

At the commencement of the project the requirements of the BeatHealth application were first specified as a detailed set of User Stories that were generated through extensive consultation with the members of the project consortium. These set out what the application should do in various scenarios. The initial high level design and its architectural features were produced initially. The decision to proceed with Android as the mobile development platform was quickly made. Additionally, the Csound audio library was chosen to implement the music playback and manipulation functionality because local expertise was available.

The high level design was translated to a skeleton prototype application. The stories of the highest priority were chosen in order to demonstrate a minimum viable version of the BeatRun app. The most important elements of this included (a) reading the internal sensors of the Android device, (b) integrating the Csound framework, (c) interaction with the Android media database to detect and play songs and playlists, (d) implementing an initial gait detection algorithm, and (e) including simplified versions of the music adaptation strategies. Two BeatHealth mobile app prototypes had been developed by the end of the first year.

During the second year a key development was the refactoring of the BeatHealth application architecture. This entailed dividing it into two parts, each having separate functional roles. Four music alignment strategies were implemented and the relevance of timing to the success of these algorithms motivated a focus on characterizing and compensating for audio latency, particularly in relation to the event to sound output latency. The step instant detection algorithm was replaced with an algorithm based on z-axis gyrometer only. Much work was also carried out on developing the User Interface (UI) for both the BeatPark and BeatRun applications. After much testing, the final versions of both applications had System Usability Scores in the vicinity of 75/100. Finally, with regard to the BeatHealth cloud service the architecture had been designed and significant parts of the implementation were completed.

At the beginning of the third year of the project the developer tasks were to finalise the implementation of the BeatPark and BeatRun application features and carry out extensive testing in preparation for the Proof-of-Concept (POC) trials of the project.

This document on the final version of the BeatHealth mobile application commences with descriptions of the architecture of the software. It then describes the functionality of both the BeatPark and BeatRun applications by referencing the various screens of each application as a guide. The next section then describes the new features that have been added to the application since D4.1. These reflect changes to the User interface, the addition of elements to enhance the user experience, the completion of the integration with the Cloud platform, and technical improvements that were integrated.

This is followed by a section that describes the variety of testing activities that the application was subject to. These covered all aspects of the application and were a necessary part of the software development process. Additionally, individual tests had to be created for the BeatRun and BeatPark applications that reflected their different functionality. After this, the report closes with a short conclusion.

BeatHealth App Final Architecture

FIG. 58 illustrates the final overall architecture of the BeatHealth mobile application in the forms of BeatRun and BeatPark. While the application interfaces are understandably different to each other, the core services both use functionality from the same software library. This was the most efficient system design approach to have, particularly with regard to code production and testing. It reflects modern best practice in the software industry. As stated in the introductory section, this system architecture had evolved to this final state during the second year of the project. This meant that is was already in a stable architectural state well in time for the 'Proof-of-Concept' activities.

Figure 59:
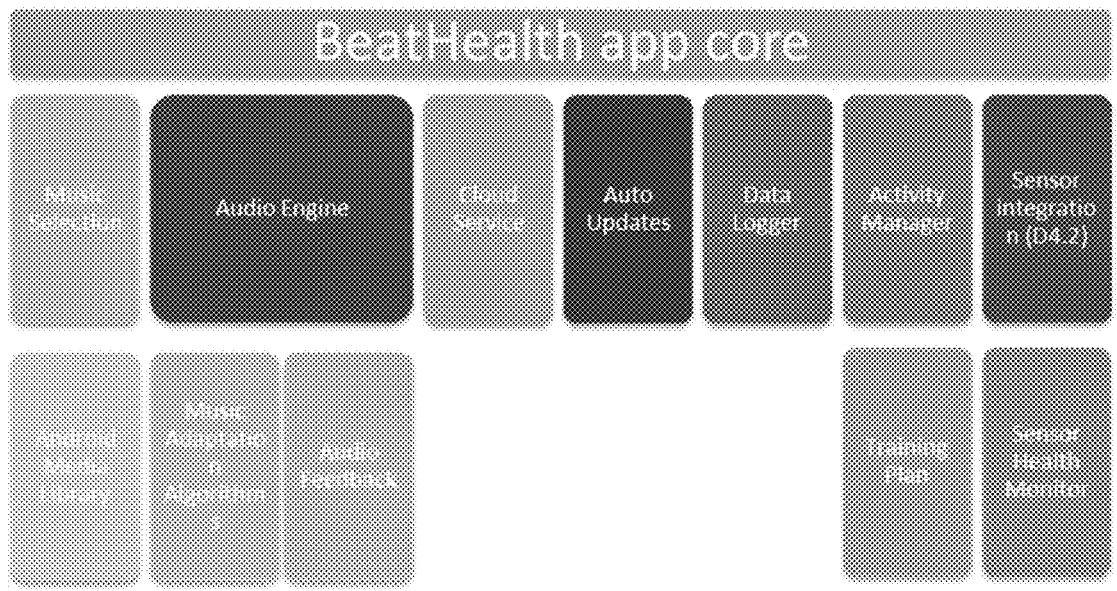

The diagram in FIG. 58 can be expanded with more detail and this is shown in FIG. 59. In this Figure the 'BeatPark App' and 'BeatRun App' blocks of FIG. 58 are represented by the 'User Interface and Control' block in FIG. 59.

This User interface sits on top of the essential components of the BeatHealth core. This core consists of: 1) the music selection system, 2) the audio engine and associated processing, 3) the cloud service, 4) the auto updates module, 5) the data logger module, 6) the activity manager, and 7) the sensor integration component.

The music selection component is driven by the music adaptation algorithms and interacts with the Android Media Library and audio engine to ensure that tempo-appropriate music is played.

The Audio engine encapsulates the low level details of the interaction with the Csound engine. It interacts with the Music adaptation algorithms, the Android Media library, and the Audio feedback module. The Android Media Library is an Android API for interacting with music files. The audio feedback module provides real time coaching through headphones during the BeatHealth sessions giving updates on activity status (started, paused, resumed, stopped) and time remaining.

The cloud service allows uploading data collected during session to the server. The auto updates module is a facility for developers to upgrade the application with enhancements and bug fixes without the necessity for manual software installation by the user. The data logger module is responsible for collecting and storing necessary data collected during activity locally on the phone (internal memory). The Activity Manager coordinates BeatHealth activities such as session duration, and the enabling/disabling of music. The Training plan module facilitates the implementation of the training sessions. Finally, events from the sensor integration component (such as detected footfalls and cadence information) drive the music adaptation algorithms.

2.1 Functionality of the Mobile Applications

A very good way to illustrate the functionality of BeatPark and BeatRun is through images of the succession of User Interface screens as a user would navigate through the application. More detail on the rationale behind the design of the screens in available in D4.4 on the User Interface.

Functionality of BeatPark

Figure 60:
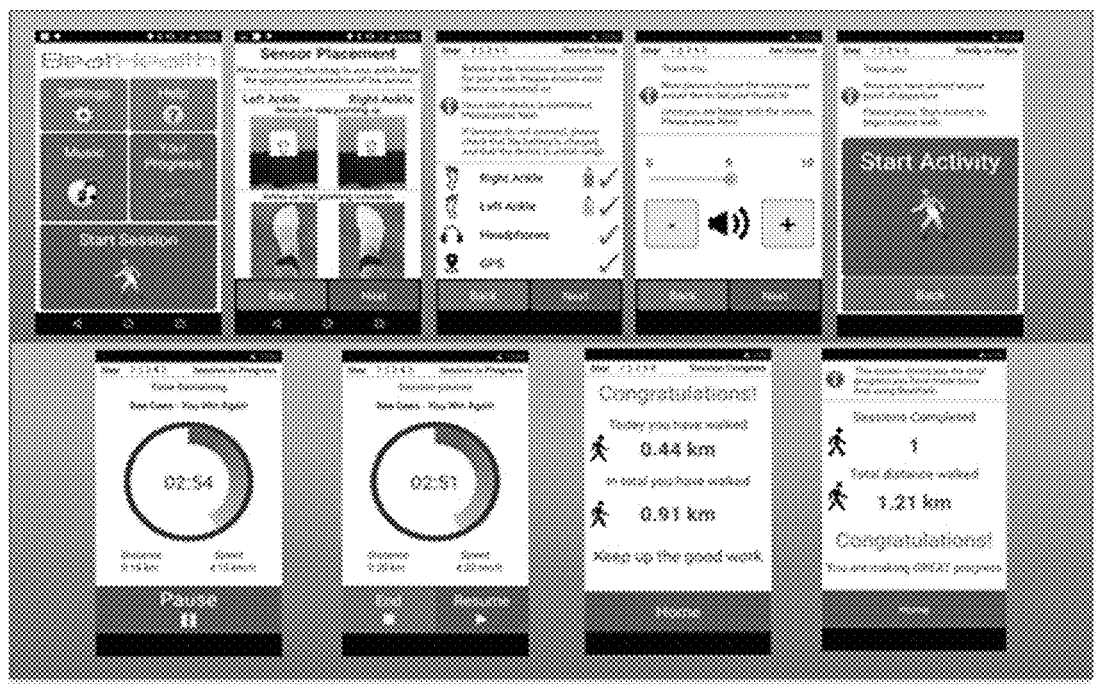

FIG. 60 shows the main sequence of user interface screens for the BeatPark application.

Figure 61:
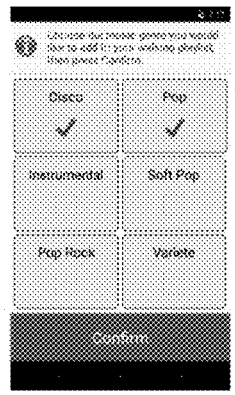

BeatPark was designed to present an easy-to-use touchscreen interface as it was acknowledged that users could have difficulty otherwise. Large buttons appear everywhere, for example the layout of the first screen in FIG. 59 has five buttons with icons and clear big text. In particular, the button to start the BeatHealth training session is large and is prominently placed at the bottom of the screen. The other buttons allow the user to access options to change settings and choose the music genres that they will listen to. For example, if the user touches the music button the screen shown in FIG. 61 is presented. The user can choose between genres of Disco, Pop, Instrumental, Soft Pop, Pop Rock, and Variete. A selected genre is given by a green tick mark on the relevant button. Multiple genres can be chosen at the same time.

Once the start session button is pressed the user is then presented with an information screen that shows then how to place the sensors correctly on their feet. This was a recently added, helpful reminder in order to prevent errors in sensor placement and was based on user experience and feedback.

The next screen in FIG. 60 shows the user that the sensors have established a communications connection with the phone over bluetooth, the headphone has been attached, and the GPS capability on the phone has been switched on. Additionally, on this screen there are icons for each sensor to show how much battery charge remains.

Figure 62:
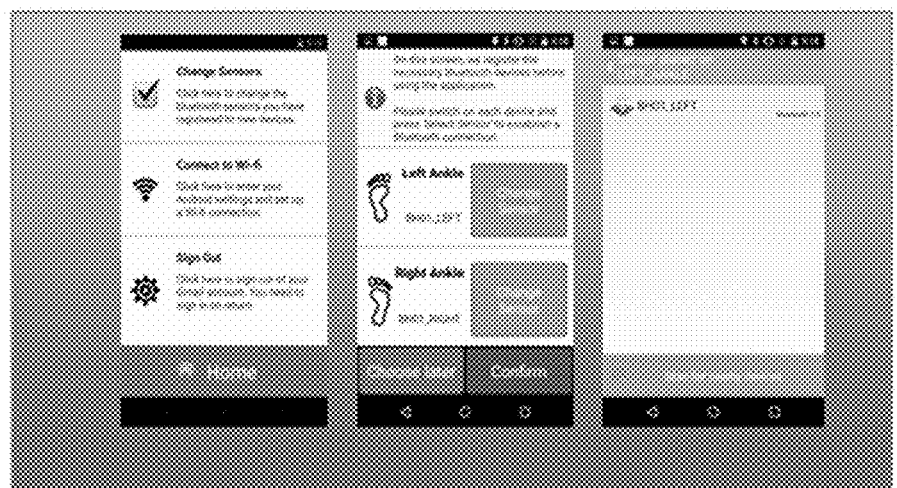

It is worth noting that users are given phones with a particular pair of sensors that have been registered in advance with the application. Thus, there is no specific need for the user to make any changes to this. However, it is possible for the experimenter to do this and they can do this using the settings button on the first screen in FIG. 60. If they do this the screens shown in FIG. 62 are shown. They will select the change sensors amber checkbox for the relevant sensor. They then can select the ankle for which they want to change the sensors which appears on the second screen. On pressing this button the application with search for nearby sensors and shows them as a list to the user from which they can pick the one they want. This screen appears on the far right of FIG. 62.

Returning to FIG. 60 the screen following the one showing the sensor battery charge simply allows the user to set the most comfortable volume level. After this they are presented with a large green button to indicate that they will now start the training activity. Audio feedback prompts are also given to the user. The reason for this is that during an activity session the phone will most likely be placed in a holder on the arm or in the pocket on a belt. The user would then have some difficulty checking the session status or time remaining while moving. The prompts, issued at specific intervals, were found to be a convenient way to provide updates to the user.

The activity screen shows a large circle with a clock in the centre counting down to the end of the session. A concentric animation is given to graphically illustrate the time taken so far. This is coloured as a transition band from red to yellow. The name of the track is also given on the screen along with the distance travelled and current speed of the user. The user can pause the session at any point if they want using the large pause button at the bottom of the screen. If this happens they are given the next screen which allows them to resume the session or end it. Audio feedback prompts appear throughout the session to let the user know how much is remaining. An audio prompt is given when the session ends and the user is shown the second last screen in FIG. 60. This tells them how much they walked in this session along with the accumulated distance they have walked over all sessions. A motivational word of 'Congratulations' in red lettering is shown too. The final screen is very similar to this but lists the number of sessions completed and the accumulated distance walked.

It is worth noting that red buttons are given on all screens to allow the user to go back to the previous screen, or end the application if desired. The use of green and red for buttons in the application draws on the common associations of these colours.

BeatRun Functionality

Figure 63:
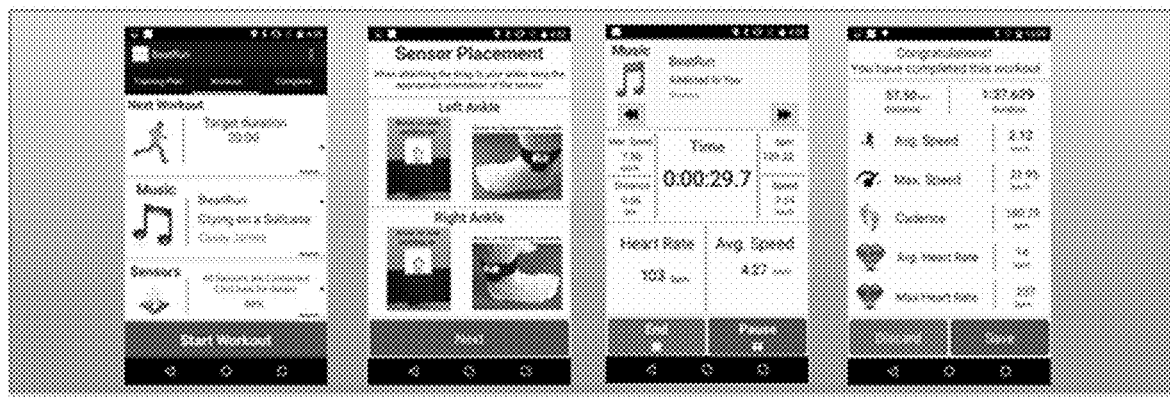

The main sequence of screens in the BeatRun Application is shown in FIG. 63. It can be seen that it is somewhat different to those for BeatPark in FIG. 60. The initial screen of BeatRun tells the user about the duration of their next training session, the next music track that will be played, and sensor connectivity. Touching on these panels will bring the user to the Music genre selection screen, which is identical to the one for BeatPark shown in FIG. 61, or the sensor information screen, shown in FIG. 64.

Figure 64:
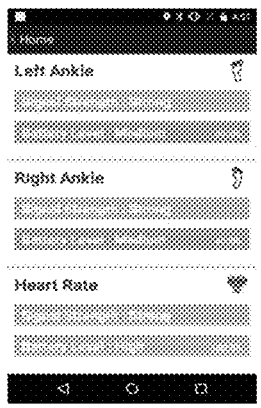

This screen in FIG. 64 provides the signal strength between each sensor and the mobile application, along with the level of battery power remaining. Colour coding or red, amber and green it uses to highlight low, medium and strong respectively. To return to the first screen the user must tap the back icon at the very bottom of the screen.

Figure 65:
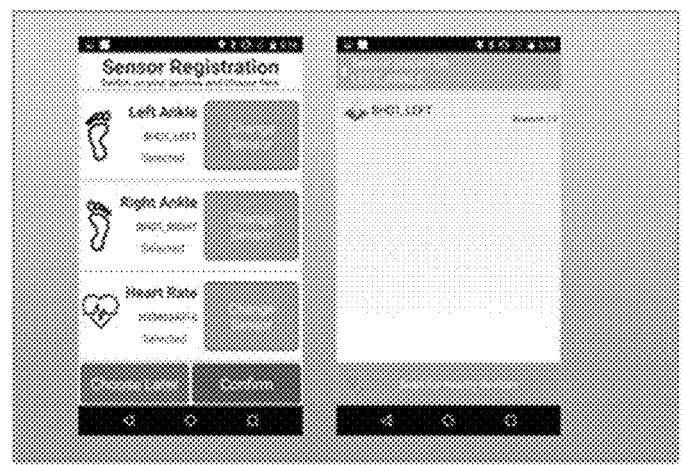

If the user wants to change the sensors interacting with the application they have to enter the application settings section at the very top of the screen and then select sensors from the menu. The screen then appears as shown on the left in FIG. 65. To change a sensor the user taps the amber button for the relevant sensor. In the right-hand panel of FIG. 65 is the sensors detected screen within which all Bluetooth devices within range of the mobile phone are listed. Here, the assignments for the ankle worn motion sensors can be changed as well as the heart rate sensor. It is almost identical to the procedure for BeatPark shown in FIG. 62 except for the inclusion of the Heart Rate sensor. When a sensor is selected it returns automatically to the left hand screen of FIG. 65. The user can either 'confirm' their changes by pressing the green button or exit this part of the application by pressing the red 'confirm later' button.

Figure 66:
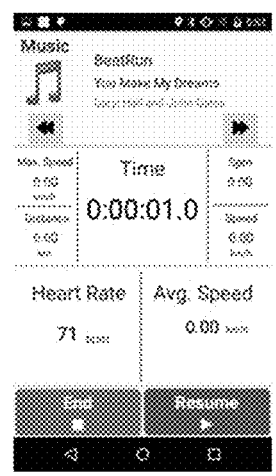

Returning to FIG. 63 it should be pointed out that there are tabs at the top of the main screen to facilitate a form of navigation through the app. When the user touches the start workout button they are first presented with the sensor placement information screen. Following this they have the workout screen. This displays the name of the music track currently playing on the top. It has the time taken at the very centre of the screen. At either side of these are numerical values telling the maximum speed and distance travelled (in the left-hand panels) and the steps-per-minute (SPM) and speed in units of km/hour (in the right-hand panels). In the two larger, lower panels the Heart rate and the Average speed are displayed. At the very bottom of the screen are buttons that allow the user to end or pause the application. Pausing results in the screen shown in FIG. 66 which essentially freezes the application until the resume button is pressed, or quits if the end button is chosen.

Finally, beside the name of the song at the top of the screen are controls that allow the user to move back and forth along the playlist in case they want to repeat the previous track or skip away from the current track. This functionality is not available in BeatPark and the audio track playback is fully automated.

When the training session is complete the next screen in the sequence is a user information screen that lists the values including the average and maximum speeds, the average and maximum heart rate, and the cadence. This information is saved on the phone no matter if the user selects the 'Discard' or 'Save' buttons and is simply tagged as being "saved" or "discarded". The purpose of this is to ensure that all data is available, even in the case of the user discarding in error.

The next screen the uses sees shows the Borg rating scale of perceived exertion (Borg, 1982). This is a well-known system used to assess how heavy and strenuous the exercise feels to the participant, and it intends to find a single rating value that integrates all sensations and feelings of physical stress, effort, and fatigue. The scale ranges from 6 to 20, where the number 6 corresponds to "no exertion at all" and 20 is "maximal exertion". This screen is shown in FIG. 67. It is colour coded to allow the user to differentiate across the scale. The user simply touches the screen at the level they think is appropriate.

After this screen a final survey questionnaire screen appears as shown in FIG. 68. It is in the Flemish language for the participants in the POC trials at UGhent. It is actually a separate application that was developed by the partner UM and was integrated as a final stage in the BeatRun application by NUIM.

The questionnaire is based on the Physical Activity Enjoyment Scale (PACES) (Mullen et al, 2011). It has 8 factors as can be seen in FIG. 64. The user adjusts the sliders to rate how they agree or disagree with 8 adjectives describing their running session, as can be seen in FIG. 64. The left and right limits of the sliders are "totally agree" and "totally disagree" respectively. The distance from the right limit of the scale to the cursor location was recorded for each and then all 8 are summed to calculate the final score. A higher PACES score reflects greater level of enjoyment. Once this is complete the app then returns to the starting screen automatically.

If the user touches the Training Plan tab at the top of the starting screen shown in FIG. 63 the screen shown in FIG. 69 appears. This screen allows the user to investigate the settings and the progress for their particular training plan.

New Features Integrated into the BeatHealth Application

As stated in the introduction a number of additions were made to the application since D4.1. These are explained in the next sections.

UI Changes

A number of improvements were made to the UI. The subsections below mention each of these.

Delivery of Audio Feedback to User at the Beginning and End of Each Session

As the BeatPark and BeatRun applications should be usable without the user constantly looking at the phone display it was decided to include audio feedback to the user throughout the training session. It would mean that the user could place the mobile phone in a pouch that was attached to their arm or belt and could discover the status of the session they were engaging in without having to look directly at the screen. This feedback took the form of short sentences telling the user (delivered via the headphones) that the session was starting, noting when the session was halfway complete, stating if the session had been paused or resumed, reminding that it was close to finishing, and then finally acknowledging its completion.

The audio feedback module was implemented using Google's text to speech engine which synthesizes speech from a text input on the fly. Two languages are supported in BeatPark and BeatRun at the moment (English and French) but application can be updated to support other languages supported by Google.

Borg and User Satisfaction Screens

As mentioned in Section 2.2 at the close of the BeatRun application there are two questionnaires presented to the user in succession. The first is based on the Borg scale (Borg, 1982) and the second is based on the PACES scale (Mullen et al., 2011). The intention was to capture some extra information from the user about the application. In comparison to the purely objective numbers such as the distance travelled and the average speed, these can be used to assess the subjective impressions of the training itself (Borg) and the application (PACES). It should be noted that the PACES questionnaire is a separate application that was implemented by UM but is called by BeatRun at the very end of a session. The user interface design, as shown in FIG. 67, is clearly of a simpler and monochromatic design in comparison to the BeatRun interface.

Sensor Placement Screen

During application testing it was found that some users were confused about the correct way to position and orient the sensors on their ankles despite having received training on correct positioning and orientation beforehand. When the sensors are not oriented correctly it can produce bad or even unusable data. The sensor placement screen (see FIG. 60 and FIG. 63) was added to address this problem by encouraging the user to check that the sensors were positioned correctly before they started their training session. The use of actual photographs, colour coding and a minimum of text was to ensure to be explicit about what the user should do.

Display of SPM on the Workout Screen

The Steps-per-Minute (SPM) display on the workout screen was made to be configurable. Thus, it could be enabled via settings or dynamically by the training plan functionality. In particular, it was felt that it should not be visible to participants during the proof of concept of experiments.

Enhanced User Options

During the third period of BeatHealth a number of new features were introduced or existing features modified based on real-world testing with the app, refinement of the proof of concept experimental protocols and other factors.

Genre Based Playlist

In prior versions of the app the music to be played during a session (or a number of sessions) was chosen by selecting a playlist that had been prepared in advance. No user interface for editing or customizing the playlist had been developed for the app and it was felt that such an interface could be too complex for BeatPark users. For this reason it was decided to provide a user interface to choose music by genre only. The app would then select songs of the appropriate tempo from the chosen genres at run time depending on the user's cadence. Although BeatRun users were expected to be more comfortable with smart phones and mobile app user interfaces it was decided to use the same user interface style for choosing music in BeatRun also.

Special Versions Associated with the Training Plans

Different training plan and activity management implementations were developed for BeatRun and BeatPark. In the case of BeatRun, the proof of concept protocol required a number of sessions of pre-training activity, fixed and adaptive music activities in addition to pre-test, mid-test, and post-test sessions. The training plan implementation determined when to switch music alignment algorithms and settings and whether individual participants should do fixed music tempo first or adaptive music alignment first. The plan also protected the pre-test, mid-test, and post-test sessions so that participants could not progress until approved by an experimenter. During each activity, the activity management feature in BeatRun manipulated the duration of session, the visibility of cadence information, and the disabling of music when appropriate.

Integration with the Cloud

For much of the project the cloud platform was designed and developed in parallel with the mobile app. During the third period the two systems were integrated so that data generated during sessions of the proof of concept experiments would be synchronized with the cloud platform. From the cloud platform, experimenters could retrieve data for early analysis and to confirm that participants were adhering to the training plan.

The cloud integration was achieved by integrating a library that handled temporary storage of information to be synchronized locally on the phone and a custom android service that synchronized the information once internet connectivity was available.

Although there are some minor differences in the information to be synchronized between BeatPark and BeatRun the data to be synchronized was largely the same and fell into the following categories:

1. User profile
2. Session characteristics
3. Gait related data
4. Heart-rate data (BeatRun only)
5. GPS tracking Technical Updates A number of updates to the technology of the application were made since D4.1. These are described here to highlight that they have been completed.

GPS to Measure Speed and Distance

Since GPS detection only works effectively outdoors, a GPS signal is only used with the BeatRun application to detect user speed and the distance they have travelled. This had been planned for the application from the beginning but was only integrated during the third period.

Figure 70:

The GPS information captured during a session is part of the overall dataset stored locally on the phone and on the cloud platform. FIG. 70 illustrates the GPS data highlighting a runner's trajectory that was recorded from a run on a track in Montpellier during the validation experiments.

Step Detection Algorithm

Figure 71:
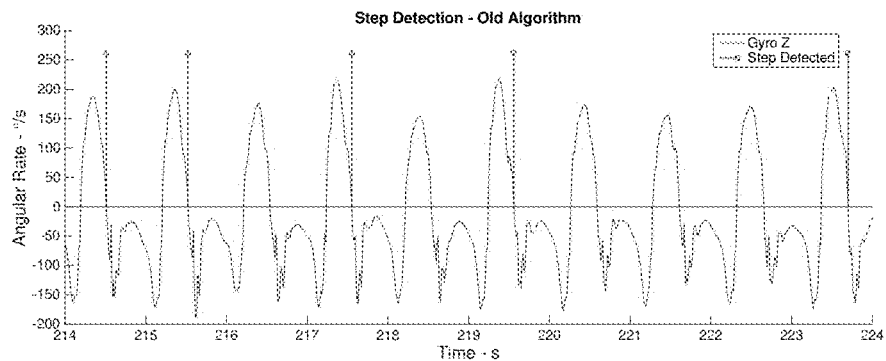

Strictly speaking the step detection algorithm is part of the sensor integration layer that would have been described in D4.7, but changes were made since that document was written and are included here for this reason. Initially the step detection algorithm used in the application had been derived from the D-Jogger platform of UGhent. Early tests of both BeatPark and BeatRun indicated some problematic situations in which not all the steps were registered or false steps were identified. FIG. 71 shows an example in which a number of steps have been missed.

A modified algorithm was developed that redefined the heuristics under which a step was counted. This resulted in an improved duration of detection time-window and a better threshold value within which a step could be found.

Figure 72:
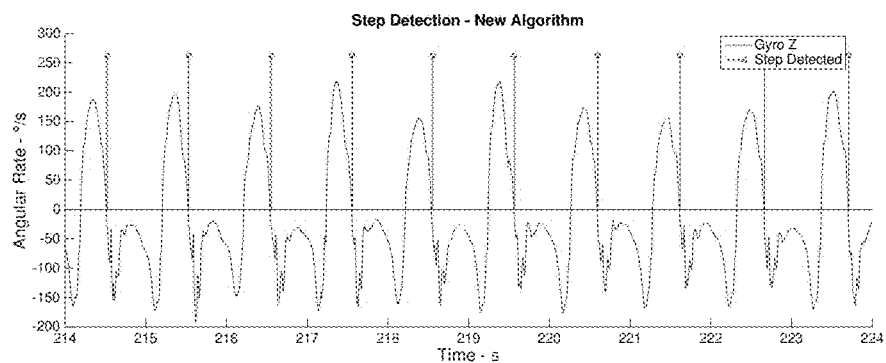

FIG. 72 shows the output of the improved algorithm applied to the same data. On this occasion all the steps are now identified.

Target SPM Measurement

The design of the BeatRun proof of concept protocol specifies that a target SPM should be set individually for each participant based on their capabilities and this target is then used by the music adaptation algorithms during the experiment. To facilitate this, the protocol calls for a pre-test during which the participant's cadence is measured and a specialized activity control was developed to support this. Specifically, during the cadence measurement pre-test the candence is measured for 3 minutes after an initial 1 minute period without measurement. The filtered average value from the measurement period is then used with the alignment algorithm.

Application Auto Update Module

To be able to keep BeatPark/BeatRun application up to date and allow developers to push remotely any enhancements and bug fixes, an auto update module was integrated with the application. Every time the BeatPark/BeatRun application is launched, a check is made to discover if a new update is available. If this is the case, the user will be notified and asked to confirm that they want to download it. The application will then download the updates in the background, allowing the user to continue to use it in an uninterrupted manner. After the download is complete, a notification appears in the notification area with a message that the updates are ready to be installed. The user can then install the new updates in several simple steps by tapping the notification message.

In addition, users can check manually if there are new updates available by tapping on the appropriate option in the application settings.

All updates for BeatPark and BeatRun are stored on the server at NUIM. There are separate folders on the server for the BeatPark and BeatRun live updates. Whenever a new update ready for release the developer will compile the new application software with an incremented version number and then upload it to the server. Separate test folders also exist on the server with updates for BeatPark and BeatRun that can be used by developers to test new features before they are generally released to the other partners of the consortium team.

Testing of the BeatHealth Application

This section describes the testing of the application. This is not to be confused with the validation procedures whose purpose was to ensure that the measurements made by inertial sensors agreed with ground truth recordings that were made simultaneously using state-of-the-art equipment.

The subsections below describe the testing of key features and the overall system. The general procedure adopted was to test the system and then release a version of the app to partners for testing or use. If partners reported issues these were investigated and the app was modified if necessary. In the case of any modification, regression testing was performed to ensure (insofar as possible) that the modification did not introduce any new problems itself.

Testing the App Over a Complete Training Plan

As the time for the POC trials drew closer it was acknowledged that in order to make sure the software worked for full sessions and full training plans testing was required. The aim of these tests was not to test individual features of the application per se, but to test the flow of the application through the sessions and ensure that full sessions and full training plans could be completed using the application without issue. At NUIM full individual sessions were tested for both BeatPark and BeatRun applications. Following these, a member of the team tested the BeatPark app over a full training plan with full-length sessions. In both cases no faults were discovered.

Regression Testing

It was the policy of the development team to engage in Regression testing after every major software bug fix or upgrade. This meant putting the application through an established sequence of Regression tests to ensure that the software change did not damage the application. This consisted of installing the application on the mobile platform and the tester using the application for the full duration of physical trial. Two types of Regression test were carried out: (a) single sessions of a typical duration (of the order of 20-30 minutes), and (b) a full training plan of short sessions (with each session being of the order of 3-5 minutes). This flexibility was necessary to gain the most efficiency from the test procedures with a minimum of compromise.

Testing App Features

Particular features of the application required testing that was outside the typical desk-oriented procedures of software testing. The cases where this feature testing occurred are given in the next subsections.

Testing the Audio Tracks and Playlist

The audio tracks and associated meta-information were provided by the partner UGhent. They had to be tested to ensure that (1) the audio track and its meta-information matched, and (2) that the audio track mp3 file played correctly. This had to be done manually by checking all the files, and opening them in a digital audio playback program to ensuing that they played properly.

Testing the Run-Time Music Selection Algorithm

On the phone, the run-time music selection algorithm executes whenever a new song must be selected from the music database such as when a user chooses to go to the next song, when the currently playing song ends, or when the user cadence increases or decreases too much for the currently playing song. It was necessary to test that the algorithm correctly selected a song appropriate to the user cadence, that the order of songs was shuffled for each session, and that, in as much as possible, the same song was not played twice during a single session (song repetition).

Figure 73:
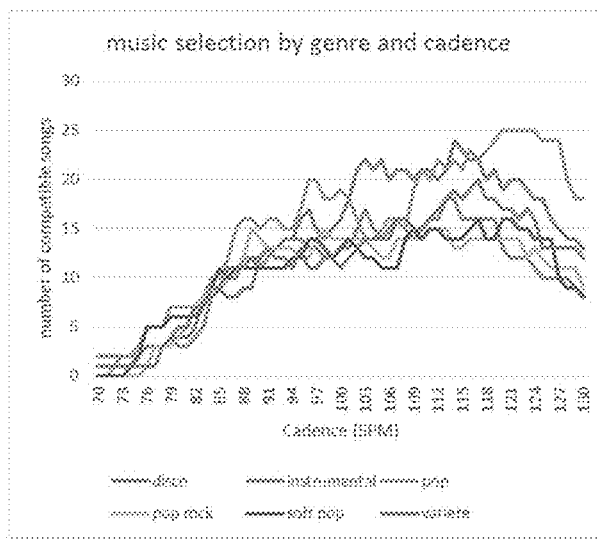
Figure 74:
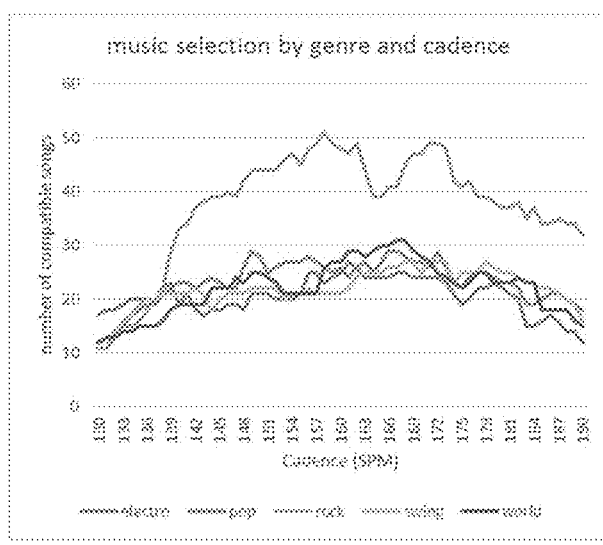

Song repetition can occur if there are insufficient songs in the music database that will be selected by the music selection algorithm for a given cadence and it is sensitive to both the algorithm and configurable parameters which control it. It was agreed that all users would be required to choose at least two music genres (and they could choose more if so desired). Therefore, offline analysis was performed of the music databases for BeatRun and BeatPark to evaluate how many songs would be chosen by the music selection algorithm in each genre at each cadence value as shown in FIGS. 73 and 74.

Since at least two genres will be selected, the key feature to examine in the figures is the two minimum values at each SPM. These minimum values indicate the worst case scenario with regard to the number of songs that can be played before repetition will occur. The music selection algorithm parameters have been chosen to provide a reasonable tradeoff between the number of songs available for selection and the maximum amount of tempo modification that will be applied to the song (because larger tempo modifications are more likely to introduce artifacts).

The figure shows that BeatRun has a minimum number of more than 20 songs no matter what pair of genres or SPM is chosen. BeatPark satisfies the same criterion above 90 SPM but below this value and particularly below 80 SPM the number of songs from a pair of genres may be 10 or fewer. Nevertheless, ten 3 minute songs correspond to 30 minutes and it should therefore be unusual for songs to be repeated within a single BeatPark session, even for participants with slow cadences.

Testing Alignment with a Step Simulator Sensor

To simplify the process of testing music alignment in a repeatable manner a number of step simulator sensors were constructed. Unlike normal sensors these sensors did not detect steps based on human motion but instead generated simulated step "detections" at intervals that could be controlled. The variability of the intervals could also be controlled which was useful for some tests. Later versions of the step simulator sensor included a dial so that the duration of the intervals (and hence the SPM) could be easily controlled.

The simulator sensor was connected to piezo speaker so that it emitted an audible 'pip' sound at the precise moment that a step was simulated. The BeatHealth apps were configured to use a specialized music database comprising a small number of carefully prepared songs that contained metronome-like 'pips' at specific intervals. The audio frequency of the metronome pips was specified to be different than the frequency of the step simulator pips so that both pips could be distinguished.

To test the alignment of the music on the phone (metronome-like pips) with moment at which step detection was simulated on the sensor (sensor pips) audio recordings were made and analysed. This analysis was used to refine the latency correction process. Time-frequency plots from two extracts of a recording taken when the latency correction task had been completed can be seen in FIG. 64.

Figure 75:
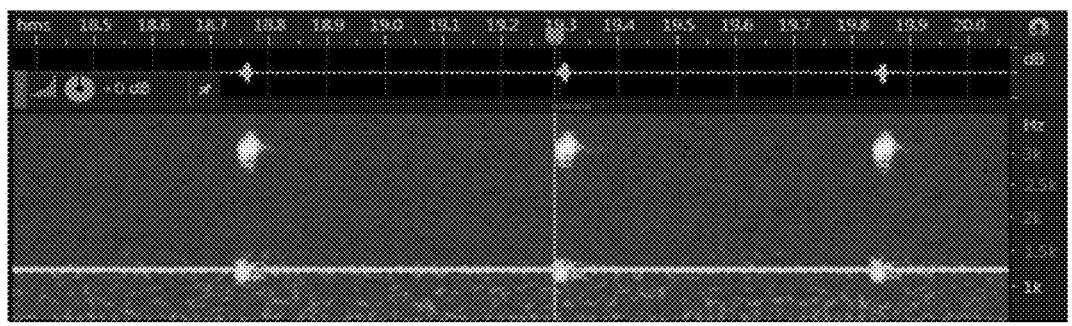
Figure 76:
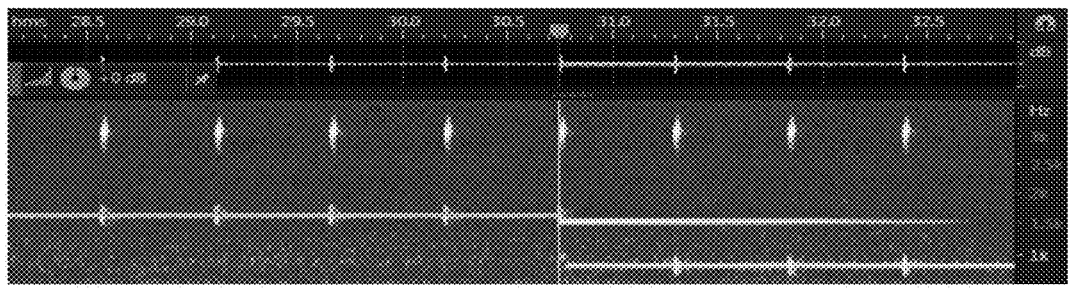

It is clear in the FIGS. 75 and 76 that the onset of acoustic energy aligns well. In fact the alignment of music is generally to within 10 ms of the simulated step which is well below the perceptible threshold of detection for asynchrony.

Testing the Alignment Algorithm

The correct operation of music alignment (in accordance with the predicted behaviour) was tested separately for BeatPark and BeatRun using data collected from test sessions. The test consisted of performing a test session using the app and then examining two key metrics during a consistent portion of the session where the cadence was relatively stable: (1) the difference between the participant cadence and the music tempo and (2) the difference between the step phase and the musical beat phase. The expected results were that the cadence tempo difference should be negligible on average and the phase difference should be stable and have a value predicted by the algorithm when applied to simulated or offline data.

Figure 77:
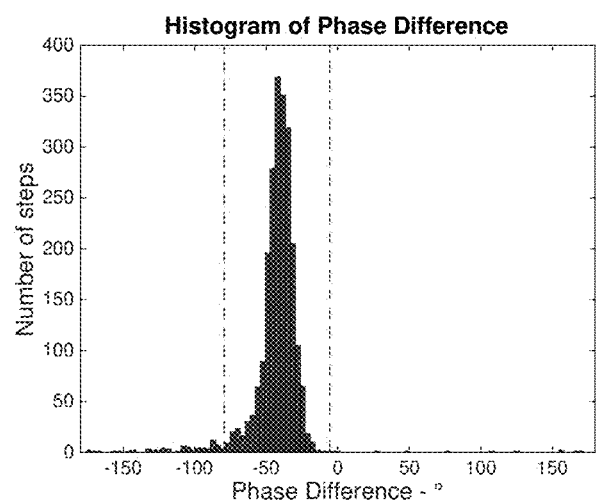

Considering BeatPark first, FIG. 77 shows the difference in phase between the estimated heel strike time and the annotated beat time of the music. In this case the measured mean is −42.7 degrees which agrees very well with the expected value −43.0 degrees in this test. The distribution of phases in the histogram is a result of normal human step interval variability.

Figure 78:
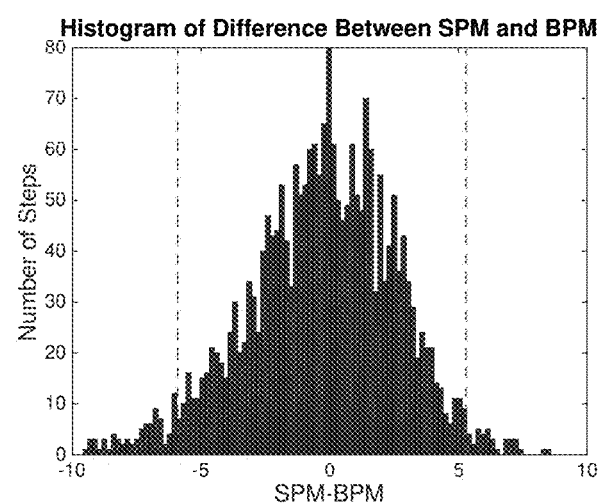

The cadence (SPM) to music tempo (BPM) difference is shown in FIG. 78. This shows a Gaussian-like distribution with a mean of zero. When the algorithm adapts the music it speeds it up or slows it down on very brief time scales which are usually not detectable to the participant in order to achieve the desired music alignment with the foot steps.

Figure 79:
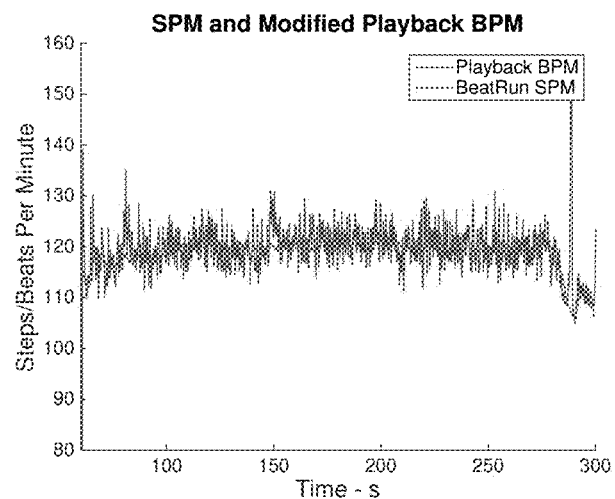

FIG. 79 gives an indication of the dynamic relationship between the SPM and the changing playback BPM over a 5 minute period.

Figure 80:
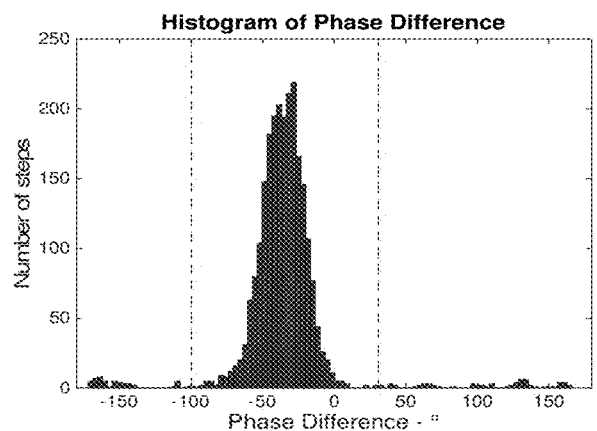
Figure 81:
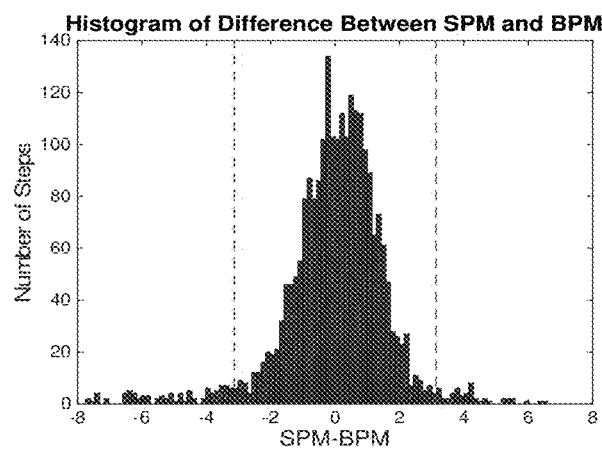
Figure 82:
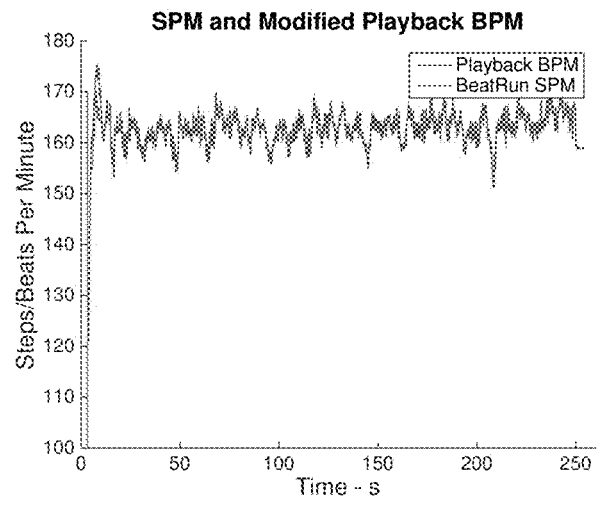

Similar plots are given for BeatRun in FIGS. 80 to 82. FIG. 80 is the histogram difference in phase between the estimated heel strike time and the annotated beat time of the modified music file for BeatRun. In this case the measured mean phase difference is −34.4 degrees which compares well with the expected value of −33.4 degrees.

FIG. 81 illustrates the cadence (SPM) to music tempo (BPM) difference. Again the mean is very close to 0. The SPM differences are smaller here than for BeatPark due to very different algorithm parameter values that have been used for BeatRun relative to BeatPark.

The final FIG. 82 shows the dynamics of the alignment between the SPM and the modified BPM. In the plot over the complete time period of approximately 4 minutes it can be seen that they match each other very well. This closer matching of SPM and BPM is again due to the different parameter values used for BeatRun relative to BeatPark.

Testing the Improved Step Detection Algorithm

The improved step detection algorithm was subjected to a thorough regression testing with all the validation data before being accepted. In the absence of ground truth for step detection fluctuations, the time difference between steps were used to identify missed steps, along with visual confirmation of the step in the z-axis data for the gyroscope. Once the changes were integrated into the app the app was then fully tested by the team members at NUIM. The resulting test outputs—step detection, SPM estimation, and alignment (listening to music while testing and inspecting the alignment log after each test)—were examined carefully. Improvements in the steps found were found for all regressions tests and no new steps were lost. In addition, estimated step timing was unaffected when checked against the validation data. The application worked as expected after integration of the improved algorithm and so the changes were accepted to the application.

Cloud Integration and Synchronisation Testing

To verify the functional, performance, and reliability requirements cloud integration testing was performed on the cloud software module of the application. The cloud application was developed by the partners in Tecnalia. This had to be integrated with the BeatHealth core developed at NUIM (as illustrated in FIG. 1). The interaction between Technalia and NUIM to produce the cloud software meant that the process of testing the software had to be managed carefully. Every time where new update or feature was released by Tecnalia, NUIM had to integrate it with BeatHealth Core and then test it. To make the testing of cloud service efficient before it could be fully integrated with BeatHeath Core a simplified setup was created that removed all unnecessary software modules. Simulated parameter values and session data inputs were generated for testing. All changes to the cloud module were first tested using this setup. In addition, simulated values were also used in the testing of the usage of shared data areas and inter-process communications. Later when the cloud module was ported to the full version of the BeatPark and BeatRun applications it was tested again using live data and a number of live walking/running sessions were performed. After each finished session the data generated was uploaded to the cloud and later compared with the data stored locally on the phone for verification purposes. A number of different scenarios were investigated:

1. The behaviour of the application software in situations where there is no internet connection available just as the session is finished and the user tries to upload data to cloud.

2. The behaviour of the application software in cases where there are a few sessions stored locally because the user didn't have access to the internet on those occasions, and they all now need to be uploaded together.

3. The behaviour of the application software when there is an interruption during the upload process.

Tecnalia also performed their own testing to ensure that the data generated by the applications were being saved on the cloud and that this procedure was happening in a synchronous manner. In order to test the correctness of the session data synced, demo applications were developed at Tecnalia that would sync randomly simulated session data. This allowed testing of every single part of the entire session.

Once the data was on the cloud, visualization software was used to confirm that the data was consistent with that sent by the phone. In addition to this visual check, a testing module was developed by Tecnalia for the demo application that compared the simulated and transferred data against the same information that was downloaded back from the cloud. In this way both communication directions were tested. This test was automated and run 100 times (100 cycles of session data uploads and downloads) with an accuracy result of 100%.

Testing the Automated Update Procedure

A number of separate folders were created on the NUIM server which had been allocated for testing of the application's automated update procedure. To test if new updates have been installed properly the steps are as follows:

[1] Compile the new BeatPark/BeatRun application with the latest version number.

[2] Upload to the server the new BeatPark/BeatRun application file with an additional file that contains the version number of this release.

[3] Go to BeatPark/BeatRun application settings and modify the auto updates folder path to be the one that was set aside for testing.

[4] Restart the application, connect to the Internet, and check for any new updates.

[5] If it is operating correctly, a notification message should appear with information that new update is available.

[6] Next, following the instructions to download the new update, install it, and restart the application.

[7] Finally, it must be verified that the settings have been preserved from the previous version.

Conclusion

The most important conclusion to be drawn is that the BeatHealth system has been successfully implemented as a core technology (that may be exploited) and custom apps that are built on top of that core for two very different populations of users: BeatRun for healthy runners and BeatPark for people with Parkinson's Disease. In particular, all the key technologies and algorithms developed by the consortium have been integrated into the mobile app resulting in a successful culmination of many years work by all partners on the project. Both apps have been successfully deployed to many users participating in the proof of concept experiments for BeatRun and BeatPark.

In this final report the architecture and functionality of the final version of the BeatHealth application in both its forms as BeatPark and BeatRun has been described.

Particular attention was drawn to the many new features that were included in the application since deliverable D4.1 was written. Finally, selected aspects of the testing procedure were described both to convey the effort that goes into releasing software of this complexity with the appropriate quality and to give some assurance of the quality of the final software that has been produced.

REFERENCES

Borg G. A. (1982). Psychophysical bases of perceived exertion. *Medicine and Science in Sports and Exercise*, 14, 377-381.

Mullen, S. P., Olson, E. A., Phillips, S. M., et al. (2011). Measuring enjoyment of physical activity in older adults: invariance of the physical activity enjoyment scale (PACES) across group and time. *International Journal of Behavioral Nutrition and Physical Activity*, 8, 103-111.

Part-6-Project-610633_Deliverable-3.6: Music Processing Method;

Introduction

This deliverable D3.6 describes the current status and the work performed between month 24 and 30, concerning task 3.1 "Music tools development". This task started in month 5 and is ongoing until month 30. The goal of task 3.1 is to develop tools that assist the selection and manipulation of auditory stimuli so that they suit the synchronization and entrainment goals related to specific users coming from target populations. A proper choice of the stimulus is needed in view of an optimization of the entrainment for the target population(s) and target task(s).

In earlier deliverables (e.g. D3.3) we thoroughly discussed the music selection process. Within the last six months the focus of the work in task 3.1 was on analyzing and selecting music to be used in the proof-of-concept (PoC) for both BeatPark and BeatRun. In addition, the focus was on dissemination tasks that are related to the work in task 3.1. This mainly concerned rewriting and resubmitting a research paper after peer review in PLOS ONE.

Working towards the PoC of both BeatPark and BeatRun there is a strong interconnection between WP3 and the other WPs in the project.

Task 3.1.1: Audio Feature Extraction & Manipulation

In the last six months no additional work on audio feature extraction and manipulation has been done. Related to this, a research article had been submitted to PLOS ONE on the influence of musical expression on the velocity of walking (Buhmann, Desmet, Moens, Van Dyck, & Leman, 2016). In the past few months this article has been reviewed, revised and resubmitted (on the basis of minor revisions). We have good hopes that the revised paper will be accepted.

Task 3.1.2: Music Generation

In the last six months no additional work on music generation has been done.

Task 3.1.3: Music Database

For the PoC of both BeatPark and BeatRun a music database is created, containing user- and task-specific music. This was done with a semi-automatic approach that has been described elaborately in deliverable D3.3.

BeatPark Proof-of-Concept

The BeatHealth system can modify the tempo of a song without changing the pitch. In order to maintain the characteristics of a song the maximum tempo adaptation is set to 5%.

The following factors are taken into account to calculate the minimum size of the music database for PD patients Average SPM for walking lies somewhere around 100 SPM For a song at 100 BPM, songs can be selected (and adapted) from 95 BPM (−5%) to 105 BPM (+5%): a range of 10 BPM BPM range of songs in database: 80-130 BPM=5 bins of 10 BPM PD patients will be requested to walk 30 min per training session during the PoC: duration of approximately 10 songs A PD patient should be able to choose music from 5 different genres ==>5 bins×10 songs×5 genres=250 songs In total 664 songs were preselected (based on BPM, user preferences, and similar artists, genres or decade) from which we kept 285 songs (43%), spread over 6 genres. To cover most of the user preferences it was decided to have an extra genre. Therefore, our goal was to have at least 8 instead of 10 songs per 10 BPM-range. Participants of the PoC will be asked to choose at least two of the six genres, before starting a walk/activity. This way we ensure there are enough different songs to be played. We went a little over the initial 1Gb requirement that was set by the partners from Maynooth, but with the latest decisions on the type of phones to be used, this is certainly no longer problematic.

Table 9 lists the number of songs per genre and BPM-range. In some cases we did not find eight or more songs that were suitable. To overcome this problem we added extra songs to adjacent BPM ranges.

TABLE 9

Distribution of songs for BeatPark music database: number of songs per genre and BPM range

| BMP | disco | pop | soft-pop | pop-rock | variété | instru-mental | Total |
|---|---|---|---|---|---|---|---|
| 60-70 | 0 | 0 | 0 | 0 | 1 | 0 | 1 |
| 70-80 | 0 | 2 | 1 | 0 | 0 | 2 | 5 |
| 80-90 | 8 | 7 | 8 | 8 | 8 | 6 | 45 |
| 90-100 | 9 | 13 | 8 | 8 | 8 | 9 | 55 |
| 100-110 | 12 | 10 | 8 | 9 | 7 | 9 | 55 |
| 110-120 | 11 | 13 | 8 | 7 | 10 | 9 | 58 |
| 120-130 | 10 | 12 | 8 | 8 | 8 | 6 | 52 |
| 130-140 | 3 | 4 | 0 | 1 | 4 | 2 | 14 |
| Total | 53 | 61 | 41 | 41 | 46 | 43 | 285 |

BeatRun Proof-of-Concept

For BeatHealth for runners the database size calculation is more or less the same:

Average SPM for running lies somewhere around 160 SPM

For a song at 160 BPM, songs can be selected (and adapted) from 152 BPM (−5%) to 168 BPM (+5%): a range of 16 BPM BPM range of songs in database: 120-200 BPM=5 bins of 16 BPM Runners will be requested to run 30 min per training session during the PoC: duration of approximately 10 songs A runner should be able to choose music from 5 different genres ==>5 bins×10 songs×5 genres=250 songs The collection and analysis of songs for BeatRun is still in progress. Currently 72 songs have been added to the database. We plan to have the database large enough for the task 2.3 experiment and to have it finalized for the BeatRun PoC.

Task 3.1.4: Entrainment Mappings

In the last six months no new music alignment strategies have been implemented. However, for task 2.3 fine-tuning of the parameters of the Kuramoto model as we plan to implement it for the PoC is in progress. The results will be summarized in deliverable D2.4. Meanwhile work is also in progress on a publication of last year's experiment on comparing different alignment strategies with regard to kinematic responses (synchronization, cadence, speed) and motivation. The data has been analyzed and we plan to start writing the research article in April.

Conclusions

This deliverable D3.6 presents the progress in the development of music selection and manipulation tools in the last six months.

In subtask3.1.1 dissemination work was done in the form of rewriting and resubmitting a research paper, after peer review by PLOS ONE.

Within subtask 3.1.3, the earlier defined protocol for analyzing and selection of user- and task-specific music was used to generate a complete music database of 285 songs for the BeatPark PoC. Work is still in progress for a similar music database for running, to be used in the BeatRun PoC.

In the last six month no additional work was scheduled or done in subtask 3.1.2 and 3.1.4.

REFERENCES

1. Buhmann, J., Desmet, F., Moens, B., Van Dyck, E., & Leman, M. (2016). "Spontaneous velocity effect of musical expression on self-paced walking". PloS one, submitted.

Part 7-Project-610633_Deliverable-5.4: Results and Tests.

The present deliverable has been written based on the BeatRun experimental data collected until Friday the $21^{st}$ of October. The analysis is focused on a reduced number of variables. This document nevertheless represents the backbone of an article that we plan to submit as soon as all data are collected.

General Approach

The general goal of BEATRUN POC was to evaluate the influence of BeatRun architecture on a running training program involving young adults. The lack of consistency of the relation between running economy and rhythmical auditory stimulations across the population of runners tested, encouraged the consortium to redefine the purpose and methods of BeatRun POC. We proposed to use the potential of BeatHealth technological architecture to manipulate runners' steps cadence. The real time step detection and beat adaptation algorithm makes indeed possible the manipulation of tempo and phase independently. Task 2.3 (see Deliverable D2.4) confirmed the hypothesis that running cadence can be modulated by the phase of RAS. More specifically, the combination of gait matching tempo and negative phase shift elicits a phase correction response resulting in an increased cadence. Symmetrically, the combination of gait matching tempo with positive phase shift is an incentive to decrease cadence. We used the former association of parameters to guide the cadence of runners toward higher values. This approach was motivated by the discrepancy between shod and barefoot running cadences: the last one is reported to be usually higher than the former one. Among the reasons why, most of runners adopt higher cadence when shod, the reduction of sensory feedback is often cited. This explanation associates barefoot cadence with a more natural gait pattern than shod cadence and would be beneficial in terms of biomechanical constraints.

Scientific Background

Running is more and more popular (Fields et al., 2010) with the number of participants in running competitions open to recreational runners beating new records every year.

If this growing sport practise is associated with many societal benefits such as a better fitness for a large span of the population, the incidence of injuries is expected to increase too (van der Worp et al., 2015). The yearly incidence of long-distance running injuries varies across studies from 19 to 79% (van Gent et al., 2007): this rate is pointing toward a societal challenge, the prevention of running injuries occurrence.

The Barefoot Running "Trend" and Footfall Pattern

The problem of running injuries could be addressed at the population scale if an ecologically measurable macro variable was identified as a factor of injuries. The seminal work of Lieberman et al. (2010) popularised the idea that before the invention of modern shoes and their cushioning properties, humans were barefoot runners who probably landed their feet flat on the ground or on the forefoot. The addition of cushioning material in shoes would have favoured the adoption of rear-foot striking by contemporary runners. Lieberman et al. (2010) promoted "barefoot running style that minimises impact peaks". As a complement of the intuitive anthropologic argument, many studies evaluated the benefits and drawbacks of barefoot running. Shod and barefoot running styles are characterised by strong kinematic specificities, which are associated with kinetic differences. McNair and Marshall (McNair & Marshall, 1994) observed higher and earlier peak tibial acceleration for barefoot than for shod running. This could partly explain the earlier impact peak force and the higher and earlier external vertical loading rate (De Wit & De Clercq, 1997; De Wit et al., 2000) when running barefoot.

Forefoot strike, which is supposed to be the corollary of barefoot running, is commonly promoted as a way to reduce loading and the associated injuries. Rearfoot strikers indeed exhibit higher impact force when running barefoot compared to shod condition. On the contrary, forefoot strike does not generate the impact transient, whatever the condition, barefoot or shod. However the idea defended by Lieberman et al. (2010) that transient impact peak disappears when landing on forefoot, can be challenged when considering the frequency spectrum of GRF. Gruber et al. (Gruber et al., 2011) analysed the frequency domain of GRF during barefoot running and concluded to a delay of the impact peak, not to its disappearance. So the initial claim that barefoot running would be beneficial to limit the deleterious effects of repeated impacts is being called into question. An in depth understanding of the biomechanical mechanisms governing rearfoot and forefoot strikes and the associated impact absorption mechanisms are necessary to figure out the exactitude of this assumption.

Lower Limb Loading

Beyond the running modality, shod or barefoot, the foot placement appears to redistribute the biomechanical constraints across the lower limb. Using modified vector coding technique, it is possible to assess coordination of different parts of the foot (Chang et al., 2008). Rearfoot strike supposes rearfoot eversion followed by forefoot eversion, whereas in the case of forefoot strike, both forefoot and rearfoot eversions are concomitant (Hamill, 2012); in other words, the forefoot and midfoot could be assimilated to a rigid structure when running barefoot. According to these assumptions higher stress would be put on Achilles tendon and metatarsal heads. As a whole, a change of footfall pattern can have acute effects on kinetics and joint coordination, and subsequently lead to a redistribution of joint moments: as illustrated by Kleindienst et al. study (Kleindienst et al., 2007), forefoot strike elicits higher knee adduction and external rotation moments. The shift from rearfoot to forefoot strike leads to a reorganisation of the joint stiffness control, with a stiffer knee and a more compliant ankle (Hamill et al., 2014). If a short-term change of footfall pattern is possible, the adaptation of muscles recruitment to accommodate the new stress requires probably more time, increasing the risk of injury (Butler et al., 2003).

How can Runners Limit the Risk of Injury?

Generally, these results suggest that the footfall pattern affects in a differentiate way lower limb joints. It is difficult to conclude to a clear advantage of one running technique despite the now popular enthusiasm for barefoot running. Manufacturers recently put on the market new shoes which are said to give the claimed advantages of barefoot running within shoes. In other words, minimal shoes are supposed to allow natural foot placement. However in Hamill et al. study (Hamill et al., 2011), rearfoot footfall pattern runners all maintained the same foot placement at impact, even in the footwear condition with no midsole. There is a risk for users focused on what a technological manipulation allows, to forget to strengthen muscles which are not usually trained in traditional shoes (Nigg BM, 2010). The debate about foot placementwould benefit from taking into account subjective preference.

Cadence Manipulation and Prevention of Injuries

An efficient reduction of loads experienced by the ankle and knee should rely on an individual approach, ideally based on the progressive manipulation of one macro biomechanical variable. The influence of cadence manipulation, increased by 5 to 10% above the natural value, has been investigated with positive results. Chumanov et al. (2012) indirectly investigated internal loading by recording muscular activities. When steps frequency increases, they reported a larger activation of muscles during the late swing phase, whereas no difference was noticed during the stance phase. The late swing phase, which is the pre-impact one, is crucial to regulate the leg stiffness during the support phase. The increased of hamstring activity contributes to flatten the foot position at impact (Heiderscheit et al., 2011) and decreased the braking force associated with higher foot inclination. This is perfectly in agreement with kinetic data reported by the same group (Heiderscheit et al., 2011): the knee and the hip absorbed less mechanical energy when steps frequency was increased by 10%. The knee joint appears to be most sensitive to changes cadence with significant changes in energy absorption being significant for a 5% increase of steps per minute. The increased activities observed for the gluteus medius and maximus could contribute to limit the development of high hip abduction moment during the stance phase. Moreover reinforcing the activities of hip extensors could be beneficial to prevent the anterior knee pain. The weakness of gluteus muscles has indeed been reported among subjects suffering from patellofemoral pain (Souza & Powers, 2009; Brindle et al., 2003) and such rehabilitation approach has already been advocated (Fredericson et al., 2000; Geraci & Brown, 2005). A reduction of the risk of tibial stress fracture has been claimed when running with shorter stride length (Edwards et al., 2009). Manipulating cadence was also revealed to be advantageous for the ankle: a reduction of plantar loading was reported when the cadence was slightly increased Wellenkotter et al. (2014).

Some injuries prevention mechanisms can be explained by the spring-mass model, which is widely considered as being representative of human running mechanics. In this model a single point mass stands for the body mass and a single linear spring for the lower limb (Alexander, 1988). When the steps frequency increases, or when the stride length decreases, the leg stiffness increases whereas the opposite is noticed for lower stride frequency (Farley & Gonzalez, 1996). Morin et al. (2007) argued that cadence was an indirect determinant of leg stiffness, the manipulation of contact time having revealed a more direct relationship with the spring-mass behaviour of the leg. A change of cadence nevertheless affects contact time and subsequently the leg stiffness. It is probably the most appropriate approach among non-specialists: altering the balance between contact time and aerial time will appear to be a challenging task for most of runners, whereas a change of cadence is doable without training. An appropriate level of stiffness limits joint motion, ensuring less energy absorption and good performances, and prevents soft tissue injuries by preventing the excessive joint motion. High-arched runners exhibit increased leg stiffness, increased sagittal plane support moment, greater vertical loading rates, decreased knee flexion excursion and increased activation of the knee extensor musculature (Williams et al., 2004). Compared to low-arched runners, they sustain a lower rate of knee and soft tissue injuries (Williams et al., 2001). Similarly the lower stiffness of knee of female athletes measured while hopping, would explain the higher incidence of knee ligamentous injuries experienced by women (Granata et al., 2002). The advantage of high stiffness for the prevention of injuries does not appear to be valid for all types of trauma. Bony injuries would be more common among runners whose the leg stiffness is high (Williams et al., 2001).

We can postulate that there is an ideal range of stiffness that conciliates good performance and a low injury risk. Because of the relation between running cadence and leg stiffness, and the possibility to easily manipulate it, we proposed to focus the present study on this variable.

Optimal Cadence

The criterion chosen by runners to select the optimal stride frequency seems to be energy consumption (Hogberg, 1952; Cavanagh & Williams, 1982; Hunter & Smith, 2007). Both novice and experienced runners tend to choose a stride frequency lower than the optimal one. However, the gap between self-selected cadence and the optimal one is significantly larger among novices (de Ruiter et al., 2014). The goal of the present study was to propose an intervention able to attract runners toward the ideal range of cadence. Thompson et al. (2014) tested the influence of stride frequency variation while running barefoot or shod. Their results suggest that the kinetic changes usually associated with barefoot running would be in fact triggered by the reduction of stride length triggered by barefoot running. We propose to combine the potential kinetic benefits of barefoot running with shod running. Despite the existence of an optimal cadence for most of runners around 170 steps per minute (Lieberman et al., 2015b), we chose an individualised approach. To this aim, we considered that when running barefoot, participants adopted a cadence that entailed kinetic changes and a potential reduction of running-related injuries. Using this cadence as a target, we manipulated the beats of musical samples that participants were listening to.

Hypotheses

The training program was specifically designed to compare the effects of the musical beat manipulation algorithm developed in the BeatHealth project with another algorithm representative of the state of the art algorithm available in commercial apps. To this aim the program involved running with the support of BeatHealth during 5 weeks with two beat manipulation algorithms used in alternation during 5 sessions over 2 and half weeks periods. Cadence during barefoot running was used as the target cadence. We tested the ability of each algorithm to attract participants' cadence toward this target. The $1^{st}$ algorithm tested (periodic) entailed a fixed inter-beat period equal to the inter-step period measured during barefoot running and beat-step relative phase starting at zero degree. It was assumed that participants would match music tempo. The second algorithm (Kuramoto) was tempo and phase adaptive. The main assumption associated with this algorithm is the attraction exerted by the phase difference on the participant who is expected to minimise the relative phase between steps and beats. Because the phase difference is maintained as long as the participant does not match the target tempo, the tempo was influenced through phase manipulation: participants were supposed to be entrained to the target tempo through phase matching.

The goal of both interventions being to attract the runner toward a target cadence, the kinematic parameters after 5 sessions of training with Kuramoto, and after 5 sessions of training with periodic alignment strategies, were compared. In the absence of any instruction given to the participants regarding steps synchronisation with the beats, we hypothesised a potential subconscious influence of both algorithms on running cadence. We formulated two specific hypotheses in relation with the variables collected:

1. If both types of beats manipulations were expected to attract runners toward the predetermined ideal steps frequency, the Kuramoto algorithm, due to the adaptive properties associated with, was hypothesised to have a stronger effect than a periodic beat delivered at the target frequency.
2. An appropriate running cadence should improve runners' energy efficiency and should also reduce the side effects of repeated ground impacts. These measures were not part of the present study, but an improvement of motivational parameters was hypothesised to be associated with the convergence of the running cadence toward the target one. The algorithm having the strongest influence on cadence was also assumed to be better ranked by participants in terms of motivation.

Gait related data collected with inertial motion sensors were used to test the first hypothesis. The second hypothesis was tested through the analysis of degree of satisfaction and motivation to perform physical activity.

Methods

Technological Architecture

Sensors

Bluetooth 4 sensors were considered to be the most appropriate choice for sensors used by the BeatHealth mobile platform. The combination of two types of sensors, inertial motion units and heart rate sensor, provided synchronised kinematic and physiological data.

Inertial Motion Units

BH4 sensors have combined accelerometers, gyrometers and magnetometers, and produce 100 samples/sec. The battery and the sensors are fitted in a small box. One sensor was attached to each ankle with easy to fit elastic straps.

Zephyr H×M Heart Rate Sensor

The heart rate sensor was attached to the participant's chest with a strap.

Global Positioning System (GPS) Data

The GPS from the Android phone was logged with their time stamps every second. The collection of geographic data with coordinates in latitude and longitude gives online access to distance and speed related parameters.

Fusion of all Sensors Data

The synchronised acquisition of all sensors data provided objective measures of topographic parameters of each run and the associated participant's kinematic and physiological variables. The details of collected variables are listed in the cloud section.

Questionnaires

Borg Scale or Rate of Perceived Exertion

The rating of perceived exertion (RPE) was measured by the Borg rating of perceived exertion scale. After each running session, participant was invited to select on a scale ranging from 6 to 20 the value which best described his level of exertion.

PACES Questionnaire

The 8-item PACES scale was used to assess participants' enjoyment. Respondents were asked to rate how they agree or disagree with 8 adjectives describing their running session. On the screen of the phone, they had to move a cursor along a line marked out at left and right limits by "totally agree" and "totally disagree". The distance from the right limit of the scale to the cursor location was recorded. All 8 items related distances were summed to calculate the final score. Higher PACES score reflected greater level of enjoyment.

The Cloud Architecture

When closing the app (or when session is finished and cannot disturb the process), the app starts the cloud connection service in background. The files containing all the variables listed below are uploaded in the cloud. Data stored in the cloud are only accessible by the experimenter and can be downloaded as ASCII files for offline analysis.

1. User profile
   a. Email: anonymous e-mail accounts created for the POC
2. Session characteristics
   a. Session number
   b. Status (Completed, Incomplete, On-going, . . . )
   c. Scheduled time (Defined, 30 minutes)
   d. Start date & time
   e. Running time (Time using the system, not including possible pauses)
   f. End date & time
   g. Algorithm A: interactive cueing
   h. Algorithm B: interactive cueing/fixed cueing
3. Gait related data
   a. Foot-ground contact timestamps array right foot
   b. Foot-ground contact timestamps array left foot
   c. Cadence array
   d. Speed array
   e. Step length array
   f. Stride length array
   g. Playlist array (List of songs played during the session)
   h. Beat timestamps array (Timestamps for the music beats)
4. Heart-rate data
   a. Timestamps
   b. Heart rate
5. GPS track
   a. Timestamp (GPS data acquisition starting time)
   b. Total distance walked/run
   c. Average speed
   d. Timestamp array (timestamps for each of the following GPS data)
   e. Latitude array
   f. Longitude array
   g. Elevation array Musical Database A music database was created containing songs ranging from 130 to 200 BPM. For ecological purposes and making running sessions a unique personal experience, the music selection was based on user preferences.

The same method as for the BeatPARK music database was adopted:

A google sheets document with some questions about preferred music for running was set-up in Ghent
   The BeatRUN POC experimenters distributed this google sheets document to the POC participants
   Participants shared their musical preferences by:
      Filling in the questions in the document
      Preferably, by creating a favourite playlist in Spotify and sharing this playlist for further analysis. Participants made the playlist public and then e-mailed the link.
   The preferred music was analysed in Ghent and the songs that were appropriate for running were selected for the final database. The user preferences were also used to add similar music to the database, in order to extend the database, which finally contained 250 songs, spread over 6 genres.

Protocol

POC testing evaluated the motivational effects of music on a regular training plan and the relevance of the musical adaptation algorithm. It was also the opportunity to assess the relevance of a number of technical choices: user interface, sensors and cloud services. One group of young adults participated in a 9-week training program via rhythmic stimulation using BeatRun POC. The program involved running with the support of BeatHealth two times a week. The duration of the sessions, which represented the only assignment for the participant, was adjusted as a function of training progression. It was proposed to compare the effects of Kuramoto algorithm (Kuramoto) with periodic (Periodic) RAS tuned at participant's running frequency. Half of the participants first underwent Kuramoto and then periodic whilst the other half started with periodic and then underwent Kuramoto.

Participants 29 participants (16 females and 13 males, 33.3±10.2 years) gave their informed consent to test a mobile application during a 9 weeks running training program including 17 sessions (training and testing sessions combined). They practised sport weekly during at least 2 hours and up to 12 hours, but none of them was an expert runner. 14 of them had a musical background with at least 2 years training.

Two consecutive sessions should have been 48 hours apart. They were asked to report any difficulty that appeared during the use of the app and any discomfort or pain experienced during the training.

Training Program

Both training and test sessions were implemented in the app (see table 10). Both types of session did not differentiate from each other fundamentally, all sessions being defined by two parameters:

The characteristics of the auditory stimulations: silence/ algo 1/algo 2

The duration: 20'/25'/30'/35'/40'

Participants, when they started BeatRun application could see on the home page of the app the complete list of sessions being part of the training plan. They were invited to complete the upcoming session characterised by a specific duration. Once they had completed one session, this session was marked as completed and the next session was displayed as being the upcoming goal.

During an initial meeting with the experimenters, the participant, after being officially included in the study, was informed about the specificities of the training plan and was trained to use the equipment: this includes the use of the application and the sensors placement. The participant was asked to run during each session at a self-selected comfortable pace and to match the duration specified by the app. At the beginning of the session, he had to initialise the app: after having connected sensors and having selected favourite musical genre(s), the app indicated the duration of the session. The participant had simply to press "Start" button to initiate data acquisition and musical stimulations, if there were any associated with the session.

Pre-training consisted in four sessions (two 20' sessions and two 25' sessions) without any auditory stimulation. Participants set-up the equipment for pre-training sessions as they did during training and testing sessions. This approach ensured that they were familiar with sensors and application use when musical training started.

After the pretest (testing sessions are described in the next section), participants had to complete 5 training sessions whose the duration ranged from 30 to 35'. They were listening to music whose the beat was manipulated with the first tested algorithm (Kuramoto or Periodic according to the group participant was assigned to). They completed the first post-test session before embarking on the second training period also consisting in 5 running sessions with musical samples manipulated with the second algorithm. The second post-test ended the experiment.

TABLE 10

Complete list of sessions implemented in BeatRun app

| Session number | Task | Auditory stimulation | Week | Duration |
|---|---|---|---|---|
| 1 | Pre-training | Silence | 1 | 20 |
| 2 | Pre-training | Silence | 1 | 20 |
| 3 | Pre-training | Silence | 2 | 25 |
| 4 | Pre-training | Silence | 2 | 25 |
| 5 | Pretest | Silence | 3 | 25 |
| 6 | BH training | Algo. 1 | 3 | 30 |
| 7 | BH training | Algo. 1 | 4 | 30 |
| 8 | BH training | Algo. 1 | 4 | 35 |
| 9 | BH training | Algo. 1 | 5 | 35 |
| 10 | BH training | Algo. 1 | 5 | 30 |
| 11 | Post-test 1 | Silence + Algo. 1 | 6 | 25 |
| 12 | BH training | Algo. 2 | 6 | 35 |
| 13 | BH training | Algo. 2 | 7 | 35 |
| 14 | BH training | Algo. 2 | 7 | 40 |
| 15 | BH training | Algo. 2 | 8 | 40 |
| 16 | BH training | Algo. 2 | 8 | 35 |
| 17 | Post-test 2 | Silence + Algo. 2 | 9 | 25 |

Testing Sessions

Figure 83:
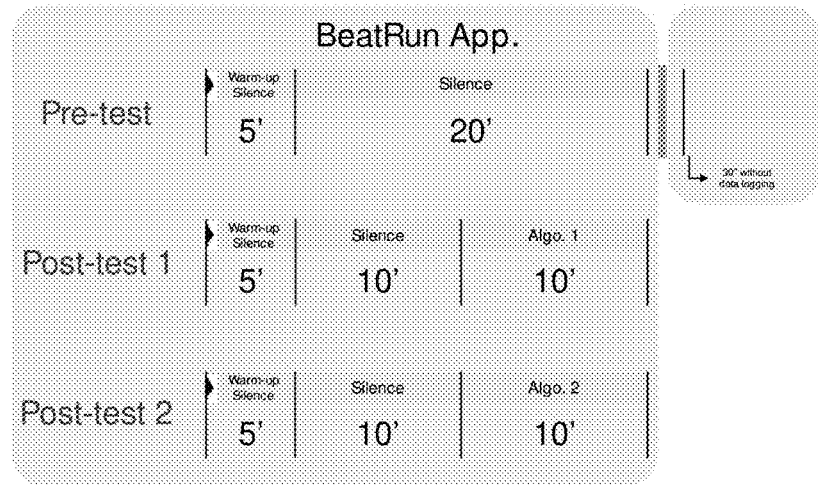

In FIG. 83, participants run 25 minutes during all 3 testing sessions. Each testing session consisted in 25 minutes of running at a comfortable self-selected pace with the complete set-up i.e. the phone and the sensors. The app did not provide any stimulation during the pre-test session. They experienced 15 minutes of silence and 10 minutes of auditory stimulations during both post-tests sessions (FIG. 1). All testing sessions took place at the running track of the Nationale Watersportbaan Georges Nachez in Ghent, Belgium. This 4967 m long outdoor track encloses a river section (currently most often used for professional rowing training) and consists of a wood bark surface, prepared especially for running purposes. Following the pre-test session, participants were invited in the Flanders Sports Arena, a 200 m indoor athletics track covered with tartan, to perform the bear foot running test. They were instructed to run barefoot during 4 minutes without any auditory stimulation.

Algorithms

When the participant was listening to music, the time stamps of the beats were manipulated. Two different algorithms defined two beat-steps alignment strategies. Both algorithms required the identification of the target runner's cadence. The target cadence, determined during the bare foot running test, was the frequency towards which the experimenter wanted to attract the participant.

The periodic algorithm ensured music tempo matching with participant's target cadence and perfect beat-step synchrony at the onset of the stimulations.

To implement adaptive stimulation we decided to adopt a mapping strategy based on a phase oscillator dynamics (Kuramoto model of synchronisation) that appeared as particularly appropriate for runners (see Deliverable D2.4). The simple phase oscillator possesses its own preferred frequency and coupling parameters which controls its tendency to phase lock to the cadence of the runner.

We chose to adapt weakly the beat frequency to the cadence of the runner. Due to the specificities of running in ecological condition a modified Kuramoto model has been developed (see Deliverable D2.4). This version of the model eliminated undesirable properties of the original model such as instability when stride frequency diverges too much from the target or the tempo independent coupling strength. The model drives the human oscillator towards the target frequency by manipulating the music oscillator. The key parameters that were adjusted controlled the responsiveness of the model, how the music frequency was adapted to the runner's frequency, and the stable phase difference at synchronisation.

These parameters were adjusted so that the adaptive cueing stimulus had the tendency to increase the cadence of the user while maintaining frequency matching and relatively stable phase-locking. The objective was to entrain the runner to the target cadence in a natural way.

Output Variables and Statistical Analysis

Influence of BH POC on Runners' Step Frequency

Cadence and speed were averaged over the pre-test session after warm-up between minute 6 and minute 15. Similarly during post-test sessions 1 and 2, the average speed was calculated over two intervals: from minute 6 to minute 15 (silence), and from minute 16 to minute 25 (music).

The effect of training on running average cadence in silence was assessed with one-way (3 testing sessions: pretest/post-test 1/post-test 2) repeated-measures ANOVA. Delta cadence silence was calculated by subtracting from the average cadence (silence) during post-tests the average cadence recorded in the previous test (silence). So cadence during pretest was subtracted from cadence during post-test 1 (silence) and cadence during post-test 1 (silence) was subtracted from cadence (silence) during post-test 2. This variable was considered as an indicator of the influence of training with a specific algorithm on cadence. Similarly we calculated delta cadence music by subtracting from the average cadence (music) during post-tests the average cadence (silence) recorded in the previous test (pretest or previous post-test). This variable assessed the combination of the training and the listening of the music on cadence. To evaluate effect of algorithms on running cadence in silence on one hand, and effect of algorithms on running cadence in music, we conducted two different two-way mixed ANOVA to test respectively statistical significant differences between average delta cadences in silence, and between average delta cadence in music. One between subject factor was the testing order of the algorithms over the course of the training (Periodic-Kuramoto/Kuramoto-Periodic), and one within-subject factor was the algorithm (Periodic/Kuramoto).

The effect of training on running cadence was assessed with a one-way (3 testing sessions: pretest/post-test 1/post-test 2) repeated-measures ANOVA. A two-factors, auditory modality (silence/music)×algorithms (periodic/Kuramoto), repeated-measures ANOVA tested the combined influence of music and algorithms on speed compared to silence.

Motivational Aspects

Figure 84:
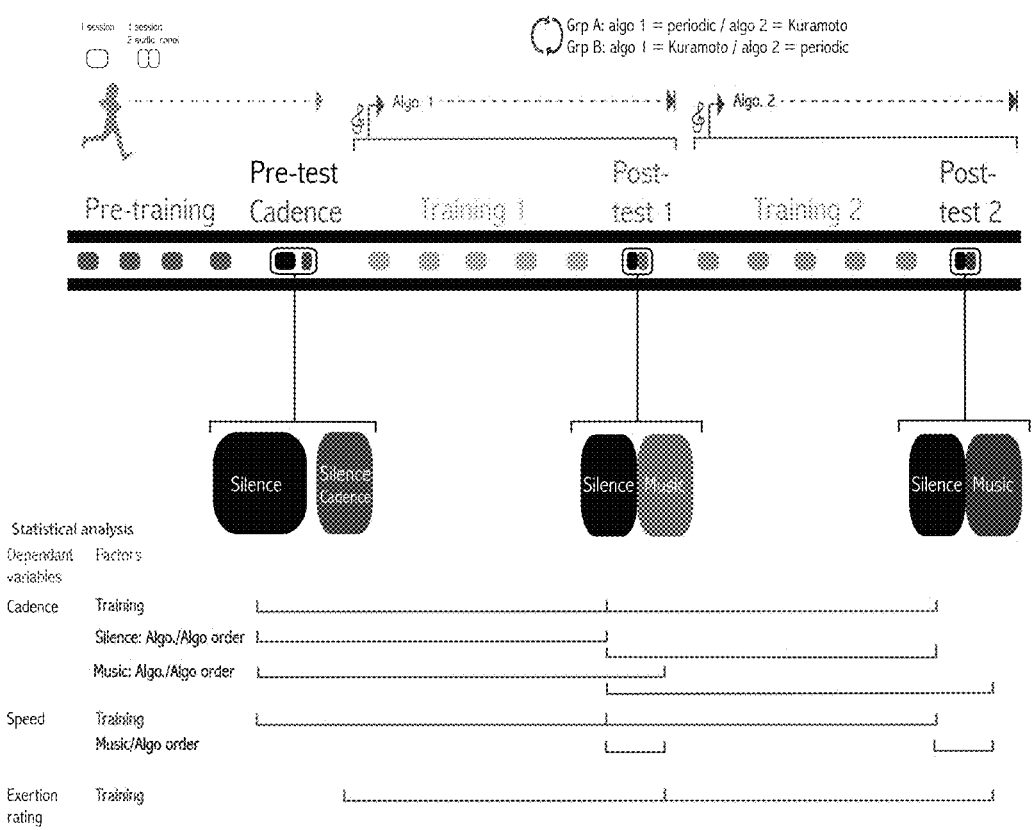

To assess the effects of BeatRun on motivational aspects of running, in FIG. 84, the rating of perceived exertion indicated by participants at the end of each session was compared across training and auditory conditions. The effect of training was first assessed with a one-way (3 testing sessions: pretest/post-test 1/post-test 2) repeated-measures ANOVA. The potential effect of algorithms on the Borg score reported by participants was assessed with a two-way, testing order of the algorithms (Periodic-Kuramoto/Kuramoto-Periodic)×algorithms (periodic/Kuramoto) repeated measures ANOVA.

Data from the Physical Activity Enjoyment Scale-8 factors have not been analysed yet.

Results

Training Plan Completion

At the time of writing this report, 21 complete sets of data had been collected. Two extra sets were expected later. The data from 6 participants out of 29 have been discarded: two participants gave up the training, one inappropriately positioned the sensors during too many sessions making the musical adaptation irrelevant and finally one did not meet the prescribed number of training sessions between testing sessions. For one participant, data were not appropriately logged during one testing session for an unknown reason.

Among the 21 participants whose data sets were analysed, 5 were excluded from the analysis of the effects of music on cadence because their average shod running cadence during pre-test was too close to their barefoot running cadence (gap<2 steps per minute). The data presented below rely on 16 participants, who exhibited an average increase of $7.63\pm3.12$ steps·min$^{-1}$ during barefoot running.

Cadence

Effect of Training on Cadence

SPM increased from $160.45\pm7.6$ steps·min$^{-1}$ during pre-test to $161.71\pm9.44$ steps·min$^{-1}$ into the training to $164.69\pm9.1$ steps·min$^{-1}$ at the end of the training (FIG. 3). A one-way repeated measures ANOVA was conducted to determine whether there were statistically significant differences in cadence over the course of the training. No outlier was observed on a boxplot. Cadence was normally distributed at each time point, as assessed by Shapiro-Wilk test (p>0.05). Mauchly's test of sphericity indicated that the assumption of sphericity had not been violated, $\chi 2(2)=3.3$, p=0.192. Cadence was statistically significantly different at the different time points during the training, $F(2, 30)=8.25$, p=0.001. Pairwise comparisons revealed significant difference between the cadence during pretest and post-test 2 (p=0.006).

Delta Cadence During Post-Tests Silence

Mixed factors ANOVA was conducted to assess the effects of algorithms and testing order of algorithms on running cadence during testing in silence. There were no outliers in the data, as assessed by inspection of a boxplot and the examination of studentized residuals. Cadence was normally distributed, as assessed by Shapiro-Wilk's test of normality (p>0.05). There was homogeneity or variances (p>0.05) as assessed by Levene's test of homogeneity of variances. There was homogeneity of covariances, as assessed by Box's test of equality of covariance matrices (p=0.27). Despite apparent gap between the average effect of both algorithms ($0.98\pm3.9$ steps·min$^{-1}$ after training with periodic, $3.27\pm4.48$ steps·min$^{-1}$ after training with Kuramoto), the ANOVA did not reveal any significant interaction between factors nor any main effect of one of them (FIG. 3).

Delta Cadence During Post-Tests Music

Mixed factors ANOVA was conducted to assess the effects of algorithms and testing order of algorithms on running cadence during testing in music. There were no outliers in the data, as assessed by inspection of a boxplot and the examination of studentized residuals. Cadence was normally distributed, as assessed by Shapiro-Wilk's test of normality (p>0.05). There was homogeneity or variances (p>0.05) as assessed by Levene's test of homogeneity of variances. There was homogeneity of covariances, as assessed by Box's test of equality of covariance matrices (p=0.16). There was a statistically significant main effect of algorithms, $F(1, 14)=5.45$, p=0.033, partial $\eta 2=0.28$. Delta SPM with Kuramoto (training and listening) was significantly higher ($0.49\pm3.6$ steps·min$^{-1}$) than delta SPM with periodic algorithm (FIG. 3, $3.71\pm2.98$ steps·min$^{-1}$).

Speed

Effect of Training on Speed

A one-way (training session time) repeated measures ANOVA was conducted to determine whether there were statistically significant differences in speed over the course of the training. The examination of studentized residuals did not show any outlier. Data was normally distributed, as assessed by Shapiro-Wilk test (p>0.05). The observation of box plot did not reveal any outlier. Mauchly's test of sphericity indicated that the assumption of sphericity had not been violated, $\chi 2(2)=3.03$, p=0.22. There was no significant effect of time on speed. Speed did not vary across training from 10.65±1.60 km·h$^{-1}$ during pretest to 10.52±1.44 km·h$^{-1}$ into the training to 10.67±1.37 km·h$^{-1}$ at the end of the training (FIG. 3).

Effect of Music on Speed

Figure 85:
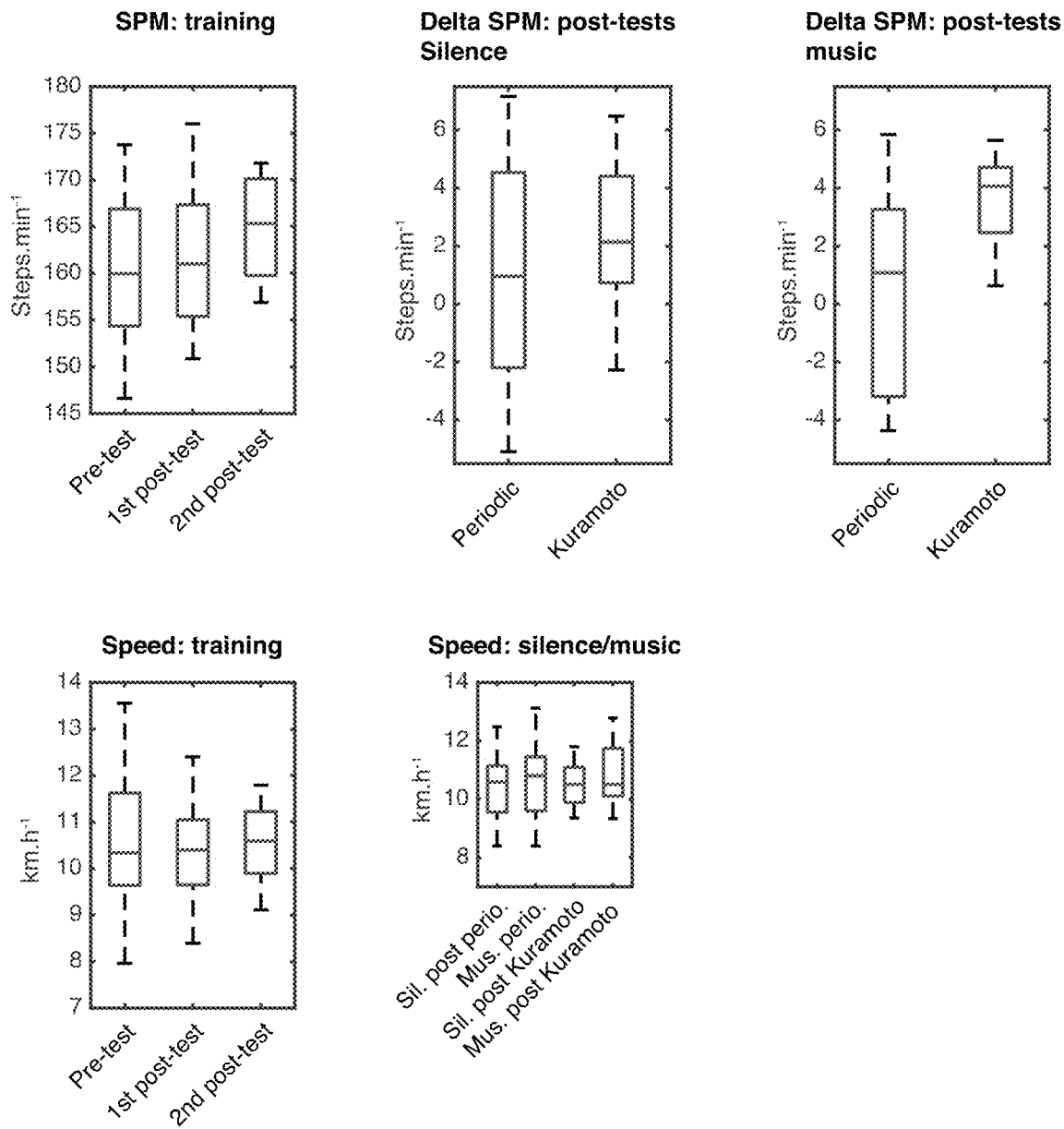

In FIG. 85, a two-way repeated measures ANOVA (algorithms Kuramoto vs. periodic×auditory modality silence vs. music) was conducted to assess the effect of music on speed. There were no outliers, as assessed by examination of studentized residuals for values greater than ±3. Speed values were normally distributed, as assessed by Shapiro-Wilk's test of normality on the studentized residuals (p>0.05). There was no significant effect of the auditory modality on speed. Both post-tests sessions were characterised by close average speed (FIG. 3, 10.52±1.55 km·h$^{-1}$ in silence vs. 10.72±1.55 km·h$^{-1}$ in music during post-test 1, 10.67±1.24 km·h$^{-1}$ in silence vs. 10.83±1.42 km·h$^{-1}$ in music during post-test 2).

Rating of Perceived Exertion

Effect of Training on Rating of Perceived Exertion

A one-way (training session time) repeated measures ANOVA was conducted to determine if the rating of perceived exertion was a function of training. We did not notice any outlier among the studentized residuals and values were normally distributed, as assessed by Shapiro-Wilk's test of normality on the studentized residuals (p>0.05). Mauchly's test of sphericity indicated that the assumption of sphericity had not been violated, $\chi2(2)=1.11$, p=0.57. No significant variation of the rating of perceived exertion was noticed across the training, the rating being representative of a "somewhat hard" effort for most of participants (pretest: 12.93±1.77, post-test1: 12.44±1.50, post-test2: 12.56±1.90).

Effect of Algorithms on Rating of Perceived Exertion

A mixed ANOVA, auditory modality (pretest silence/post-test periodic/post-test Kuramoto)×testing order of algorithms, was conducted to assess the effect of music on the rating of perceived exertion. There was no outlier, and values were normally distributed, as assessed by Shapiro-Wilk's test of normality on the studentized residuals (p>0.05). Mauchly's test of sphericity indicated that the assumption of sphericity had not been violated, $\chi2(2)=1.5$, p=0.472. There was no significant effect of the auditory modality on the rating of perceived exertion (12.94±1.77 in silence, 12.19±1.60 with periodic, 12.81±1.75 with Kuramoto).

Discussion

In summary, there is an effect of training on the runners' cadence. The Kuramoto algorithm is able to entrain participants toward a target frequency. Our data also support a better efficiency of the Kuramoto algorithm compared to periodic stimulations in terms of entrainment. However, the only variable that we have analysed so far in relation with participant's perception, the rate of perceived exertion, did not translate any improvement.

Equipment Validation in Ecological Conditions

The present work demonstrates the potential of wearable BeatRun technology for assessment of kinematic parameters during running in ecological conditions. The miniature inertial motion unit monitored human movement for long-term acquisition outside the lab. Our training plan with 17 sessions challenged the wearability of the system: since most of running sessions ended with good quality data, it appears that most of runners accommodated it.

For the time being we focused our analysis on the validation/invalidation of the initial hypotheses. Other analyses are possible thanks to the diversity of the collected data, and will provide a full understanding of the entrainment process. Particularly we will investigate in future analysis if participants synchronised their steps with the beats.

Effects of Training Vs. Effect of Music and Algorithms

Participants increased their stride frequency over the course of the training. Running in music could have contributed to the evolution of cadence. However, post-training effects of each algorithm during the silence part of post-tests were not salient, whereas algorithms differentiate themselves when participants were listening to music during post-tests. From the absence of any significant difference when comparing delta cadence during post-tests in silence and the differential effects of algorithms in music during the same testing sessions, our conclusions are two-fold:

1. Training contributes to increase cadence
2. There is an additional effect of music when the Kuramoto model manipulates the beats.

The periodic algorithm was not as successful as the Kuramoto to entrain participants despite the same target frequency. It seems that participants were less prone to be entrained by a specific tempo, than by a phase shift. This assumption opens new possibilities for technique improvement and injury risk prevention for a wide spectrum of sports.

The effects we report in the present document follow the analysis of ecological data. We emphasise the fact that testing sessions, despite the control of basic parameters such as the location of the running track and participant's equipment set-up, were also representative of daily life running conditions. In other words, we are confident in the significance of our conclusions out of the lab.

Running Kinematics

In endurance running, a large range of frequencies and lengths combinations can theoretically be used. However experienced runners tend alter primarily length to change speed (Cavanagh & Kram, 1989). Elite runners seem to have a preferred cadence which would be the optimal one in terms of energy spending (Cavanagh & Williams, 1982; Hunter & Smith, 2007; Snyder & Farley, 2011). Optimal stride frequency lies between 170 and 180 strides·min$^{-1}$ in elite or experienced runners whereas inexperienced ones prefer lower cadences (Nelson & Gregor, 1976; Elliott & Blanksby, 1979). The evaluation of stride frequency during barefoot running ensured that we assigned to each participant a realistic target. In agreement with the literature cited above, most of participants immediately adopted higher stride frequency during the barefoot test. It is worth mentioning that shod stride frequencies of participants who did not demonstrate any increase during this test ranged from 167.65 to 177.11 steps·min$^{-1}$, an interval that intersects the one reported for experienced runners. This characteristic could have averted any further rise among these participants.

Regarding participants who have a target frequency above the shod cadence, the increase of stride frequency we report following the training and the auditory conditions, was done at constant running speeds. As speed is the product of stride frequency and length, it means that participants associated higher stride frequency with shorter stride length. We mentioned in the introduction the hypothesised advantages of this combination reported in the literature: less mechanical energy absorption by lower limb joint (Heiderscheit et al., 2011), higher leg stiffness (Farley & Gonzalez, 1996) and shorter contact time (Morin et al., 2007). Our algorithm was able to attract runners in a higher interval of stride frequency, the average difference between cadences during pretest and cadences during post-test with Kuramoto was 3.84±2.61 steps·min$^{-1}$. This is half of the rise expected based on the target frequency 7.63±3.13 steps·min$^{-1}$. Having in mind the absence of any instruction given to the participant to synchronise the steps with the beats, this strategy appears to be an efficient way to manipulate runner's cadence in a subliminal way. The cadence rise elicited by the Kuramoto model represents on average a 2.46% increase expressed in fraction of the initial cadence. Biomechanical effects mentioned above were already measurable when participants ran at +5% of their preferred stride frequency (Heiderscheit et al., 2011; Thompson et al., 2014). We can reasonably assume that the results we are reporting translated into an alteration of related biomechanical constraints.

In a recent study (Lieberman et al., 2015b), higher stride frequency has been reported to be associated with the foot landing closer to the vertical of the hip and the knee. The position of the foot related to the hip was in particular strongly correlated. These kinematic changes contributed to lower the braking force, ensuring better energy efficiency. We can only infer the details of the kinematic adjustments elicited by our manipulation, but the literature globally agree on a realignment of lower limb segments with stride frequency increase. Considering the contribution of lower extremity in shock absorption (Derrick et al., 1998), such configuration could result at landing in lower rate and magnitude of the impact peak and could prevent a number of injuries such as tibial stress syndrome, Achilles tendonitis and patellofemoral pain.

Similar Perceived Effort

Despite potential benefits in terms of energy efficiency provided by the stride manipulation, the rate of perceived exertion reported by participants did not reveal any facilitation of task completion. We have to acknowledge that even if the stride frequency should favour better efficiency, this is a slight contribution to the global workload of one running session that the Borg scale translates.

Barefoot Running Benefits During Shod Running?

Like experienced runners prefer higher cadence compared to recreational ones, shod runners have reported to use lower stride frequency than barefoot runners (Squadrone & Gallozzi, 2009; Lieberman et al., 2015a). Manufacturers recently put on the market new shoes that are said to give the claimed advantages of barefoot running within shoes. In other words, minimal shoes are supposed to allow natural foot placement. Robbins and Waked (Robbins & Waked, 1997) suggested that the midsole masks the magnitude of impact shock is correct, a thinner midsole may allow runners to sense the severity of impacts and adjust kinematics accordingly. In a study by Clarke et al. (Clarke et al., 1983) using shoes with different midsole hardnesses, it was shown that subjects adjusted their running kinematics in such a way that impact forces were not grossly different. This finding was supported by Snel et al. (Snel et al., 1985), Nigg et al. (Nigg et al., 1987). However Hamill et al. (Hamill et al., 2011) showed that rearfoot footfall pattern runners all maintained the same foot placement at impact, even in the footwear condition with no midsole.

Our approach could invite the runner to adopt, when they are shod, the kinematics they would have used when running bare foot. Regular shoes still provide some advantages such as arch support and still represent the mainstream of running trainers. Moreover the transition toward minimal shoes can only be considered with great care, having in mind the redistribution of mechanical constraints they involve. Barefoot training, the strengthening of muscles which are not usually trained in traditional shoes, is essential (Nigg B M, 2010).

If like Thompson et al. (Thompson et al., 2014) support the idea, main barefoot running benefits lie in the change of cadence, manipulating directly this last parameter could be a relevant option. The Kuramoto model represents a novel approach, which has the valuable advantages of its embedded personalisation, a salient target being freely selected, and adaptability, tempo being manipulated by a phase shift.

Conclusion

BeatRun project has been pursuing the goal of improving running performance through the use of wearable sensors and rhythmical auditory stimulations. The technology that has been developed is appropriate to manipulate runners' cadence. This factor emerged in recent years in the literature as being a macro-variable that can have a strong influence on the biomechanical constraints experienced by runners. As such, the use of BeatRun, by entraining runners to adopt better kinematics through the use of music, could represent a promising way to promote a safe and enjoyable practice of running.

REFERENCES

Alexander, R. M. (1988). *Elastic mechanisms in animal movement*. Cambridge: Cambridge University Press.

Brindle, T. J., Mattacola, C., & McCrory, J. (2003). Electromyographic changes in the gluteus medius during stair ascent and descent in subjects with anterior knee pain. *Knee Surg Sports Traumatol Arthrosc*, 11 (4), 244-251.

Butler, R. J., Crowell, H. P., & Davis, I. M. (2003). Lower extremity stiffness: implications for performance and injury. *Clin Biomech* (Bristol, Avon), 18 (6), 511-517.

Cavanagh, P. R., & Kram, R. (1989). Stride length in distance running: velocity, body dimensions, and added mass effects. *Medicine and Science in Sports and Exercise*, 21 (4), 467-479.

Cavanagh, P. R., & Williams, K. R. (1982). The effect of stride length variation on oxygen uptake during distance running. *Medicine and Science in Sports and Exercise*, 14 (1), 30-35.

Chang, R., Van Emmerik, R., & Hamill, J. (2008). Quantifying rearfoot-forefoot coordination in human walking. *Journal of Biomechanics*, 41 (14), 3101-3105.

Chumanov, E. S., Wille, C. M., Michalski, M. P., & Heiderscheit, B. C. (2012). Changes in muscle activation patterns when running step rate is increased. *Gait Posture*, 36 (2), 231-235.

Clarke, T. E., Frederick, E. C., & Cooper, L. B. (1983). Biomechanical measurement of running shoe cushioning properties. In B. M. Nigg & B. A. Kerr (Eds.), *Biomechanical Aspects of Sport Shoes and Playing Surfaces* (pp. 25-33). Calgary: University of Calgary.

de Ruiter, C. J., Verdijk, P. W., Werker, W., Zuidema, M. J., & de Haan, A. (2014). Stride frequency in relation to oxygen consumption in experienced and novice runners. *Eur J Sport Sci*, 14 (3), 251-258.

De Wit, B., & De Clercq, D. (1997). Differences in sagittal plane kinematics between barefoot and shod running. In J. Bangsbo, B. Saltin, H. Bonde, Y. Hellsten, B. Ibsen, M. Kjaer, & G. Sjøgaard (Eds.), *Proceedings of the Second Annual Congress of the European College of Sport Science* (pp. 790-791). Copenhagen, Denmark: European College of Sport Science.

De Wit, B., De Clercq, D., & Aerts, P. (2000). Biomechanical analysis of the stance phase during barefoot and shod running. *Journal of Biomechanics*, 33 (3), 269-278.

Derrick, T. R., Hamill, J., & Caldwell, G. E. (1998). Energy absorption of impacts during running at various stride lengths. *Medicine and Science in Sports and Exercise,* 30 (1), 128-135.

Edwards, W. B., Taylor, D., Rudolphi, T. J., Gillette, J. C., & Derrick, T. R. (2009). Effects of stride length and running mileage on a probabilistic stress fracture model. *Medicine and Science in Sports and Exercise,* 41 (12), 2177-2184.

Elliott, B. C., & Blanksby, B. A. (1979). Optimal stride length considerations for male and female recreational runners. *British Journal of Sports Medicine,* 13 (1), 15-18.

Farley, C. T., & Gonzalez, O. (1996). Leg stiffness and stride frequency in human running. *Journal of Biomechanics,* 29 (2), 181-186.

Fields, K. B., Sykes, J. C., Walker, K. M., & Jackson, J. C. (2010). Prevention of running injuries. *Curr Sports Med Rep,* 9 (3), 176-182.

Fredericson, M., Cookingham, C. L., Chaudhari, A. M., Dowdell, B. C., Oestreicher, N., & Sahrmann, S. A. (2000). Hip abductor weakness in distance runners with iliotibial band syndrome. *Clin J Sport Med,* 10 (3), 169-175.

Geraci, M. C., & Brown, W. (2005). Evidence-based treatment of hip and pelvic injuries in runners. *Phys Med Rehabil Clin N Am,* 16 (3), 711-747.

Granata, K. P., Padua, D. A., & Wilson, S. E. (2002). Gender differences in active musculoskeletal stiffness. Part II. Quantification of leg stiffness during functional hopping tasks. *J Electromyogr Kinesiol,* 12 (2), 127-135.

Gruber, A. H., Davis, I. S., & Hamill, J. (2011). Frequency content of the vertical ground reaction force component during rearfoot and forefoot running patterns. In *Proceedings of the 8th annual meeting of the American College of Sports Medicine* (pp.). Denver.

Hamill, J. (2012). Rearfoot and forefoot footfall patterns: Implications for running-related injuries. *In Proceedings of the Biomechanics Interest Group* (pp.). Belfast.

Hamill, J., Gruber, A. H., & Derrick, T. R. (2014). Lower extremity joint stiffness characteristics during running with different footfall patterns. *Eur J Sport Sci,* 14 (2), 130-136.

Hamill, J., Russell, E., Gruber, A., & Miller, R. (2011). Impact characteristics in shod and barefoot running. *Footwear Science,* 3 (1), 33-40.

Heiderscheit, B. C., Chumanov, E. S., Michalski, M. P., Wille, C. M., & Ryan, M. B. (2011). Effects of step rate manipulation on joint mechanics during running. *Medicine and Science in Sports and Exercise,* 43 (2), 296-302.

Hogberg, P. (1952). How do stride length and stride frequency influence the energy-output during running. *Arbeitsphysiologie,* 14 (6), 437-441.

Hunter, I., & Smith, G. A. (2007). Preferred and optimal stride frequency, stiffness and economy: changes with fatigue during a 1-h high-intensity run. *Eur J Appl Physiol,* 100 (6), 653-661.

Kleindienst, F. I., Campe, S., Graf, E. S., Michel, K. J., & Witte, K. (2007). Differences between forefoot and rearfoot strike running patterns based on kinetics and kinematics. *In Proceedings of the XXV ISB Congress* (pp.). Ouro Preto, Brazil.

Lieberman, D. E., Castillo, E. R., Otarola-Castillo, E., Sang, M. K., Sigei, T. K., Ojiambo, R., Okutoyi, P., & Pitsiladis, Y. (2015a). Variation in Foot Strike Patterns among Habitually Barefoot and Shod Runners in Kenya. *PLoS ONE,* 10 (7), e0131354.

Lieberman, D. E., Venkadesan, M., Werbel, W. A., Daoud, A. I., D'Andrea, S., Davis, I. S., Mang'eni, R. O., & Pitsiladis, Y. (2010). Foot strike patterns and collision forces in habitually barefoot versus shod runners. *Nature,* 463 (7280), 531-535.

Lieberman, D. E., Warrener, A. G., Wang, J., & Castillo, E. R. (2015b). Effects of stride frequency and foot position at landing on braking force, hip torque, impact peak force and the metabolic cost of running in humans. *Journal of Experimental Biology,* 218 (Pt 21), 3406-3414.

McNair, P. J., & Marshall, R. N. (1994). Kinematic and kinetic parameters associated with running in different shoes. *British Journal of Sports Medicine,* 28 (4), 256-260.

Morin, J. B., Samozino, P., Zameziati, K., & Belli, A. (2007). Effects of altered stride frequency and contact time on leg-spring behavior in human running. *Journal of Biomechanics,* 40 (15), 3341-3348.

Nelson, R. C., & Gregor, R. J. (1976). Biomechanics of distance running: a longitudinal study. *Res Q,* 47(3), 417-428.

Nigg B M. (2010). Barefoot Concepts. In *Biomechanics of sport shoes* (pp. 195-212). Calgary: University of Calgary.

Nigg, B. M., Bahlsen, H. A., Luethi, S. M., & Stokes, S. (1987). The influence of running velocity and midsole hardness on external impact forces in heel-toe running. *Journal of Biomechanics,* 20 (10), 951-959.

Robbins, S., & Waked, E. (1997). Hazard of deceptive advertising of athletic footwear. *British Journal of Sports Medicine,* 31 (4), 299-303.

Snel, J. G., Dellman, N. J., Heerkens, Y. F., & Van Ingen Schenau, V. L. (1985). Shock absorbing characteristics of running shoes during actual running. In B. D. A. Winter, R. W. Norman, R. P. Wells, K. C. Hayes, & A. E. Patla (Eds.), *Biomechanics IX* (pp. 133-138). Champaign, Ill.: Human Kinetics Publishers.

Snyder, K. L., & Farley, C. T. (2011). Energetically optimal stride frequency in running: the effects of incline and decline. *Journal of Experimental Biology,* 214 (Pt 12), 2089-2095.

Souza, R. B., & Powers, C. M. (2009). Differences in hip kinematics, muscle strength, and muscle activation between subjects with and without patellofemoral pain. *J Orthop Sports Phys Ther,* 39 (1), 12-19.

Squadrone, R., & Gallozzi, C. (2009). Biomechanical and physiological comparison of barefoot and two shod conditions in experienced barefoot runners. *J Sports Med Phys Fitness,* 49 (1), 6-13.

Thompson, M. A., Gutmann, A., Seegmiller, J., & McGowan, C. P. (2014). The effect of stride length on the dynamics of barefoot and shod running. *Journal of Biomechanics,* 47 (11), 2745-2750.

van der Worp, M. P., ten Haaf, D. S., van Cingel, R., de Wijer, A., Nijhuis-van der Sanden, M. W., & Staal, J. B. (2015). Injuries in runners; a systematic review on risk factors and sex differences. *PLoS ONE,* 10 (2), e0114937.

van Gent, R. N., Siem, D., van Middelkoop, M., van Os, A. G., Bierma-Zeinstra, S. M., & Koes, B. W. (2007). Incidence and determinants of lower extremity running injuries in long distance runners: a systematic review. *British Journal of Sports Medicine,* 41 (8), 469-80; discussion 480.

Wellenkotter, J., Kernozek, T. W., Meardon, S., & Suchomel, T. (2014). The effects of running cadence manipulation on plantar loading in healthy runners. *Int J Sports Med,* 35 (9), 779-784.

Williams, D. S., Davis, I. M., Scholz, J. P., Hamill, J., & Buchanan, T. S. (2004). High-arched runners exhibit increased leg stiffness compared to low-arched runners. *Gait Posture*, 19 (3), 263-269.

Williams, D. S., McClay, I. S., & Hamill, J. (2001). Arch structure and injury patterns in runners. *Clin Biomech (Bristol, Avon)*, 16 (4), 341-347.

The invention claimed is:

1. A method for synchronizing a rhythmic stimulation with a biological variability, the method comprising:
   detecting, by a calculation unit, a movement dynamics on a user, using a sensor linked to the calculation unit;
   selecting, by the calculation unit, in a music library a music file based on the movement dynamics and a tempo associated with each music file of the music library;
   determining, by the calculation unit, frequency and phase parameters from the movement dynamics using a Kuramoto model and parameters comprising:
      a coupling strength,
      a parameter defining a maximum frequency deviation for a fraction of an unmodified tempo of the selected music file,
      a target frequency, and
      a maximum phase deviation between the unmodified music tempo and the target frequency; and
   playing the selected music file while adjusting the unmodified music tempo and/or phase of the selected music file as a function of the determined frequency and phase parameters.

2. The method according to claim 1, wherein the coupling strength is between 0.1 and 0.15.

3. The method according to claim 1, wherein the maximum frequency deviation is equal to 0.2.

4. The method according to claim 1, wherein the maximum phase deviation is between 0.5 and 0.7071.

5. The method according to claim 1, wherein a relative difference between the target frequency and the unmodified music tempo is in a range from +5% to −5%.

6. A device for synchronizing a rhythmic stimulation with a biological variability, comprising:
   a calculation unit configured to:
      detect a movement dynamics on a user, using a sensor linked to the calculation unit;
      select in a music library a music file based on the movement dynamics and a tempo associated with each music file of the music library;
      determine frequency and phase parameters with a coupling term from the movement dynamics using Kuramoto model and parameters comprising:
         a coupling strength;
         a parameter defining a maximum and minimum frequency deviation for a fraction of an unmodified tempo of the selected music file;
         a target frequency, and
         a maximum phase deviation between the unmodified tempo of the selected music file and the target frequency; and
      play the selected music file while adjusting the unmodified tempo of the selected music file and/or phase of the selected music file as a function of the determined frequency and phase parameters.

7. The device according of claim 6, further comprising one or more of the following:
   a communication module for communicating with at least one external device,
   a Global Positioning System unit,
   a user interface,
   a music selection system,
   an audio engine processor,
   an auto update module, and
   a sensor health monitor.

8. The device according of claim 7, wherein the communication module uses one or more of:
   Bluetooth protocol;
   WiFi protocol; and
   ANT protocol.

9. The device according to claim 6, further comprising one or more of the following:
   a power supply module,
   an inertial management unit, and
   a gyroscope module.

10. The device according to claim 9, wherein the inertial management unit uses the gyroscope module for detecting and impact with the ground.

* * * * *